(12) United States Patent
Kowalik et al.

(10) Patent No.: US 7,776,569 B2
(45) Date of Patent: Aug. 17, 2010

(54) VIRALLY-ENCODED RNAS AS SUBSTRATES, INHIBITORS AND DELIVERY VEHICLES FOR RNAI

(75) Inventors: Timothy F. Kowalik, Princeton, MA (US); Bradford M. Stadler, Marlborough, MA (US)

(73) Assignee: University of Massachusetts, Boston, MA (US)

( * ) Notice: Subject to any disclaimer, the term of this patent is extended or adjusted under 35 U.S.C. 154(b) by 589 days.

(21) Appl. No.: 10/924,454

(22) Filed: Aug. 23, 2004

(65) Prior Publication Data

US 2005/0171041 A1    Aug. 4, 2005

Related U.S. Application Data

(60) Provisional application No. 60/497,156, filed on Aug. 22, 2003, provisional application No. 60/566,114, filed on Apr. 27, 2004.

(51) Int. Cl.
*C12P 19/34* (2006.01)
*C12Q 1/68* (2006.01)
(52) U.S. Cl. .................................. 435/91.51; 435/6
(58) Field of Classification Search ................ None
See application file for complete search history.

(56) References Cited

U.S. PATENT DOCUMENTS

| 5,324,731 A | 6/1994 | Kaddurah-Daouk et al. | |
| 2005/0074887 A1* | 4/2005 | Rossi et al. | 435/456 |
| 2005/0171041 A1* | 8/2005 | Kowalik et al. | 514/44 |
| 2005/0186589 A1 | 8/2005 | Kowalik et al. | |

FOREIGN PATENT DOCUMENTS

WO    WO-2004/024863 A2    3/2004

OTHER PUBLICATIONS

Cagnon, L. et al., "Downregulation of the CCR5 beta-Chemokine Receptor and Inhibition of HIV-1 Infection by Stable VA1-Ribozyme Chimeric Transcripts", 2000, Antisense and Nuc. Acid Drug Develop., vol. 10: pp. 251-261.*
McCaffrey, A. et al., "RNA interference in adult mice", Jul. 2002, Nature, vol. 418: pp. 38-39.*
Hu, W., et al., "Inhibition of Retroviral Pathogenesis by RNA Interference", Aug. 6, 2002, Curr. Biol., vol. 12: pp. 1301-1311.*
Andersson, M. et al., "Suppression of RNA Interference by Adenovirus Virus-Associated RNA", 2005, J. Virol., vol. 79: pp. 9556-9565.*
Supplementary Figure 1, from McCaffrey et al, Nature, 2002, vol. 418, one page.*
Barton, Gregory M. et al, "Retroviral delivery of small interfering RNA into primary cells," *PNAS*, vol. 99(23):14943-14945 (2002).
Brummelkamp, Thijn R. et al, "Stable suppression of tumorigenicity by virus-mediated RNA interference," *Cancer Cell*, vol. 2:243-247 (2002).
Zhao, Ling-Jun et al, "Specific gene inhibition by adenovirus-mediated expression of small interfering RNA," *Gene*, vol. 316:137-141 (2003).
Bieleski, Lara et al., "Kaposi's Sarcoma-Associated Herpesvirus vCyclin Open Reading Frame Contains an Internal Ribosome Entry Site," *Journal of Virology*, vol. 75(4):1864-1869 (2001).
Bowden, Rory J. et al., "Murine gammaherpesvirus 68 encodes tRNA-like sequences which are expressed durin latency," *Journal of General Virology*, vol. 78:1675-1687 (1997).
Chen, Jih-H. et al., "Prediction of common secondary structures of RNAs: a genetic algorithm approach," *Nucleic Acids Research*, vol. 28(4):991-999 (2000).
Elbashir, Sayda M. et al., "Duplexes of 21-nucleotide RNAs mediate RNA interference in cultured mammalian cells," *Nature*, vol. 411:494-498 (2001).
Fields, Bernard N. et al., "Fundamental Virology," Raven Press, New York (1986).
GenBank Accession No. J01917, Ohe, K. et al., "The nucleotide sequence of a low molecular weight ribonucleic acid from cells infected with adenovirus 2," *J. Biol. Chem.*, vol. 246(22):6991-7009 (1971) Mar. 14, 1996.
GenBank Accession No. M10228, Bhat, R.A. et al., "Structural requirements of adenovirus VAI, RNA for its translation enhancement function," *Mol. Cell. Biol.*, vol. 5(1):187-196 (1985) Apr. 28, 1993.
GenBank Accession No. X02996, Steenbergh, P.H. et al., "The nucleotide sequence at the termini of adenovirus type 5 DNA," *Nucleic Acids Res.*, vol. 4(12):4371-4389 (1977) Apr. 7, 1999.
Grishok, Alla et al., "Genes and Mechanisms Related to RNA Interference Regulate Expression of the Small Temporal RNAs that Control *C. elegans* Developmental Timing," *Cell*, vol. 106:23-34 (2001).
Gwizdek, Carole et al., "Exportin-5 Mediates Nuclear Export of Minihelix-containing RNAs," *The Journal of Biological Chemistry*, vol. 278(8):5505-5508 (2003).
Hannon, Gregory J., "RNA interference," *Nature*, vol. 418:244-251 (2002).
Howe, J. Gregory et al., "Isolation and Characterization of the Genes for Two Small RNAs of Herpesvirus Papio and Their Comparison with Epstein-Barr Virus-Encoded EBER RNAs," *Journal of Virology*, vol. 62(8):2790-2798 (1988).

(Continued)

*Primary Examiner*—Michael Burkhart
(74) *Attorney, Agent, or Firm*—Lahive & Cockfield, LLP; Debra J. Milasincic, Esq.; Brian M. Erickson

(57) ABSTRACT

The present invention provides methods for identifying druggable targets in assays that feature compositions, cells and/or organisms having structured viral non-coding RNAs (svRNAs) and an RNA interference (RNAi) pathway. Methods for identifying antiviral agents and creating vaccines are also featured. The invention further provides methods for inhibiting RNAi involving svRNAs or inhibitory derivatives thereof. The invention also provides compositions for delivering siRNA and miRNA molecules derived from svRNA loci and methods of use thereof. Therapeutic methods are also featured.

31 Claims, 21 Drawing Sheets

OTHER PUBLICATIONS

Hutvágner, György et al., "A microRNA in a Multiple-Turnover RNAi Enzyme Complex," *Science*, vol. 297:2056-2060 (2002).

Hutvágner, György et al., "RNAi: nature abhors a double-strand," *Current Opinion in Genetics & Development*, vol. 12:225-232 (2002).

Hutvágner, György et al., "Sequence-Specific Inhibition of Small RNA Function," *PLoS Biology*, vol. 2(4):0465-0475 (2004).

Jacque, Jean-Marc et al., "Modulation of HIV-1 replication by RNA interference," *Nature*, vol. 418:435-438 (2002).

Lagos-Quintara, Mariana et al., "Identification of Novel Genes Coding for Small Expressed RNAs," *Science*, vol. 294:853-858 (2001).

Lau, Nelson C. et al., "An Abundant Class of Tiny RNAs with Probable Regulatory Roles in *Caenorhabditis elegans*," *Science*, vol. 294:858-862 (2001).

Lee, Nan Sook et al., "Expression of small interfering RNAs targeted against HIV-1 *rev* transcripts in human cells," *Nature Biotechnology*, vol. 19:500-505 (2002).

Li, Hongwei et al., "Induction and Suppression of RNA Silencing by an Animal Virus," *Science*, vol. 296:1319-1321 (2002).

Llave, Cesar et al., "Cleavage of *Scarecrow-like* mRNA Targets Directed by a Class of *Arabidopsis* miRNA," *Science*, vol. 297:2053-2056 (2002).

Ma, Yuliang et al., "Structure, Function, and Evolution of Adenovirus-Associated RNA: a Phylogenetic Approach," *Journal of Virology*, vol. 70(8):5083-5099 (1996).

Marschalek, Rolf et al., "CMER, an RNA encoded by human cytomegalovirus is most likely transcribed by RNA polymerase III," *Nucleic Acids Research*, vol. 17(2):631-643 (1989).

Mathews, Michael B. et al., "Adenovirus Virus-Associated RNA and Translation Control," *Journal of Virology*, vol. 65(11):5657-5662 (1991).

McManus, Michael T. et al., "Gene Silencing in Mammals by Small Interfering RNAs," *Nature Reviews*, vol. 3:737-747 (2002).

Ochs, Kerstin et al., "Interaction of Translation Initiation Factor eIF4B with the Poliovirus Internal Ribosome Entry Site," *Journal of Virology*, vol. 76(5):2113-2122 (2002).

Pfeffer, Sébastien et al., "Identification of Virus-Encoded MicroRNAs," *Science*, vol. 304:734-736 (2004).

Rhoades, Matthew W. et al., "Prediction of Plant MicroRNA Targets," *Cell*, vol. 110:513-520 (2002).

Samuel, Charles E., "Antiviral Actions of Interferons," *Clinical Microbiology Reviews*, vol. 14(4):778-809 (2001).

Silva, Jose M. et al., "RNA interference: a promising approach to antiviral therapy?" *Trends in Molecular Medicine*, vol. 8(11):505-508 (2002).

Spahn, Christian M.T. et al., "Hepatitis C Virus IRES RNA-Induced Changes in the Conformation of the 40S Ribosomal Subunit," *Science*, vol. 291:1959-1962 (2001).

Sui, Guangchao et al., "A DNA vector-based RNAi technology to suppress gene expression in mammalian cells," *PNAS*, vol. 99(8):5515-5520 (2002).

Thurner, Caroline et al., "Conserved RNA secondary structures in *Flaviviridae* genomes," *Journal of General Virology*, vol. 85:1113-1124 (2004).

Tuschl, Thomas, "Expanding small RNA interference," *Nature Biotechnology*, vol. 20:446-448 (2002).

Vincent, Karen A. et al., "Host sequences flanking the HIV provirus," *Nucleic Acids Research*, vol. 18(20):6045-6047 (1990).

Voinnet, Olivier, "RNA silencing as a plant immune system against viruses," *Trends in Genetics*, vol. 17(8):449-459 (2001).

Waterhouse, Peter M. et al., "Gene silencing as an adaptive defense against viruses," *Nature*, vol. 411:834-842 (2001).

Yi, MinKyung et al., "3' Nontranslated RNA Signals Required for Replication of Hepatitis C Virus RNA," *Journal of Virology*, vol. 77(6):3557-3568 (2003).

Batzer, Mark A. et al., "ALU Repeats and Human Genomic Diversity," *Nature*, vol. 3:370-381 (2002).

Britten, Roy J., "Mobile elements inserted in the distant past have taken on important functions," *Gene*, vol. 205:177-182 (1997).

Carthew, Richard W., "Gene silencing by double-stranded RNA," *Current Opinion in Cell Biology*, vol. 13:244-248 (2001).

Deininger, Prescott L. et al, "Alu Repeats and Human Disease," *Molecular Genetics and Metabolism*, vol. 67:183-193 (1999).

Deininger, Prescott L. et al, "Evolution of Retroposons," *Evolutionary Biology*, vol. 27:157-196 (1993).

Deininger, Prescott L. et al, "Mammalian Retroelements," *Genome Res.*, vol. 12:1455-1465 (2002).

Gu, Zhenglong et al, "Densities, length proportions, and other distributional features of repetitive sequences in the human genome estimated from 430 megabases of genomic sequence," *Gene*, vol. 259:81-88 (2000).

Jurka, Jerzy et al, "A fundamental division of the *Alu* family of repeated sequences," *Proc. Natl. Acad. Sci. USA*, vol. 85:4775-4778 (1988).

Ketting, René F. et al, "*mut-7* of *C. elegans*, Required for Transposon Silencing and RNA Interference, Is a Homolog of Werner Syndrome Helicase and RNaseD," *Cell*, vol. 99:133-141 (1999).

Knebelmann, Bertrand et al, "Splice-mediated insertion of an *Alu* sequence in the COL4A3 mRNA causing autosomal recessive Alport syndrome," *Human Molecular Genetics*, vol. 4(4):675-679 (1995).

Kreahling, Jenny et al, "The origins and implications of Alternative splicing," *Trends in Genetics*, vol. 20(1):1-4 (2004).

Lee, Yoontae et al, "The nuclear RNase III Drosha initiates microRNA processing," Nature, vol. 425:415-419 (2003).

Lev-Maor, Galit et al, "The Birth of an Alternatively Spliced Exon: 3' Splice-Site Selection in Alu Exons," Science, vol. 300:1288-1291 (2003).

Li, Tzu-Huey et al, "Differential stress induction of individual Alu loci: implications for transcription and retrotransposition," Gene, vol. 276:135-141 (2001).

Li, Wen-Hsiung et al, "Evolutionary analyses of the human genome," Nature, vol. 409:847-849 (2001).

Liu, Wen-Man et al, "Cell stress and translational inhibitors transiently increase the abundance of mammalian SINE transcripts," Nucleic Acids Research, vol. 23(10):1758-1765 (1995).

Makalowski, Wojciech, "Not Junk After all," Science, vol. 300:1246-1247 (2003).

Matzke, Marjori A. et al, "RNAi Extends Its Reach," Science, vol. 301:1060-1061 (2003).

Matzke, Marjori A. et al, "RNA-based silencing strategies in plants," Current Opinion in Genetics & Development, vol. 11:221-227 (2001).

Mitchell, Grant A. et al, "Splice-mediated insertion of an Alu sequence inactivates ornithine δ-aminotransferase: A role for Alu elements in human mutation," Proc. Natl. Acad. Sci. USA, vol. 88:815-819 (1991).

Rubin, Carol M. et al, "Selective stimulation of translational expression by Alu RNA," Nucleic Acids Research, vol. 30(14):3253-3261 (2002).

Schramke, Vera et al, "Hairpin RNAs and Retrotransposon LTRs Effect RNAi and Chromatin-Based Gene Silencing," Sciencexpress, pp. 1-6 (2003).

Sorek, Rotem et al, "Alu-Containing Exons are Alternatively Spliced," Genome Res., vol. 12:1060-1067 (2002).

Storz, Gisela, "An Expanding Universe of Noncoding RNAs," Science, vol. 296:1260-1262 (2002).

Office Action for U.S. Appl. No. 10/984,180, dated Sep. 10, 2007.

\* cited by examiner siRNA-Induced Reduction in
Virally Encoded Reporter Gene Expression
(Non-Replicating)

100 nM siRNA / oligofxn siRNA -Induced Reduction in
Virally Encoded Reporter Gene Expression
(Replicating)

100 nM siRNA / oligofxn

WT Ad-5- Induced Reduction in siRNA Activity

Recombinant Adenovirus-Induced Decrease in siRNA Activity in 293 Cells 20 nM siRNA Target Cleavage in Infected Human Cell Extracts Target 5' AGGGAAAGGAGCACTCCCCCGTTGTC    TGACG^TCG    3' (SEQ ID NO.: 114)
    3'    UUUCCUCGUGAGGGGGCAACAG    ACUGC         5'    (SEQ ID NO.: 115)
         21            11 10                  1                         VA Potential miVA 5'    GACAACGGGGGAGUGCUCCUU     3' (SEQ ID NO.: 116)
5'    ACAACGGGGGAGUGCUCCUUU    3' (SEQ ID NO.: 117)
5'    AACGGGGGAGUGCUCCUUUUU    3' (SEQ ID NO.: 118)

FIG. 16
Target Cleavage is Directed by VA RNA1
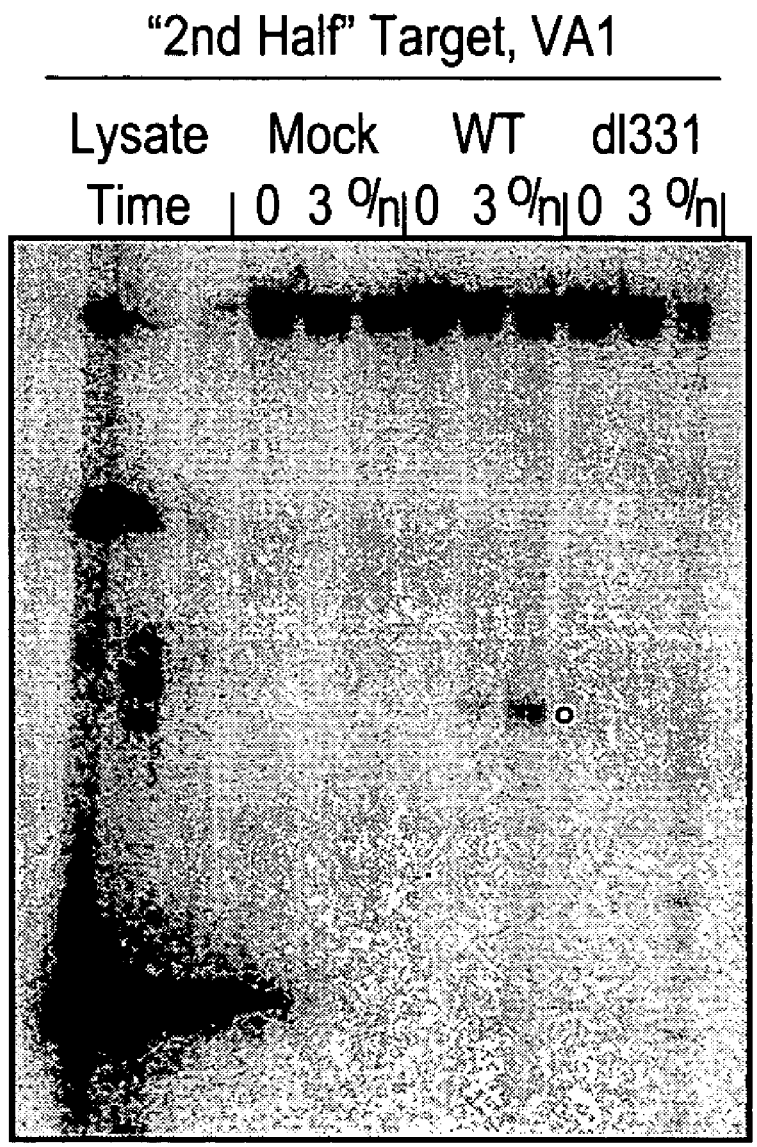
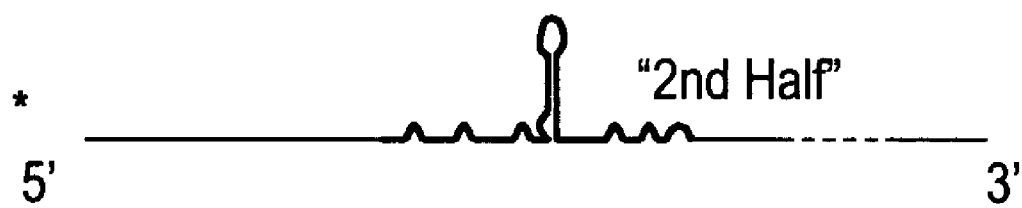

FIG. 17
Accumulation of VA RNA1 and miVA1 in Infected Cells
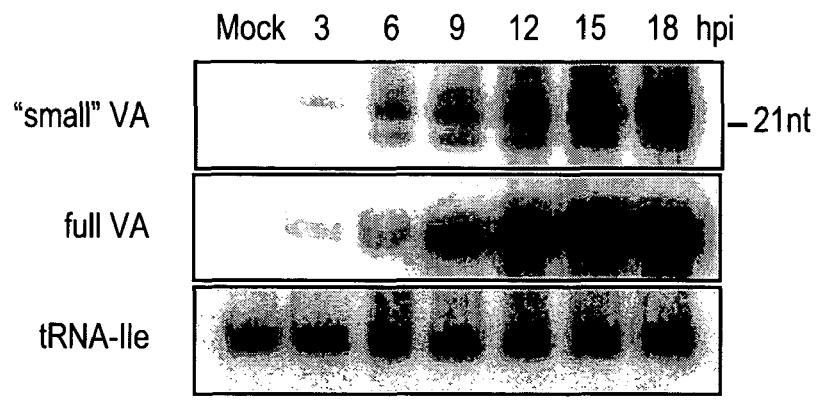
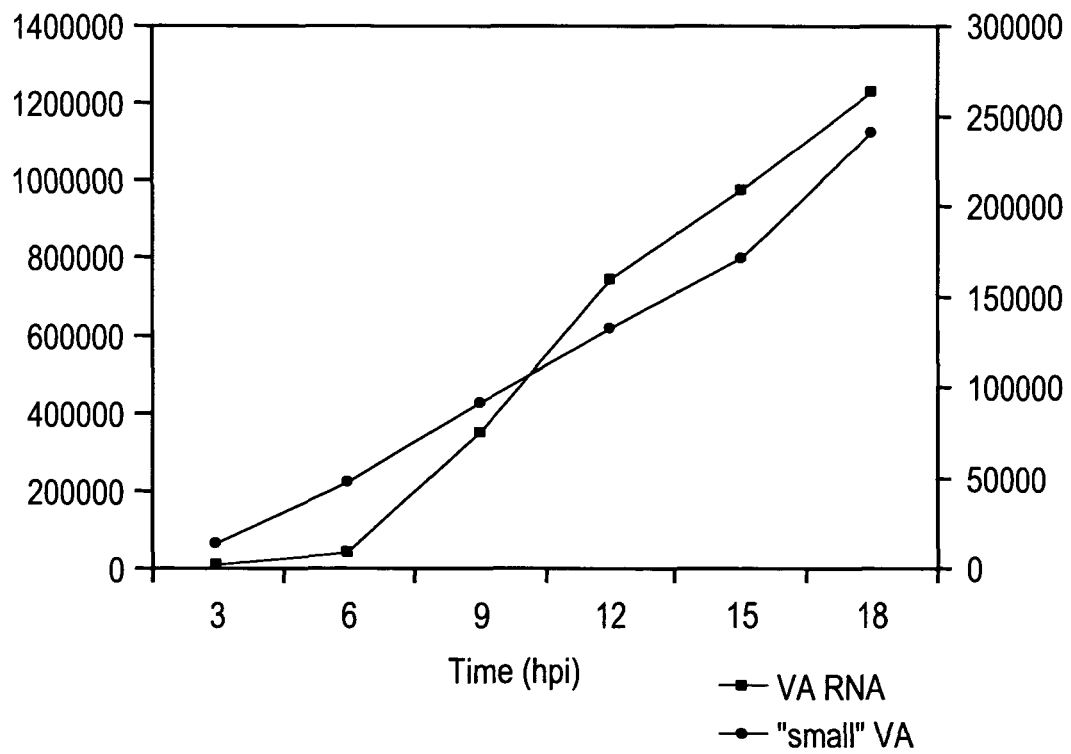

Processing of VA RNA2 in Fly Extracts and
With Recombinant Human Dicer

SEQUENCE LISTING

<160> NUMBER OF SEQ ID NOS: 119

<210> SEQ ID NO 1
<211> LENGTH: 161
<212> TYPE: RNA
<213> ORGANISM: Human adenovirus type 17

<400> SEQUENCE: 1

```
ggcucuuccu ccguagccug gcggaacgca aacggguuag gccgcgcgug uaccccgguu      60
cgaguccccu cgaaucaggc uggagccgcg acuaacgugg uauuggcacu cccgucucga     120
cccgagcccg auagccgcca ggauacgcgg gaagagcccu u                         161
```

<210> SEQ ID NO 2
<211> LENGTH: 150
<212> TYPE: RNA
<213> ORGANISM: Human adenovirus type 17

<400> SEQUENCE: 2

```
ggcucgcgcc cguagucugg agaagcaucg ccaggguuga gucgcggcag aacccgguuc      60
gcggacggcc gcggcgagcg ggacuugguc accccgccga uuuaaagacc cacagccagc     120
cgacuucucc aguuacggga gcgagcccc                                        150
```

<210> SEQ ID NO 3
<211> LENGTH: 160
<212> TYPE: RNA
<213> ORGANISM: Human adenovirus type 25

<400> SEQUENCE: 3

```
ggcucgacuc cguggccugg aggcuaagcg aacggguugg gcugcgcgug uaccccgguu      60
cgaaucucga aucaggcugg agccgcagcu aacgugguau uggcacuccc gucumgaccc     120
aagcbugcac caacccucca ggauacggag gcgggucguu                            160
```

```
<210> SEQ ID NO 4
<211> LENGTH: 159
<212> TYPE: RNA
<213> ORGANISM: Human adenovirus type 25

<400> SEQUENCE: 4
ggcucgucug ccguagucug gagaagaauc gccaggguug cguugcggug ugccccgguu      60
cgaggccggc cggauuccgc ggcuaacgag ggcguggcug ccccgucguu uccaagaccc     120
cauagccagc cgacuucucc aguuacgag cgagccccu                            159

<210> SEQ ID NO 5
<211> LENGTH: 159
<212> TYPE: RNA
<213> ORGANISM: Human adenovirus type 11

<400> SEQUENCE: 5
gacucgacuc cguagccugg aggaacguga acggguuggg ucgcggugua ccccgguucg      60
agacuuguac ucgagccggc cggagccgcg gcuaacgugg uauuggcacu cccgucucga    120
cccagccuac aaaaauccag gauacggaau cgagucguu                           159

<210> SEQ ID NO 6
<211> LENGTH: 172
<212> TYPE: RNA
<213> ORGANISM: Human adenovirus type 41

<400> SEQUENCE: 6
gacucuucuc cguagccugg aggauagacc gccaggguge ggugcgaac aaccccceggu      60 ucgagaccgg cuggauccgc cacucccgac gcgccggccc cguguccacg acggaaaccc    120
cgccgagacc uagccgcggu ccccggaucu ccagauacgg aggggagucu uu             172

<210> SEQ ID NO 7
<211> LENGTH: 172
<212> TYPE: RNA
<213> ORGANISM: Human adenovirus type 40

<400> SEQUENCE: 7
gacuuuccuc cguagccugg gggacagacc gccaggguge aguggcaaac aaccccceggu     60 ucgagaccgg cuggaucugc cacucccgac gcgccggccg ugcguccacg acggaaaccc    120
cgccgagacc uagccgcggu ccauggaucu ccagauacgg aggggagucu uu             172

<210> SEQ ID NO 8
<211> LENGTH: 172
<212> TYPE: RNA
<213> ORGANISM: Human adenovirus type 40

<400> SEQUENCE: 8
gacuuuccuc cguagccugg aggacagacc gccaggguge aguggcaaac aaccccceggu     60 ucgagaccgg cuggaucugc cacucccgac gcgccggccg ugcguccacg acggaaaccc    120
cgccgagacc uagccgcggu cccuggaucu ccagauacgg aggggagucu uu             172

<210> SEQ ID NO 9
<211> LENGTH: 172
<212> TYPE: RNA
<213> ORGANISM: Human adenovirus type 40

<400> SEQUENCE: 9
gacuuuccuc cguagccugg aggacagacc gccaggguge aguggcaaac aaccccceggu     60
```

```
ucgagaccgg cuggaucugc cacucccgac gcgccggccg ugcguccacg acggaaaccc      120
cgccgagacc uagccgcggu cccuggaucu ccagauacgg aggggagucu uu              172

<210> SEQ ID NO 10
<211> LENGTH: 159
<212> TYPE: RNA
<213> ORGANISM: Human adenovirus type 11

<400> SEQUENCE: 10
gacucgacuc cguagccugg aggaacguga acggguuggg ucgcggugua ccccgguucg      60
agacuuguac ucgagccggc cggagccgcg gcuaacgugg uauuggcacu cccgucucga      120
cccagccuac aaaaauccag gauacggaau cgagucguu                            159

<210> SEQ ID NO 11
<211> LENGTH: 159
<212> TYPE: RNA
<213> ORGANISM: Human adenovirus type 14

<400> SEQUENCE: 11
gacucgacuc uguagccugg aggaacguga acggguuggg ucgcggugua ccccgguuca      60
agacuuguac ucgagccggc cggagccgcg gcuaacgugg uauuggcacu cccgucucga      120
cccagccuac aaaaauccag gauacggaau cgagucguu                            159

<210> SEQ ID NO 12
<211> LENGTH: 160
<212> TYPE: RNA
<213> ORGANISM: Human adenovirus type 16

<400> SEQUENCE: 12
ggcucgucuc cguggccugg aggcuaagcg aacggguugg gcugcgcgug uaccccgguu      60
cgaaucucgg aucaggcugg agccgcagcu aacguggauc uggcacuccc gucucgaccc      120
aggccugcac aaaaccucca ggauacggag gcgggucguu                           160

<210> SEQ ID NO 13
<211> LENGTH: 171
<212> TYPE: RNA
<213> ORGANISM: Human adenovirus type 16

<400> SEQUENCE: 13
ggcucgcgcc cguagucugg agaaucaauc gccagggaug cguugcggug ugccccgguu      60
cgagucuuag cgcgcggauc ggccgguuuc cgcgacaagc gaggguuugg cagccucguc      120
auuucuaaga ccccgccagc cgacuucucc aguuuacggg agcgagcccu c              171

<210> SEQ ID NO 14
<211> LENGTH: 159
<212> TYPE: RNA
<213> ORGANISM: Human adenovirus type 19

<400> SEQUENCE: 14
ggcucuuccu ccguagccug gcggaacgaa acgguuuagg ucgcgugugu accccgguuc      60 gagucccuc gaaucaggcu ggagccgcga cuaacguggu auuggcacuc ccgucucgac      120
ccgagcccga uagccgccag gauacggcgg agagcccuu                            159

<210> SEQ ID NO 15
<211> LENGTH: 147
<212> TYPE: RNA
```

<213> ORGANISM: Human adenovirus type 19

<400> SEQUENCE: 15

| ggcucgcgcc cguagucugg agaagcaucg ccaggguuga gucgcggcag aacccgguuc | 60 |
| gaggacggcc gcggcgagcg ggacuugguc accccgccga uuuaaagacc cacagccagc | 120 |
| cgacuucucc aguuacggga gcgagcc | 147 |

<210> SEQ ID NO 16
<211> LENGTH: 159
<212> TYPE: RNA
<213> ORGANISM: Human adenovirus type 34

<400> SEQUENCE: 16

| gacucgacuc cguagccugg aggaacguga acggguuggg ucgcggugua ccccgguucg | 60 |
| agacuuguac ucgagccggc cggagccgcg gcuaacgugg uauuggcacu cccgucucga | 120 |
| cccagccuac aaaaauccag gauacggaau cgagucguu | 159 |

<210> SEQ ID NO 17
<211> LENGTH: 159
<212> TYPE: RNA
<213> ORGANISM: Human adenovirus type 35

<400> SEQUENCE: 17

| gacucgacuc cguagccugg aggaacguga acgggguggg ucgcggugua ccccgguucg | 60 |
| agacuuguac ucgagccggc cggagccgcg gcuaacgugg uauuggcacu cccgucucga | 120 |
| cccagccuac aaaaauccag gauacggaau cgagucguu | 159 |

<210> SEQ ID NO 18
<211> LENGTH: 159
<212> TYPE: RNA
<213> ORGANISM: Human adenovirus type 37

<400> SEQUENCE: 18

| ggcucuuccu ccguagccug gcggaacgaa acgggguuagg ccgcgugugu acccgguuc | 60 |
| gagucccuc gaaucaggcu ggagccgcga cuaacguggu auuggcacuc ccgucucgac | 120 |
| ccaagcccga uagccgccag gauacggcgg agagcccuu | 159 |

<210> SEQ ID NO 19
<211> LENGTH: 150
<212> TYPE: RNA
<213> ORGANISM: Human adenovirus type 37

<400> SEQUENCE: 19

| ggcucgcgcc cguagucugg agaagcaucg ccaggguuga gucgcggcag aacccgguuc | 60 |
| aaggacggcc gcggcgagcg ggacuugguc accccgccga uuuaaagacc cacagccagc | 120 |
| cgacuucucc aguuacggga gcgagccccc | 150 |

<210> SEQ ID NO 20
<211> LENGTH: 172
<212> TYPE: RNA
<213> ORGANISM: Human adenovirus type 3

<400> SEQUENCE: 20

| ggcucgacuc cguggucugg gggaacguga acgggguggg ucgcggugua ccccgguucg | 60 |
| aguccaaagc uaagcgauca cgcucggauc ggcggagcc gcggcuaacg ugguauuggc | 120 |
| uaucccgucu cgacccagcc gacgaauauc cagggguacgg aguagagucg uu | 172 |

<210> SEQ ID NO 21
<211> LENGTH: 173
<212> TYPE: RNA
<213> ORGANISM: Human adenovirus type 3

<400> SEQUENCE: 21

```
ggcucgcgcc cguagucugg agaaucaguc gccaggguug cguugcggua ugccccgguu    60
ggagccuaag cgcggcucgu aucggccggu uccgcgaca agcaggguuu ggcagccccg    120
uuauuuccaa gaccccgcca gccgacuucu ccaguuuacg ggagcgagcc cuu          173
```

<210> SEQ ID NO 22
<211> LENGTH: 145
<212> TYPE: RNA
<213> ORGANISM: Human adenovirus type 4a

<400> SEQUENCE: 22

```
gguccaaaaa aaagcuagua agcacggaaa gcggccgacc gcaauggcuc gcugccagau    60
uucgcagcua acgagggcgu ggcuguccccg ucguuccaa gaccccauaa gccagccaac    120
uucuccaguu acggagcgag cccuc                                        145
```

<210> SEQ ID NO 23
<211> LENGTH: 160
<212> TYPE: RNA
<213> ORGANISM: Human adenovirus type 4a

<400> SEQUENCE: 23

```
ggcucgacuc cguggccugg aggcuaagca acgggguugg gcugcgcgug uaccccgguu    60
cgaaucucga aucaggcugg agccgcagcu aacguggguac uggcacuccc gucucgaccc   120
aggccugcac aaaaccucca ggauacggag gcgggucguu                         160
```

<210> SEQ ID NO 24
<211> LENGTH: 160
<212> TYPE: RNA
<213> ORGANISM: Human adenovirus type 4

<400> SEQUENCE: 24

```
ggcucgacuc cguggccugg aggcuaagcg aacgggguugg gcugcgcgug uaccccgguu    60
cgaaucucga aucaggcugg agccgcagcu aacguggguac uggcacuccc gucucgaccc   120
aggccugcac aaaaccucca ggauacggag gcgggucguu                         160
```

<210> SEQ ID NO 25
<211> LENGTH: 168
<212> TYPE: RNA
<213> ORGANISM: Human adenovirus type 4

<400> SEQUENCE: 25

```
ggcucacugc cguagauugg agaagaaucg ccaggguugc guugcggugu gccccgguuc    60
gagaccgcuc ggguucggccg aauuccgcgg cuaacgaggg cguggcugcc ccgucguuuc   120 caagaccccca uaagccagcc gacuucucca guuacggagc gagccccu               168
```

<210> SEQ ID NO 26
<211> LENGTH: 110
<212> TYPE: RNA
<213> ORGANISM: Human adenovirus type 2

<400> SEQUENCE: 26

```
agcgggcacu cuuccguggu cugguggaua aauucgcaag gguaucaugg cggacgaccg      60
ggguucgaac cccggauccg ccguccgcc gugauccaug cgguuaccgc               110

<210> SEQ ID NO 27
<211> LENGTH: 158
<212> TYPE: RNA
<213> ORGANISM: Human adenovirus type 2

<400> SEQUENCE: 27
ggcucgcucc cuguagccgg aggguuauuu uccaaggguu gagucgcagg accccgguu      60 cgagucucgg gccggccgga cugcggcgaa cggggguuug ccuccccguc augcaagacc     120
ccgcuugcaa auuccuccgg aaacagggac gagccccu                            158

<210> SEQ ID NO 28
<211> LENGTH: 162
<212> TYPE: RNA
<213> ORGANISM: Human adenovirus type 5

<400> SEQUENCE: 28
agcgggcacu cuuccguggu cugguggaua aauucgcaag gguaucaugg cggacgaccg      60
ggguucgagc cccguauccg ccguccgcc gugauccaug cgguuaccgc ccgcgucg       120 aacccaggug ugcgacguca gacaacgggg gagugcuccu uu                       162

<210> SEQ ID NO 29
<211> LENGTH: 161
<212> TYPE: RNA
<213> ORGANISM: Human adenovirus type 5

<400> SEQUENCE: 29
uggcucgcuc ccuguagccg gaggguuauu uuccaagggu ugagucgcgg gaccccggu      60 ucgagucucg gaccggccgg acugcggcga acgggguuu gccucccgu caugcaagac     120 cccgcuugca auuccuccg gaaacaggga cgagcccccuu u                       161

<210> SEQ ID NO 30
<211> LENGTH: 159
<212> TYPE: RNA
<213> ORGANISM: Human adenovirus type 8

<400> SEQUENCE: 30
ggcucuuccu ccguagccug gcggaacgaa acggguuagg ccgcgcgugu acccccgguuc     60 gagucccuc gaaucaggcu aaagccgcga cuaacguggu auuggcacuc ccgucucgac     120
ccaagcccga uagccgccag gauacggguga agagccuuu                          159

<210> SEQ ID NO 31
<211> LENGTH: 150
<212> TYPE: RNA
<213> ORGANISM: Human adenovirus type 8

<400> SEQUENCE: 31
ggcucgcgcc cguagucugg acaagcauca cuagggguuaa guuacagcag aacccgguuc     60
gcggacggcc gcggcaagcg ggacuuaguu accccgccaa uuuaaagacc cgcagccagc    120
cgacuuuucc aguuacggga gcgagccccc                                     150

<210> SEQ ID NO 32
<211> LENGTH: 161
<212> TYPE: RNA
<213> ORGANISM: Human adenovirus type 23
```

<400> SEQUENCE: 32
ggcucgacuc cguggccugg agcuaagcga acggguuggg cugcgcgugu accccgguuc        60
gaaucucgaa ucaggcugga gccacagcua acgugguacu ggcaccccg ucucgaccca        120 agccugcuaa cgaaaccucc aggauacgga ggcgggucgu u                            161

<210> SEQ ID NO 33
<211> LENGTH: 172
<212> TYPE: RNA
<213> ORGANISM: Human adenovirus type 23

<400> SEQUENCE: 33
ggcucgcugc cguagucugg agaaagaauc gccaggguug cguugcggug ugccccgguu        60
cgagccucag cgcucggcgc cggccggauu ccgcggcuaa cguggcgugg cugccccguc        120
guuuccaaga ccccuuagcc agccgacuuc uccaguuacg gagcgagccc cu                172

<210> SEQ ID NO 34
<211> LENGTH: 172
<212> TYPE: RNA
<213> ORGANISM: Human adenovirus type 3

<400> SEQUENCE: 34
ggcucgacuc cguggucugg gggaacguga acggguuggg ucgcggugua ccccgguucg        60
aguccaaagc uaagcgauca cgcucggauc ggccggagcc gcggcuaacg ugguauuggc        120
uaucccgucu cgacccagcc gacgaauauc caggguacgg aguagagucg uu                172

<210> SEQ ID NO 35
<211> LENGTH: 174
<212> TYPE: RNA
<213> ORGANISM: Human adenovirus type 3

<400> SEQUENCE: 35
ggcucgcgcc cguagucugg agaaucaguc gccaggguug cguugcggua ugccccgguu        60
ggagccuaag cgcggcucgu aucggccggu uccgcgacaa gcgaggguu uggcagcccc        120 guuauuucca agaccccgcc agccgacuuc uccaguuuac gggagcgagc ccuu              174

<210> SEQ ID NO 36
<211> LENGTH: 160
<212> TYPE: RNA
<213> ORGANISM: Human adenovirus type 4

<400> SEQUENCE: 36
ggcucgacuc cguggccugg aggcuaagcg aacggguugg gcugcgcgug uaccccgguu        60
cgaaucucga aucaggcugg agccgcagcu aacgugguac uggcacuccc gucucgaccc        120
aggccugcac aaaaccucca ggauacggag gcgggucguu                              160

<210> SEQ ID NO 37
<211> LENGTH: 168
<212> TYPE: RNA
<213> ORGANISM: Human adenovirus type 4

<400> SEQUENCE: 37
ggcucacugc cguagauugg agaagaaucg ccaggguugc guugcggugu gccccgguuc        60
gagaccgcuc ggguccggcc gaauuccgcg cuaacgaggg cguggcugcc ccgucguuuc        120
caagacccca uaagccagcc gacuucucca guuacggagc gagcccuu                     168

```
<210> SEQ ID NO 38
<211> LENGTH: 160
<212> TYPE: RNA
<213> ORGANISM: Human adenovirus type 9

<400> SEQUENCE: 38
ggcucuuccu ccguagccug gcggaacgca aacggguuag gccgcgugug uaccccgguu      60
cgaguccccu ugaaucaggc uggagccgcg acuaacgugg uauuggcacu cccgucucga    120
cccgagcccg auagccgcca ggauacggcg gagaguccuu                          160

<210> SEQ ID NO 39
<211> LENGTH: 150
<212> TYPE: RNA
<213> ORGANISM: Human adenovirus type 9

<400> SEQUENCE: 39
ggcucgcgcc cguagucugg agaagcaucg ccaggguuga gucgcggcag aacccgguuc     60
gcggacggcc gcggcgagcg ggacuugguc accccgccga uuuaaagacc cacagccagc   120
cgacuucucc aguuacggga gcgagccccc                                    150

<210> SEQ ID NO 40
<211> LENGTH: 160
<212> TYPE: RNA
<213> ORGANISM: Human adenovirus type 13

<400> SEQUENCE: 40
ggcucuuccu ccguagccug gcggaacgca aacggguuag gccgcgcgug uaccccgguu     60
cgaguccccu cgaaucaggc uggagccgcg acuaacgugg uauuggcacu cccgucucga   120
cccgagcccg auagccgcca ggauacggcg gagagcccuu                         160

<210> SEQ ID NO 41
<211> LENGTH: 150
<212> TYPE: RNA
<213> ORGANISM: Human adenovirus type 13

<400> SEQUENCE: 41
ggcucgcgcc cguagucugg agaagcaucg ccaggguuga gucgcggcag aacccgguuc     60
gcggacggcc gcggcgagcg ggaauugguc accccgccua uuuaaagacc cacagccagc   120
cgacuucucc aguuacggga gcgagccccc                                    150

<210> SEQ ID NO 42
<211> LENGTH: 160
<212> TYPE: RNA
<213> ORGANISM: Human adenovirus type 15

<400> SEQUENCE: 42
ggcucuuccu ccguagccug gcggaacgca aacggguuag gccgcgugug uaccccgguu     60
cgaguccccu cgaaucaggc uggagccgcg acuaacgugg uauuggcacu cccgucucga   120
cccaagcccg auagccgcca ggauacggcg gagagcccuu                         160

<210> SEQ ID NO 43
<211> LENGTH: 150
<212> TYPE: RNA
<213> ORGANISM: Human adenovirus type 15

<400> SEQUENCE: 43
ggcucgcgcc cguagucugg agaagcaucg ccaggguuga gucgcggcag aacccgguuc     60
```

```
gcggacggcc gcggcgagcg ggacuugguc accccgccga uuuaaagacc cacagccagc    120
cgacuucucc aguuacggga gcgagccccc                                      150

<210> SEQ ID NO 44
<211> LENGTH: 160
<212> TYPE: RNA
<213> ORGANISM: Human adenovirus type 17

<400> SEQUENCE: 44
ggcucuuccu ccguagccug gcggaacgca aacggguuag gccgcgcgug uaccccgguu    60
cgaguccccu cgaaucaggc uggagccgcg acuaacgugg uauuggcacu cccgucucga   120
cccgagcccg auagccgcca ggauacggcg gagagcccuu                          160

<210> SEQ ID NO 45
<211> LENGTH: 150
<212> TYPE: RNA
<213> ORGANISM: Human adenovirus type 17

<400> SEQUENCE: 45
ggcucgcgcc cguagucugg agaagcaucg ccaggguuga gucgcggcag aacccgguuc    60
gcggacggcc gcggcgagcg ggacuugguc accccgccga uuuaaagacc cacagccagc   120
cgacuucucc aguuacggga gcgagccccc                                     150

<210> SEQ ID NO 46
<211> LENGTH: 160
<212> TYPE: RNA
<213> ORGANISM: Human adenovirus type 19

<400> SEQUENCE: 46
ggcucuuccu ccguagccug gcggaacgca aacggguuag gucgcgugug uaccccgguu    60
cgaguccccu cgaaucaggc uggagccgcg acuaacgugg uauuggcacu cccgucucga   120
cccgagcccg auagccgcca ggauacggcg gagagcccuu                          160

<210> SEQ ID NO 47
<211> LENGTH: 150
<212> TYPE: RNA
<213> ORGANISM: Human adenovirus type 19

<400> SEQUENCE: 47
ggcucgcgcc cguagucugg agaagcaucg ccaggguuga gucgcggcag aacccgguuc    60
gaggacggcc gcggcgagcg ggacuugguc accccgccga uuuaaagacc cacagccagc   120
cgacuucucc aguuacggga gcgagccccc                                     150

<210> SEQ ID NO 48
<211> LENGTH: 160
<212> TYPE: RNA
<213> ORGANISM: Human adenovirus type 20

<400> SEQUENCE: 48
ggcucuuccu ccguagccug gcggaacgca aacggguuag gccgcgugug uaccccgguu    60
cgaguccccu cgaaucaggc uggagccgcg acuaacgugg uauuggcacu cccgucucga   120
cccaagcccg auagccgcca ggauacggcg gagagcccuu                          160

<210> SEQ ID NO 49
<211> LENGTH: 150
<212> TYPE: RNA
```

<213> ORGANISM: Human adenovirus type 20

<400> SEQUENCE: 49

| | | |
|---|---|---|
| ggcucgcgcc cguagucugg agaagcaucg ccaggguuga gucgcggcag aacccgguuc | 60 |
| gcggacggcc gcggcgagcg ggacuugguc accccgccga uuuaaagacc cacagccagc | 120 |
| cgacuucucc aguuacggga gcgagccccc | 150 |

<210> SEQ ID NO 50
<211> LENGTH: 160
<212> TYPE: RNA
<213> ORGANISM: Human adenovirus type 22

<400> SEQUENCE: 50

| | |
|---|---|
| ggcucuuccu ccguagccug gcggaacgca aacggguuag gccgcgugug uaccccgguu | 60 |
| cgaguccccu cgaaucaggc uggagccgcg acuaacgugg uauuggcacu cccgucucga | 120 |
| cccaagcccg auagccgcca ggauacggcg gagagcccuu | 160 |

<210> SEQ ID NO 51
<211> LENGTH: 150
<212> TYPE: RNA
<213> ORGANISM: Human adenovirus type 22

<400> SEQUENCE: 51

| | |
|---|---|
| ggcucgcgcc cguagucugg agaagcaucg ccaggguuga gucgcggcag aacccgguuc | 60 |
| aaggacggcc gcggcaagcg ggacuugguc accccgccga uuuaaagacc cacagccagc | 120 |
| cgacuucucc aguuacggga gcgagccccc | 150 |

<210> SEQ ID NO 52
<211> LENGTH: 160
<212> TYPE: RNA
<213> ORGANISM: Human adenovirus type 23

<400> SEQUENCE: 52

| | |
|---|---|
| ggcucuuccu ccguagccug gcggaacgca aacggguuag gccgcgugug uaccccgguu | 60 |
| cgaauccccu cgaaucaggc uggagccgcg acuaacgugg uauuggcacu cccgucucga | 120 |
| cccgagcccg auagccgcca ggauacggcg gagagcccuu | 160 |

<210> SEQ ID NO 53
<211> LENGTH: 150
<212> TYPE: RNA
<213> ORGANISM: Human adenovirus type 23

<400> SEQUENCE: 53

| | |
|---|---|
| ggcucgcgcc cguagucugg agaagcaucg ccaggguuga gucgcggcag aacccgguuc | 60 |
| gcggacggcc gcggcgagcg ggacuugguc accccgccga uuuaaagacc cacagccagc | 120 |
| cgacuucucc aguuacggga gcgagccccc | 150 |

<210> SEQ ID NO 54
<211> LENGTH: 160
<212> TYPE: RNA
<213> ORGANISM: Human adenovirus type 24

<400> SEQUENCE: 54

| | |
|---|---|
| ggcucuuccu ccguagccug gcggaacgca aacggguuag gccgcgugug uaccccgguu | 60 |
| cgaguccccu cgaaucaggc uggagccgcg acuaacgugg uauuggcacu cccgucucga | 120 |
| cccgagcccg auagccgcca ggauacggcg gagagcccuu | 160 |

<210> SEQ ID NO 55
<211> LENGTH: 150
<212> TYPE: RNA
<213> ORGANISM: Human adenovirus type 24

<400> SEQUENCE: 55

```
ggcucgcgcc cguagucugg agaagcuuug ccaggguuga gucgcggcag aacccgguuc    60
gcggacggcc gcggcgagcg ggacuugguc accccgccga uuuaaagacc cacagccagc   120
cgacuucucc aguuacggga gcgagccccc                                    150
```

<210> SEQ ID NO 56
<211> LENGTH: 160
<212> TYPE: RNA
<213> ORGANISM: Human adenovirus type 25

<400> SEQUENCE: 56

```
ggcucuuccu ccguagccug gcggaacgca aacgggguuag gccgcgugug uaccccgguu    60
cgaguccccu cgaaucaggc uggagccgcg acuaacgugg uauuggcacu cccgucucga   120
cccgagcccg auagccgcca ggauacggcg gagagcccuu                         160
```

<210> SEQ ID NO 57
<211> LENGTH: 150
<212> TYPE: RNA
<213> ORGANISM: Human adenovirus type 25

<400> SEQUENCE: 57

```
ggcucgcgcc cguagucugg agaagcaucg ccaggguuga gucgcggcag aacccgguuc    60
gaggacggcc gcggcgagcg ggacuugguc accccgccga uauaaagacc cacagccagc   120
cgacuucucc aguuacggga gcgagccccc                                    150
```

<210> SEQ ID NO 58
<211> LENGTH: 160
<212> TYPE: RNA
<213> ORGANISM: Human adenovirus type 26

<400> SEQUENCE: 58

```
ggcucuuccu ccguagccug gcggaacgca aacgggguuag gccgcgugug uaccccgguu    60
cgaguccccu cgaaucaggc uggagccgcg acuaacgugg uauuggcacu cccgucucga   120
cccgagcccg auagccgcca ggauacggcg gagagcccuu                         160
```

<210> SEQ ID NO 59
<211> LENGTH: 150
<212> TYPE: RNA
<213> ORGANISM: Human adenovirus type 26

<400> SEQUENCE: 59

```
ggcucgcgcc cguagucugg agaagcaucg ccaggguuga gucgcggcag aacccgguuc    60
gaggacggcc gcggcgagcg ggacuugguc accccgccga uauaaagacc cacagccagc   120
cgacuucucc aguuacggga gcgagccccc                                    150
```

<210> SEQ ID NO 60
<211> LENGTH: 160
<212> TYPE: RNA
<213> ORGANISM: Human adenovirus type 27

<400> SEQUENCE: 60

-continued

```
ggcucuuccu ccguagccug gcggaacgca aacggguuag gccgcgugug uaccccgguu    60
cgaguccccu cgaaucaggc uggagccgcg acuaacgugg uauuggcacu cccgucucga   120
cccgagcccg auagccgcca ggauacggcg gagagcccuu                         160

<210> SEQ ID NO 61
<211> LENGTH: 150
<212> TYPE: RNA
<213> ORGANISM: Human adenovirus type 27

<400> SEQUENCE: 61
ggcucgcgcc cguagucugg agaagcaucg ccaggguuga gucgcggcag aacccgguuc    60
gaggacggcc gcggcgagcg ggacuugguc accccgccga uuuaaagacc cacagccagc   120
cgacuucucc aguuacggga gcgagccccc                                    150

<210> SEQ ID NO 62
<211> LENGTH: 160
<212> TYPE: RNA
<213> ORGANISM: Human adenovirus type 28

<400> SEQUENCE: 62
ggcucuuccu ccguagccug gcggaacgca aacggguuag gccgcgugug uaccccgguu    60
cgaguccccu cgaaucaggc uggagccgcg acuaacgugg uauuggcacu cccgucucga   120
cccgagcccg auagccgcca ggauacggcg gagagcccuu                         160

<210> SEQ ID NO 63
<211> LENGTH: 150
<212> TYPE: RNA
<213> ORGANISM: Human adenovirus type 28

<400> SEQUENCE: 63
ggcucgcgcc cguagucugg agaagcaucg ccaggguuga gucgcggcag aacccgguuc    60
gcggacggcc gcggcgagcg ggacuugguc accccgccga uuuaaagacc cacagccagc   120
cgacuucucc aguuacggga gcgagccccc                                    150

<210> SEQ ID NO 64
<211> LENGTH: 160
<212> TYPE: RNA
<213> ORGANISM: Human adenovirus type 29

<400> SEQUENCE: 64
ggcucuuccu ccguagccug gcggaacgca aacggguuag gccgcgugug uaccccgguu    60
cgaguccccu cgaaucaggc uggagccgcg acuaacgugg uauuggcacu cccgucucga   120
cccgagcccg auagccgcca ggauacggcg gagagcccuu                         160

<210> SEQ ID NO 65
<211> LENGTH: 150
<212> TYPE: RNA
<213> ORGANISM: Human adenovirus type 29

<400> SEQUENCE: 65
ggcucgcgcc cguagucugg agaagcaucg ccaggguuga gucgcggcag aacccgguuc    60
gaggacggcc gcggcgagcg ggacuugguc accccgccga uuuaaagacc cacagccagc   120
cgacuucucc aguuacggga gcgagccccc                                    150

<210> SEQ ID NO 66
<211> LENGTH: 160
```

```
<212> TYPE: RNA
<213> ORGANISM: Human adenovirus type 30

<400> SEQUENCE: 66
ggcucuuccu ccguagccug gcggaacgca aacggguuag gccgcgugug uaccccgguu      60
cgaguccccu cgaaucaggc uggagccgcg acuaacgugg uauuggcacu cccgucucga     120
cccgagcccg auagccgcca ggauacggcg gagagcccuu                            160

<210> SEQ ID NO 67
<211> LENGTH: 150
<212> TYPE: RNA
<213> ORGANISM: Human adenovirus type 30

<400> SEQUENCE: 67
ggcucgcgcc cguagucugg agaagcaucg ccagggduuga gucgcggcag aacccgguuc     60
gcggacggcc gcggcgagcg ggacuugguc accccgccga uuuaaagacc cacagccagc    120
cgacuucucc aguuacggga gcgagccccc                                     150

<210> SEQ ID NO 68
<211> LENGTH: 160
<212> TYPE: RNA
<213> ORGANISM: Human adenovirus type 32

<400> SEQUENCE: 68
ggcucuuccu ccguagccug gcggaacgca aacggguuag gccgcgugug uaccccgguu     60
cgaguccccu cgaaucaggc uggagccgcg acuaacgugg uauuggcacu cccgucucga    120
cccgagcccg auagccgcca ggauacggcg gagagcccuu                          160

<210> SEQ ID NO 69
<211> LENGTH: 150
<212> TYPE: RNA
<213> ORGANISM: Human adenovirus type 32

<400> SEQUENCE: 69
ggcucgcgcc cguagucugg agaagcaucg ccagggduuga gucgcggcag aacccgguuc    60
gaggacggcc gcggcgagcg ggacuugguc accccgccga uuuaaagacc cacagccagc   120
cgacuucucc aguuacggga gcgagccccc                                    150

<210> SEQ ID NO 70
<211> LENGTH: 160
<212> TYPE: RNA
<213> ORGANISM: Human adenovirus type 33

<400> SEQUENCE: 70
ggcucuuccu ccguagccug gcggaacgca aacggguuag gccgcgugug uaccccgguu    60
cgaguccccu cgaaucaggc uggagccgcg acuaacgugg uauuggcacu cccgucucga   120
cccgagcccg auagccgcca ggauacggcg gagagcccuu                          160

<210> SEQ ID NO 71
<211> LENGTH: 150
<212> TYPE: RNA
<213> ORGANISM: Human adenovirus type 33

<400> SEQUENCE: 71
ggcucgcgcc cguagucugg agaagcaucg ccagggduuga gucgcggcag aacccgguuc    60
gcggacggcc gcggcgagcg ggacuugguc accccgccga uuuaaagacc cacagccagc   120
```

```
cgacuucucc aguuacggga gcgagccccc                                        150
```

<210> SEQ ID NO 72
<211> LENGTH: 160
<212> TYPE: RNA
<213> ORGANISM: Human adenovirus type 37

<400> SEQUENCE: 72

```
ggcucuuccu ccguagccug gcggaacgca aacggguuag gccgcgugug uaccccgguu        60
cgaguccccu cgaaucaggc uggagccgcg acuaacgugg uauuggcacu cccgucucga       120
cccaagcccg auagccgcca ggauacggcg gagagcccuu                             160
```

<210> SEQ ID NO 73
<211> LENGTH: 150
<212> TYPE: RNA
<213> ORGANISM: Human adenovirus type 37

<400> SEQUENCE: 73

```
ggcucgcgcc cguagucugg agaagcaucg ccagggguuga gucgcggcag aacccgguuc       60
aaggacggcc gcggcgagcg ggacuugguc accccgccga uuuaaagacc cacagccagc      120
cgacuucucc aguuacggga gcgagccccc                                       150
```

<210> SEQ ID NO 74
<211> LENGTH: 160
<212> TYPE: RNA
<213> ORGANISM: Human adenovirus type 39

<400> SEQUENCE: 74

```
ggcucuuccu ccguagccug gcggaacgca aacggguuag gccgcgcgug uaccccgguu       60
cgaguccccu cgaaucaggc uggagccgcg acuaacgugg uauuggcacu cccgucucga      120
cccgagcccg auagccgcca ggauacggcg gagagcccuu                            160
```

<210> SEQ ID NO 75
<211> LENGTH: 150
<212> TYPE: RNA
<213> ORGANISM: Human adenovirus type 39

<400> SEQUENCE: 75

```
ggcucgcgcc cguagucugg agaagcaucg ccagggguuga gucgcggcag aacccgguuc      60
gaggacggcc gcggcgagcg ggacuugguc accccgccga uuuaaagacc cacagccagc     120
cgacuucucc aguuacggga gcgagccccc                                      150
```

<210> SEQ ID NO 76
<211> LENGTH: 160
<212> TYPE: RNA
<213> ORGANISM: Human adenovirus type 36

<400> SEQUENCE: 76

```
ggcucuuccu ccguagccug gcggaacgca aacggguuag gccgcgugug uaccccgguu       60
cgaguccccu cgaaucaggc uggagccgcg acuaacgugg uauuggcacu cccgucucga     120
cccgagcccg auagccgcca ggauacggcg gagagcccuu                           160
```

<210> SEQ ID NO 77
<211> LENGTH: 150
<212> TYPE: RNA
<213> ORGANISM: Human adenovirus type 36

<400> SEQUENCE: 77

```
ggcucgcgcc cguagucugg agaagcaucg ccaggguuga gucgcggcag aacccgguuc      60
gcggacggcc gcggcgagcg ggacuugguc accccgccga uuuaaagacc cacagccagc    120
cgacuucucc aguuacggga gcgagccccc                                      150

<210> SEQ ID NO 78
<211> LENGTH: 160
<212> TYPE: RNA
<213> ORGANISM: Human adenovirus type 42

<400> SEQUENCE: 78
ggcucuuccu ccguagccug gcggaacgca aacggguuag gccgcgugug uaccccgguu      60
cgaguccccu cgaaucaggc uggagccgcg acuaacgugg uauuggcacu cccgucucga    120
cccgagcccg auagccgcca ggauacggcg gagagcccuu                           160

<210> SEQ ID NO 79
<211> LENGTH: 150
<212> TYPE: RNA
<213> ORGANISM: Human adenovirus type 42

<400> SEQUENCE: 79
ggcucgcgcc cguagucugg agaagcaucg ccaggguuga gucgcggcag aacccgguuc      60
gcggacggcc gcggcgagcg ggacuugguc accccgccga uuuaaagacc cacagccagc    120
cgacuucucc aguuacggga gcgagccccc                                      150

<210> SEQ ID NO 80
<211> LENGTH: 160
<212> TYPE: RNA
<213> ORGANISM: Human adenovirus type 43

<400> SEQUENCE: 80
ggcucuuccu ccguagccug gcggaacgca aacggguuag gccgcgugug uaccccgguu      60
cgaguccccu cgaaucaggc uggagccgcg acuaacgugg uauuggcacu cccgucucga    120
cccgagcccg auagccgcca ggauacggcg gagagcccuu                           160

<210> SEQ ID NO 81
<211> LENGTH: 150
<212> TYPE: RNA
<213> ORGANISM: Human adenovirus type 43

<400> SEQUENCE: 81
ggcucgcgcc cguagucugg agaagcaucg ccaggguuga gucgcggcag aacccgguuc      60
gcggacggcc gcggcgagcg ggacuugguc accccgccga uuuaaagacc cacagccagc    120
cgacuucucc aguuacggga gcgagccccc                                      150

<210> SEQ ID NO 82
<211> LENGTH: 160
<212> TYPE: RNA
<213> ORGANISM: Human adenovirus type 44

<400> SEQUENCE: 82
ggcucuuccu ccguagccug gcggaacgca aacggguuag gccgcgugug uaccccgguu      60
cgaguccccu cgaaucaggc uggagccgcg acuaacgugg uauuggcacu cccgucucga    120
cccgagcccg auagccgcca ggauacggcg gagagcccuu                           160

<210> SEQ ID NO 83
```

```
<211> LENGTH: 150
<212> TYPE: RNA
<213> ORGANISM: Human adenovirus type 44

<400> SEQUENCE: 83
ggcucgcgcc cguagucugg agaagcaucg ccaggguuga gucgcggcag aacccgguuc    60
gaggacggcc gcggcgagcg ggacuugguc accccgccga uuuaaagacc cacagccagc   120
cgacuucucc aguuacggga gcgagccccc                                    150

<210> SEQ ID NO 84
<211> LENGTH: 160
<212> TYPE: RNA
<213> ORGANISM: Human adenovirus type 45

<400> SEQUENCE: 84
ggcucuuccu ccguagccug gcggaacgca aacggguuag gccgcgugug uaccccgguu    60
cgaguccccu cgaaucaggc uggagccgcg acuaacgugg uauuggcacu cccgucucga   120
cccgagcccg auagccgcca ggauacggcg gagagcccuu                         160

<210> SEQ ID NO 85
<211> LENGTH: 150
<212> TYPE: RNA
<213> ORGANISM: Human adenovirus type 45

<400> SEQUENCE: 85
ggcucgcgcc cguagucugg agaagcaucg ccaggguuga gucgcggcag aacccgguuc    60
gaggacggcc gcggcgagcg ggacuugguc accccgccga uuuaaagacc cacagccagc   120
cgacuucucc aguuacggga gcgagccccc                                    150

<210> SEQ ID NO 86
<211> LENGTH: 160
<212> TYPE: RNA
<213> ORGANISM: Human adenovirus type 46

<400> SEQUENCE: 86
ggcucuuccu ccguagccug gcggaacgca aacggguuag gccgcgugug uaccccgguu    60
cgaguccccu cgaaucaggc uggagccgcg acuaacgugg uauuggcacu cccgucucga   120
cccaagcccg auagccgcca ggauacggcg gagagcccuu                         160

<210> SEQ ID NO 87
<211> LENGTH: 150
<212> TYPE: RNA
<213> ORGANISM: Human adenovirus type 46

<400> SEQUENCE: 87
ggcucgcgcc cguagucugg agaagcaucg ccaggguuga gucgcggcag aacccgguuc    60
gaggacggcc gcggcgagcg ggacuugguc accccgccga uuuaaagacc cacagccagc   120
cgacuucucc aguuacggga gcgagccccc                                    150

<210> SEQ ID NO 88
<211> LENGTH: 160
<212> TYPE: RNA
<213> ORGANISM: Human adenovirus type 47

<400> SEQUENCE: 88
ggcucuuccu ccguagccug gcggaacgca aacggguuag gccgcgugug uaccccgguu    60
cgaguccccu cgaaucaggc uggagccgcg acuaacgugg uauuggcacu cccgucucga   120
```

```
cccgagcccg auagccgcca ggauacggcg gagagcccuu                    160

<210> SEQ ID NO 89
<211> LENGTH: 150
<212> TYPE: RNA
<213> ORGANISM: Human adenovirus type 47

<400> SEQUENCE: 89
ggcucgcgcc cguagucugg agaagcaucg ccagggguuga gucgcgacag aacccgguuc   60
gcggacggcc gcggcgagcg ggacuugguc accccgccga uuuaaagacc cacagccagc  120
cgacuucucc aguuacggga gcgagccccc                                    150

<210> SEQ ID NO 90
<211> LENGTH: 160
<212> TYPE: RNA
<213> ORGANISM: Human adenovirus type 38

<400> SEQUENCE: 90
ggcucuuccu ccguagccug gcggaacgca aacgggguuag gccgcgugug uaccccgguu   60
cgaguccccu cgaaucaggc uggagccgcg acuaacgugg uauuggcacu cccgucucga  120
cccgagcccg auagccgcca ggauacggcg gagagcccuu                         160

<210> SEQ ID NO 91
<211> LENGTH: 150
<212> TYPE: RNA
<213> ORGANISM: Human adenovirus type 38

<400> SEQUENCE: 91
ggcucgcgcc cguagucugg agaagcaucg ccagggguuga gucgcggcag aacccgguuc   60
gcggacggcc gcggcgagcg ggacuugguc accccgccga uuuaaagacc cacagccagc  120
cgacuucucc aguuacggga gcgagccccc                                    150

<210> SEQ ID NO 92
<211> LENGTH: 160
<212> TYPE: RNA
<213> ORGANISM: Human adenovirus type 8

<400> SEQUENCE: 92
ggcucuuccu ccguagccug gcggaacgca aacggguuag gccgcgcgug uaccccgguu    60
cgaguccccu cgaaucaggc uaaagccgcg acuaacgugg uauuggcacu cccgucucga  120
cccaagcccg auagccgcca ggauacggug aagagccuuu                         160

<210> SEQ ID NO 93
<211> LENGTH: 150
<212> TYPE: RNA
<213> ORGANISM: Human adenovirus type 8

<400> SEQUENCE: 93
ggcucgcgcc cguagucugg acaagcauca cuaggguuaa guuacagcag aacccgguuc    60
gcggacggcc gcggcaagcg ggacuuaguu accccgccaa uuuaaagacc cgcagccagc  120
cgacuuuucc aguuacggga gcgagccccc                                    150

<210> SEQ ID NO 94
<211> LENGTH: 160
<212> TYPE: RNA
<213> ORGANISM: Human adenovirus type 16
```

```
<400> SEQUENCE: 94
ggcucgucuc cguggccugg aggcuaagcg aacggguugg gcugcgcgug uaccccgguu      60
cgaaucucgg aucaggcugg agccgcagcu aacguggguac uggcacuccc gucucgaccc    120
aggccugcac aaaaccucca ggauacggag gcgggucguu                           160

<210> SEQ ID NO 95
<211> LENGTH: 172
<212> TYPE: RNA
<213> ORGANISM: Human adenovirus type 16

<400> SEQUENCE: 95
ggcucgcgcc cguagucugg agaaucaauc gccaggguug cguugcggug ugccccgguu      60
cgagucuuag cgcgccggau cggccgguuu ccgcgacaag cgaggguuug gcagcccgu     120 cauuucuaag accccgccag ccgacuucuc caguuuacgg gagcgagccc uc             172

<210> SEQ ID NO 96
<211> LENGTH: 160
<212> TYPE: RNA
<213> ORGANISM: Human adenovirus type 21

<400> SEQUENCE: 96
ggcucgucuc cguggccugg aggcuaagcg aacggguugg gcugcgcgug uaccccgguu      60
cgaaucucgg aucaggcugg agccgcagcu aacguggguac uggcacuccc gucucgaccc    120
aggccugcac aaaaccucca ggauacggag gcgggucguu                           160

<210> SEQ ID NO 97
<211> LENGTH: 172
<212> TYPE: RNA
<213> ORGANISM: Human adenovirus type 21

<400> SEQUENCE: 97
ggcucgcgcc cguagucugg agaaucaauc gccaggguug cguugcggug ugccccgguu      60
cgagucuuag cgcgccggau cggccgguuu ccgcgacaag cgaggguuug gcagcccgu     120 cauuucuaag accccgccag ccgacuucuc caguuuacgg gagcgagccc uc             172

<210> SEQ ID NO 98
<211> LENGTH: 160
<212> TYPE: RNA
<213> ORGANISM: Human adenovirus type 10

<400> SEQUENCE: 98
ggcucuuccu ccguagccug gcggaacgca aacggguuag gccgcgugug uaccccgguu      60
cgaguccccu cgaaucaggc uggagccgcg acuaacgugg uauuggcacu cccgucucga    120
cccgagcccg auagccgcca ggauacggcg gagagcccuu                           160

<210> SEQ ID NO 99
<211> LENGTH: 123
<212> TYPE: RNA
<213> ORGANISM: Human adenovirus type 10

<400> SEQUENCE: 99
ggcucgcgcc cguagucugg agaagcaucg ccaggguuga gucgcggcga gcgggacuug      60
gucaccccgc cgauuuaaag acccacagcc agccgacuuc uccaguuacg ggagcgagcc    120
ccc                                                                   123
```

<210> SEQ ID NO 100
<211> LENGTH: 159
<212> TYPE: RNA
<213> ORGANISM: Human adenovirus type 11

<400> SEQUENCE: 100
gacucgacuc cguagccugg aggaacguga acggguuggg ucgcggugua ccccgguucg      60
agacuuguac ucgagccggc cggagccgcg gcuaacgugg uauuggcacu cccgucucga     120
cccagccuac aaaaauccag gauacggaau cgagucguu                            159

<210> SEQ ID NO 101
<211> LENGTH: 159
<212> TYPE: RNA
<213> ORGANISM: Human adenovirus type 14

<400> SEQUENCE: 101
gacucgacuc uguagccugg aggaacguga acggguuggg ucgcggugua ccccgguuca      60
agacuuguac ucgagccggc cggagccgcg gcuaacgugg uauuggcacu cccgucucga     120
cccagccuac aaaaauccag gauacggaau cgagucguu                            159

<210> SEQ ID NO 102
<211> LENGTH: 159
<212> TYPE: RNA
<213> ORGANISM: Human adenovirus type 34

<400> SEQUENCE: 102
gacucgacuc cguagccugg aggaacguga acggguuggg ucgcggugua ccccgguucg      60
agacuuguac ucgagccggc cggagccgcg gcuaacgugg uauuggcacu cccgucucga     120
cccagccuac aaaaauccag gauacggaau cgagucguu                            159

<210> SEQ ID NO 103
<211> LENGTH: 159
<212> TYPE: RNA
<213> ORGANISM: Human adenovirus type 35

<400> SEQUENCE: 103
gacucgacuc cguagccugg aggaacguga acggguuggg ucgcggugua ccccgguucg      60
agacuuguac ucgagccggc cggagccgcg gcuaacgugg uauuggcacu cccgucucga     120
cccagccuac aaaaauccag gauacggaau cgagucguu                            159

<210> SEQ ID NO 104
<211> LENGTH: 172
<212> TYPE: RNA
<213> ORGANISM: Human adenovirus type 41

<400> SEQUENCE: 104
gacucuucuc cguagccugg aggauagacc gccagggugc ggguggcgaac aaccccccggu    60 ucgagaccgg cuggauccgc cacucccgac gcgccggccc cguguccacg acggaaaccc    120
cgccgagacc uagccgcggu ccccggaucu ccagauacgg aggggagauc uu            172

<210> SEQ ID NO 105
<211> LENGTH: 172
<212> TYPE: RNA
<213> ORGANISM: Human adenovirus type 7

<400> SEQUENCE: 105
ggcucgacuc cguggccugg gggaacguga acggguuggg ucgcggugua ccccgguucg      60

```
aguccaaagc uaagcaauca cacucggauc ggccggagcc gcggcuaacg ugguauuggc    120
uaucccgucu cgacccagcc gacgaauauc cagggu acgg aguagagucg uu           172

<210> SEQ ID NO 106
<211> LENGTH: 175
<212> TYPE: RNA
<213> ORGANISM: Human adenovirus type 7

<400> SEQUENCE: 106
ggcucgcgcc cguagucugg agaaucaguc gccaggguug cguugcggua ugccccggu     60 ucgagccuaa gcgcggcucg uaucggccgg uuuccgcgac aagcgagggu uuggcagccc    120
agucauuucc aagaccccgc cagccgacuu cuccaguuua cgggagcgag cccuu         175

<210> SEQ ID NO 107
<211> LENGTH: 172
<212> TYPE: RNA
<213> ORGANISM: Human adenovirus type 7

<400> SEQUENCE: 107
ggcucgacuc cguggccugg gggaacgugg acggguuggg ucgcggugua ccccgguucg    60
aguccaaagc uaagcaauca cacucggauc ggccggagcc gcggcuaacg ugguauuggc    120
uaucccgucu cgacccagcc gacgaauauc cagggu acgg aguagagucg uu           172

<210> SEQ ID NO 108
<211> LENGTH: 175
<212> TYPE: RNA
<213> ORGANISM: Human adenovirus type 7

<400> SEQUENCE: 108
ggcucgcgcc cguagucugg agaaucaguc gccaggguug cguugcggua ugccccggu     60 ucgagccuaa gcgcggcucg uaucggccgg uuuccgcgac aagcgagggu uuggcagccc    120
agucauuucc aagaccccgc cagccgacuu cuccaguuua cgggagcgag cccuu         175

<210> SEQ ID NO 109
<211> LENGTH: 75
<212> TYPE: RNA
<213> ORGANISM: C. elegans

<400> SEQUENCE: 109
guggcaucug agguaguaug uaauauugua gacugucuau aauguccaca auguuucaac    60
uaacucggcu guucu                                                    75

<210> SEQ ID NO 110
<211> LENGTH: 93
<212> TYPE: RNA
<213> ORGANISM: C. elegans

<400> SEQUENCE: 110
gugaccguac cgagcugcau acuuccuuac augcccauac uauaucauaa auggauaugg    60
aauguaaaga aguauguaga acggggugguu agu                                93

<210> SEQ ID NO 111
<211> LENGTH: 96
<212> TYPE: RNA
<213> ORGANISM: C. elegans

<400> SEQUENCE: 111
gagccagugu cuguucuugg cggauccauu uugggu ugua ccucauccua aauuugacgg    60
```
uacccguaau guuuccgcug agaaccgacu gugcac                                        96

<210> SEQ ID NO 112
<211> LENGTH: 159
<212> TYPE: RNA
<213> ORGANISM: Adenovirus Type 5 Virus Associated (VA) RNA I

<400> SEQUENCE: 112
gggcacucuu ccguggucug guggauaaau ucgcaagggu aucauggcgg acgaccgggg              60 uucgaaccccc ggauccggcc guccgccgug auccaugcgg uuaccgcccg cgugucgaac            120
ccaggugugc gacgucagac aacggggag cgcuccuuu                                    159

<210> SEQ ID NO 113
<211> LENGTH: 245
<212> TYPE: RNA
<213> ORGANISM: Karposi's Sarcoma-associated herpesvirus

<400> SEQUENCE: 113
uaauucuagc gcggcagacu ccuuuuccccg ccaagaacuu auagaccagg agaaagaacu             60
ccuugagaag uuggcguggc gaacagaggc agucuuagcg acggacguca cuuccuucuu            120
guuacuuaaa uugcugggg gcucccaaca ccuggacuuu uggcaccacg aggucaacac             180
ccugauuaca aaagccuuag uugacccaaa gacuggcuca uugcccgccu cuauuaucag            240
ccaug                                                                        245

<210> SEQ ID NO 114
<211> LENGTH: 34
<212> TYPE: DNA
<213> ORGANISM: Human adenovirus type 5

<400> SEQUENCE: 114
agggaaagga gcactccccc gttgtctgac gtcg                                         34

<210> SEQ ID NO 115
<211> LENGTH: 27
<212> TYPE: RNA
<213> ORGANISM: Human adenovirus type 5

<400> SEQUENCE: 115
cgucagacaa cgggggagug cuccuuu                                                 27

<210> SEQ ID NO 116
<211> LENGTH: 21
<212> TYPE: RNA
<213> ORGANISM: Human adenovirus type 5

<400> SEQUENCE: 116
gacaacgggg gagugcuccu u                                                       21

<210> SEQ ID NO 117
<211> LENGTH: 21
<212> TYPE: RNA
<213> ORGANISM: Human adenovirus type 5

<400> SEQUENCE: 117
acaacggggg agugcuccuu u                                                       21

<210> SEQ ID NO 118
<211> LENGTH: 21
<212> TYPE: RNA

```
-continued

<213> ORGANISM: Human adenovirus type 5

<400> SEQUENCE: 118
aacgggggag ugcuccuuuu u                                              21

<210> SEQ ID NO 119
<211> LENGTH: 234
<212> TYPE: RNA
<213> ORGANISM: Human Immunodeficiency Virus

<400> SEQUENCE: 119
aggagcuaug uuccuugggu ucuugggagc agcaggaagc acuaugggcg cagugucauu     60
gacgcugacg guacaggcca gacaauuauu gucugguaua gugcaacagc agaacaauuu    120
gcugagggcu auugaggcgc aacaacaucu guugcaacuc acagucuggg gcaucaagca    180
gcuccaggca agaguccugg cuguggaaag auaccuaagg gaucaacagc uccu          234
```

VIRALLY-ENCODED RNAS AS SUBSTRATES, INHIBITORS AND DELIVERY VEHICLES FOR RNAI

RELATED APPLICATIONS

This patent application claims the benefit of U.S. Provisional Patent Application Ser. No. 60/497,156, entitled "Virally-Encoded RNAs as Substrates, Inhibitors and Delivery Vehicles for RNAi", filed Aug. 22, 2003 and U.S. Provisional Patent Application Ser. No. 60/566,114, entitled "Virally-Encoded RNAs as Substrates, Inhibitors and Delivery Vehicles for RNAi", filed Apr. 27, 2004. The entire contents of the above-referenced provisional patent applications are incorporated herein by this reference.

BACKGROUND OF THE INVENTION

RNAs that do not function as messenger RNAs, transfer RNAs or ribosomal RNAs, are collectively termed non-coding RNAs (ncRNAs). ncRNAs can range in size from 21-25 nucleotides (nt) up to >10,000 nt, and estimates for the number of ncRNAs per genome range from hundreds to thousands. The functions of ncRNAs, although just beginning to be revealed, appear to vary widely from the purely structural to the purely regulatory, and include effects on transcription, translation, mRNA stability and chromatin structure (G. Storz, Science (2002) 296: 1260-1262). Two recent pivotal discoveries have placed ncRNAs in the spotlight: the identification of large numbers of very small ncRNAs of 20-24 nucleotides in length, termed micro RNAs (miRNAs), and the relationship of these miRNAs to intermediates in a eukaryotic RNA silencing mechanism known as RNA interference (RNAi).

RNA silencing refers to a group of sequence-specific, RNA-targeted gene-silencing mechanisms common to animals, plants, and some fungi, wherein RNA is used to target and destroy homologous mRNA, viral RNA, or other RNAs. RNA silencing was first observed in plants, where it was termed posttranscriptional gene silencing (PTGS). Researchers, trying to create more vividly purple flowers, introduced an extra copy of the gene conferring purple pigment. Surprisingly, the researchers discovered that the purple-conferring genes were switched off, or cosuppressed, producing white flowers. A similar phenomenon observed in Fungi was termed quelling. These phenomena were subsequently found to be related to a process in animals called RNA interference (RNAi). In RNAi, experimentally introduced double-stranded RNA (dsRNA) leads to loss of expression of the corresponding cellular gene. A key step in the molecular mechanism of RNAi is the processing of dsRNA by the ribonuclease Dicer into short dsRNAs, called small interfering RNAs (siRNAs), of ~21-23 nt in length and having specific features including 2 nt 3'-overhangs, a 5'-phosphate group and 3'-hydroxyl group. siRNAs are incorporated into a large nucleoprotein complex called RNA-induced silencing complex (RISC). A distinct ribonuclease component of RISC uses the sequence encoded by the antisense strand of the siRNA as a guide to find and then cleave mRNAs of complementary sequence. The cleaved mRNA is ultimately degraded by cellular exonucleases. Thus, in PTGS, quelling, and RNAi, the silenced gene is transcribed normally into mRNA, but the mRNA is destroyed as quickly as it is made. In plants, it appears that PTGS evolved as a defense strategy against viral pathogens and transposons. While the introduction of long dsRNAs into plants and invertebrates initiates specific gene silencing (3,4), in mammalian cells, long dsRNA induces the potent translational inhibitory effects of the interferon response (8). Short dsRNAs of <30 bp, however, evade the interferon response and are successfully incorporated into RISC to induce RNAi (9).

Another group of small ncRNAs, called micro RNAs (miRNAs), are related to the intermediates in RNAi and appear to be conserved from flies to humans (2, 12, 13). miRNAs are putatively transcribed first as a long transcript (pri-miRNAs), in some cases as miRNAs clusters, and these transcripts are then processed to ~70 nt RNA precursors (pre-miRNAs) having a predicted stem-loop structure. The enzyme Dicer cleaves the pre-miRNAs to produce ~20-24 nt miRNAs that function as single-stranded RNAi mediators (4, 10). These small transcripts have been proposed to play a role in development, apparently by suppressing target genes to which they have some degree of complementarity. The founding members of miRNAs, lin-4 and let-7, exert their control of gene expression by binding to non-identical sequences in the 3' UTR of mRNA, thereby preventing mRNA translation (17). In recent studies, however, miRNAs bearing perfect complementarity to a target RNA could function as siRNAs to specifically degrade the target sequences (14, 15). Thus, the degree of complementarity between an miRNA and its target may determine whether the miRNA acts as a translational repressor or as a guide to induce mRNA cleavage.

The discovery of miRNAs as endogenous small regulatory ncRNAs may represent the tip of the iceberg, with other groups of regulatory ncRNAs still to be discovered. Meanwhile, RNAi is now poised to revolutionize reverse genetics approaches, enabling virtually any gene of interest to be disrupted quickly and efficiently. Limitations of current RNAi technologies include their dependence upon inefficient transfection techniques and intrinsically transient nature. A challenge that must be met to realize the promise of future RNAi-based therapeutics is the development of efficient systems for siRNA delivery and expression in mammalian cells and organisms.

SUMMARY OF THE INVENTION

The present invention is based in part on the discovery that Adenovirus Virus-Associated (VA) RNA, is processed by the ribonuclease Dicer to generate ~21-23 nt RNA product. The instant inventors further discovered that infection with Adenovirus-5 (AD-5) can inhibit siRNA activity in mammalian cells. VA RNAs of the Adenoviridae family bear a striking resemblance to pre-miRNAs, which are similarly processed by Dicer into miRNAs. Other virus families encode untranslated RNAs having similar structures. Based on these discoveries, VA RNAs or other virally derived untranslated structural RNAs (referred to herein as structural viral RNAs or svRNAs) are believed to be incorporated into a Dicer (or an orthologue or homologue thereof) or RISC complex to function as substrates and/or inhibitors of the RNAi pathway.

Accordingly, the present invention features svRNAs (or derivatives thereof) for use as mediators of RNAi. In one embodiment, the svRNAs (or derivatives thereof) are activators of RNAi. Also featured are svRNAs (or derivatives thereof) for use as inhibitors of RNAi. Also featured are methods for identifying druggable targets, in particular, antiviral targets, mediated by the svRNAs (or derivatives thereof). Such targets are further useful in drug discovery methodologies. Also featured are expression cassettes and vectors (e.g., virus-derived vectors), the cassettes and/or vectors including VA RNA loci modified to deliver miRNA- and siRNA-like molecules.

BRIEF DESCRIPTION OF THE DRAWINGS

FIG. 16 is a demonstration that target cleavage is directed by VA RNA1.

FIG. 17 is a demonstration of accumulation of VA RNA1 and miVA1 in infected cells.

DETAILED DESCRIPTION OF THE INVENTION

Figure 1A:
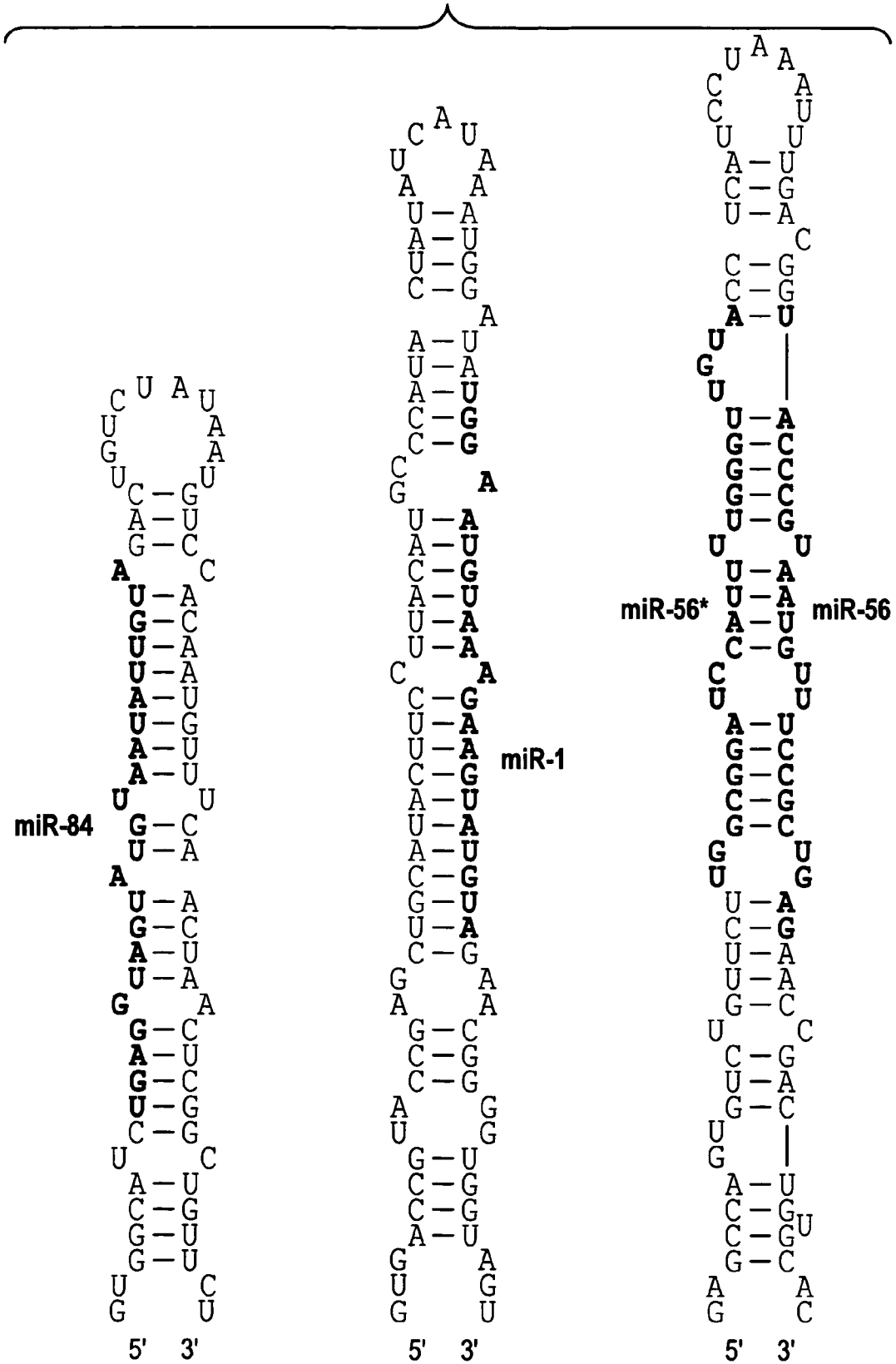
FIG. 1 is a comparison of the predicted secondary structures of miRNA precursors and structural viral RNAs. A) *C. elegans* miRNA precursors (miR-84, SEQ ID NO: 109; miR-1, SEQ ID NO: 110; miR-56, SEQ ID NO: 111) (2); B) Adenovirus type-5 VA $RNA_I$ (SEQ ID NO: 112) (1); C) Human Immunodeficiency Virus Type 1 (HIV-1) RRE (SEQ ID NO: 119) (26); D) Karposi's Sarcoma-associated herpesvirus (KSHV) IRES (SEQ ID NO: 113) (27); E) Hepatitis C Virus IRES (29); F) Poliovirus IRES (28).
Figure 1B:
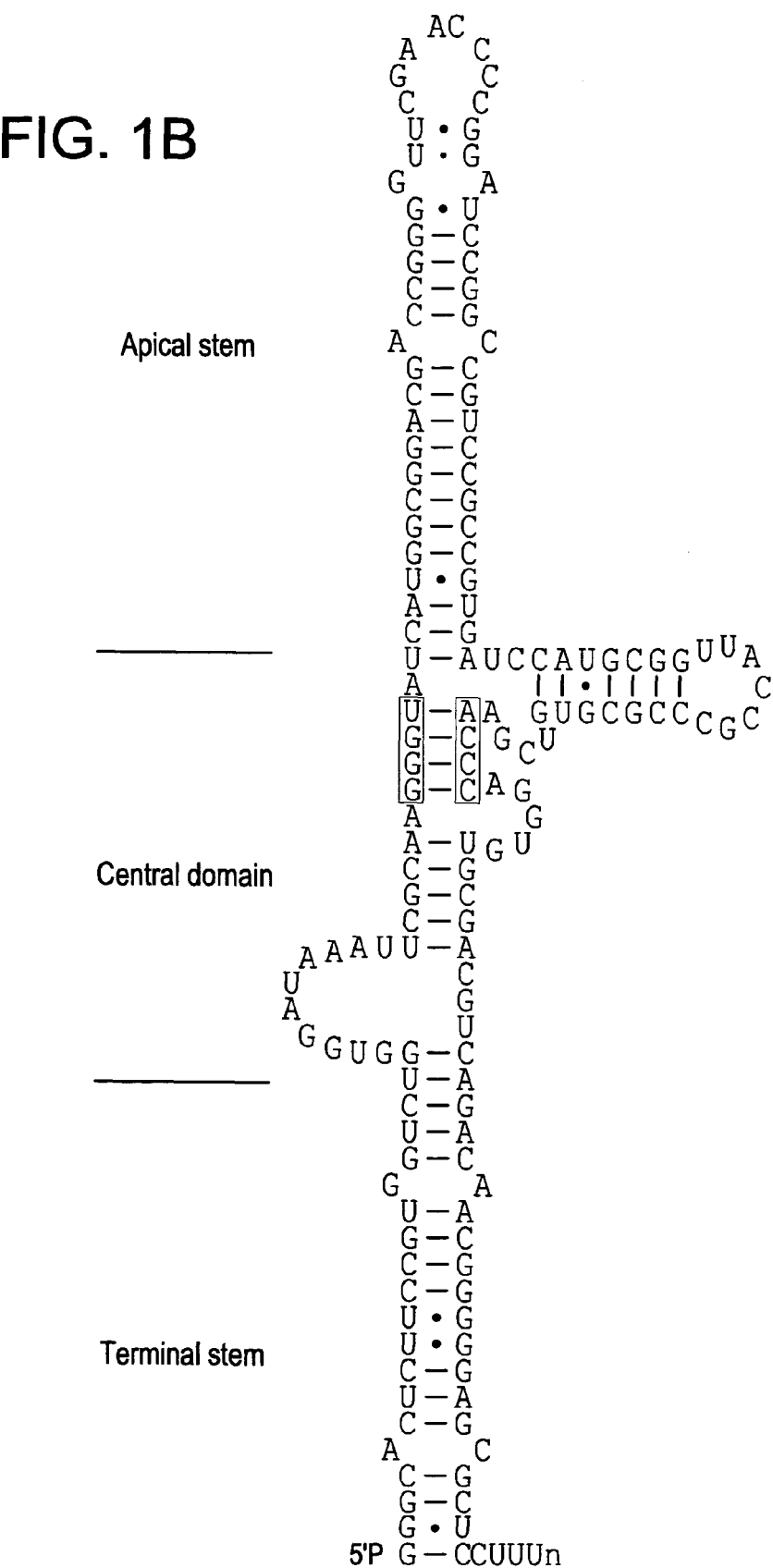
Figure 1C:
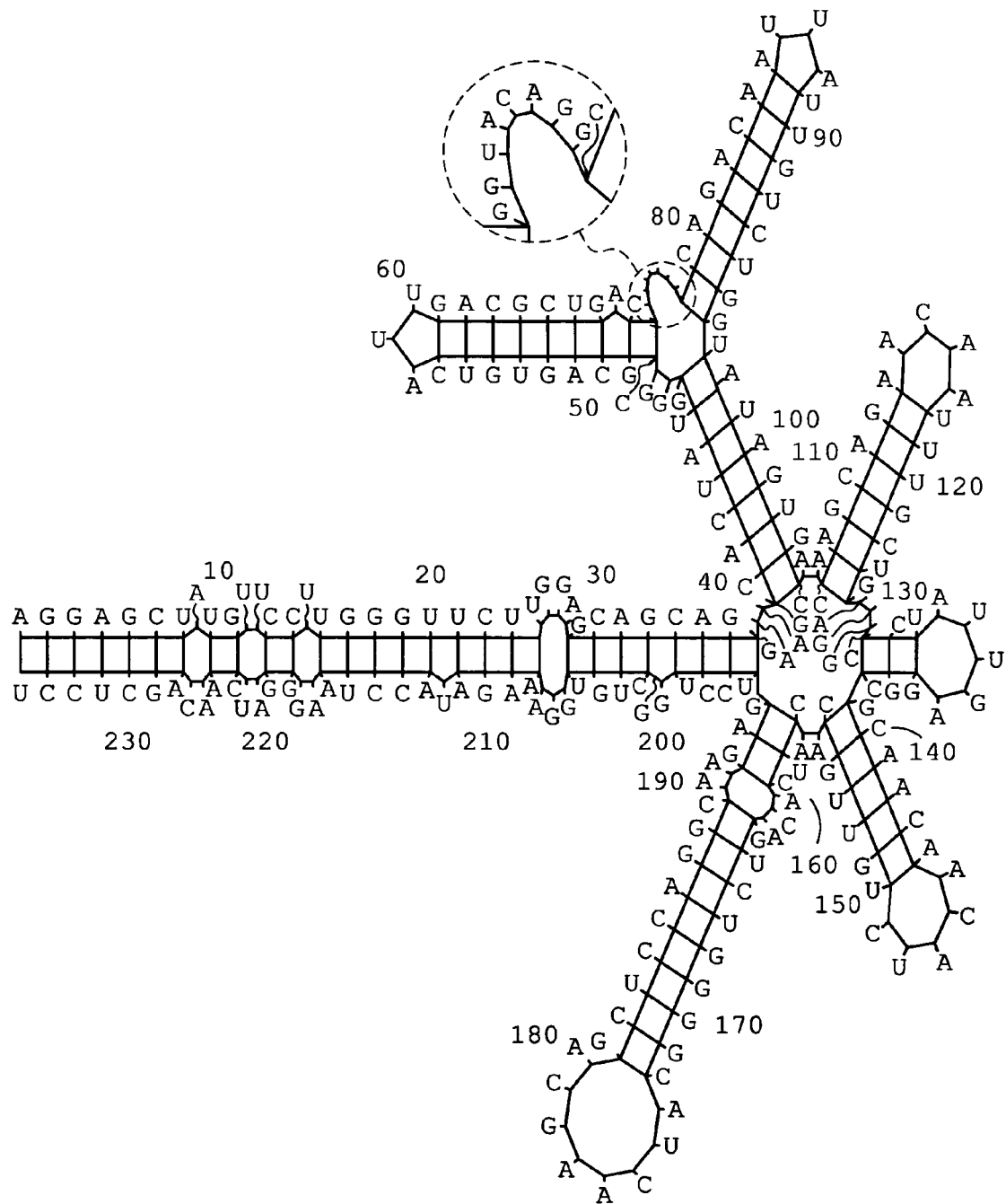
Figure 1D:
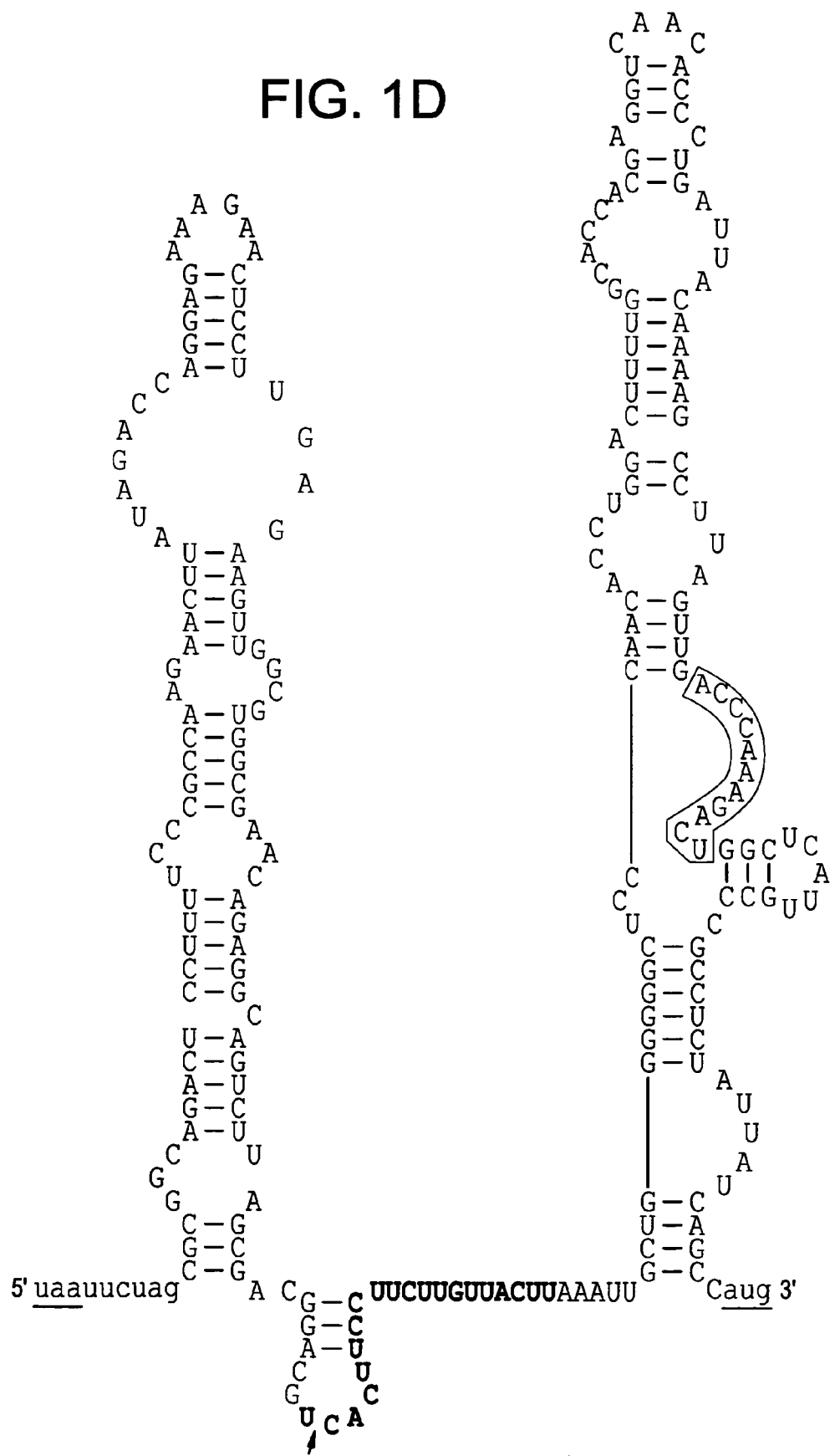
Figure 1E:
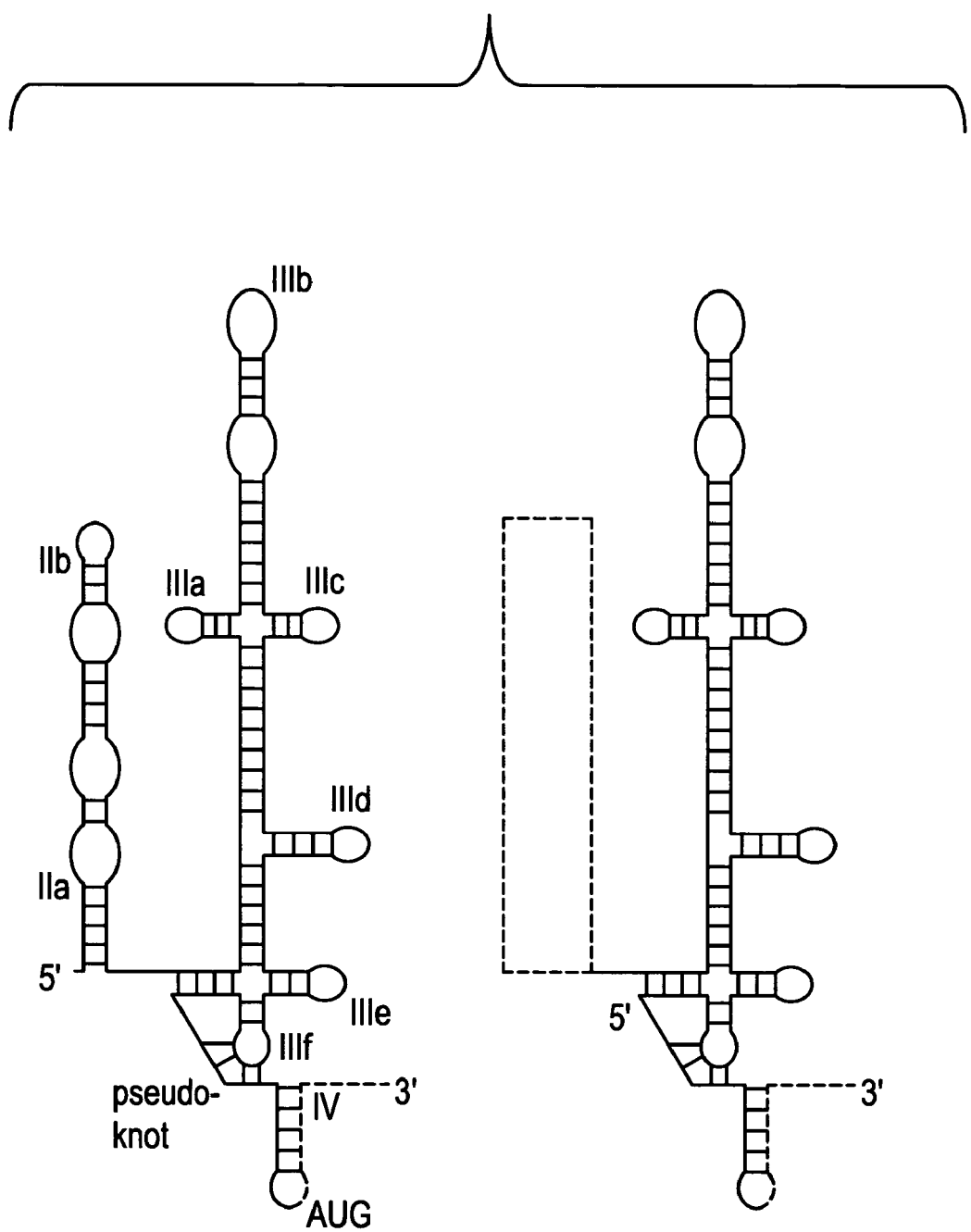
Figure 1F:
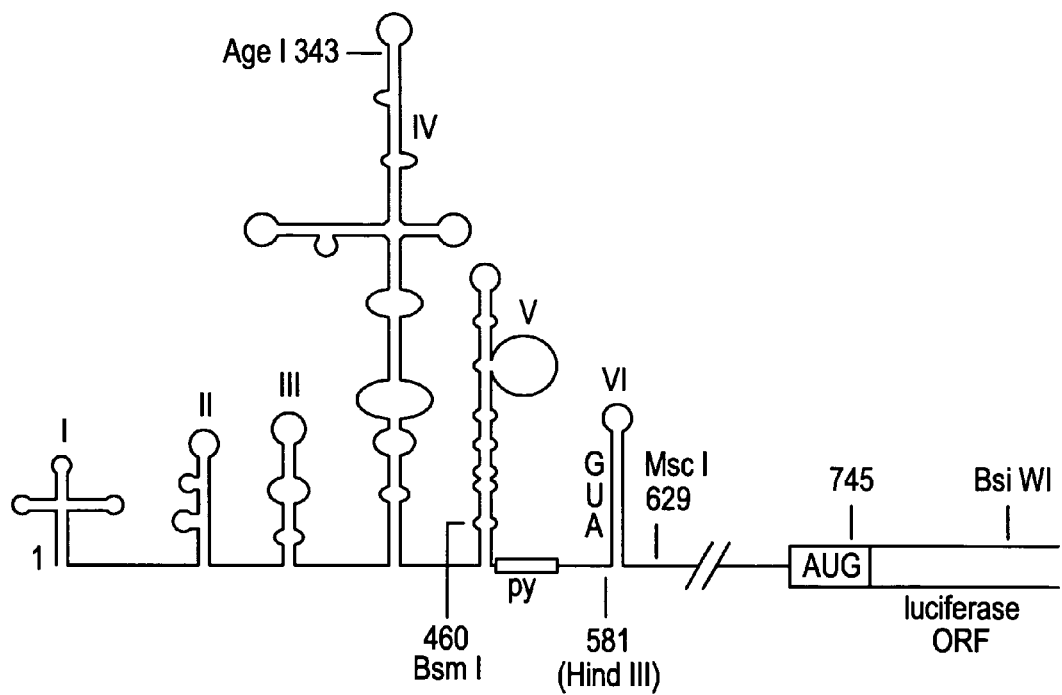

The present invention is based, at least in part, on the surprising discovery that a short non-coding RNA produced by Adenovirus, Adenovirus Virus-Associated (VA) $RNA_I$ is processed by the ribonuclease Dicer to generate ~21-23 nt RNA products. The present invention is based on the further discovery that infection with Adenovirus-5 (AD-5) can inhibit siRNA activity in mammalian cells. This processing of VA $RNA_I$ is similar to the processing events by Dicer of pre-miRNA into miRNAs. Pre-miRNAs are complex, double-stranded precursor RNA molecules characterized by key structural features such as stem loops and bulges (4, 10). VA RNAs of the Adenoviridae family bear a striking resemblance to pre-miRNAs. VA RNAs, which are produced at very high levels in infected cells, are generally believed to promote viral infection by binding and inhibiting the protein kinase PKR, where PKR normally functions to activate the interferon response upon binding dsRNA. Other virus families and viruses, e.g. gamma herpesvirinae, lentivirus and retrovirus, encode untranslated RNAs that have similar structures.

Based on the discoveries set forth herein, VA RNAs encoded by viruses within the Adenoviridae family, or alternatively, short untranslated structural RNAs encoded by other viruses, are proposed to act as precursors for cleavage by Dicer, thereby producing miRNA-like molecules that regulate gene expression. The concept of a virus encoding miRNA or miRNA-like sequences represents a hitherto unidentified mechanism by which viruses may control viral or cellular gene expression to produce an environment conducive to infection. Disruption of this viral function would result in attenuation of viral infection, thus providing novel antiviral strategies. Cellular and/or viral genes whose RNA expression is inhibited by VA RNAs make attractive targets for therapeutic anti-viral strategies as well as novel ways to modulate host homeostasis.

Given the high levels of VA RNA expressed in infected cells, VA RNAs are further proposed to act as inhibitors of RNAi by competing with other substrates for interaction with components of the RNAi pathway, e.g. Dicer, or components of RISC. This prevents processing of other potential RNAi triggers, including host miRNA precursors and viral transcripts. Antagonism of host cell RNAi by VA RNAs may further serve to promote virulence. Disabling the capacity of VA RNAs to antagonize host cell RNAi provides novel approaches for the creation of vaccines or in the design for their use as therapeutic vectors. Additionally, VA RNA loci can be modified to express miRNA- and siRNA-like molecules directed to selected target RNAs, thereby providing a highly efficient siRNA/miRNA transduction system.

Based at least in part on the above findings, the invention features, in a first aspect, methods for identifying genes whose expression is modulated by svRNAs (e.g., VA RNAs). In an exemplary aspect, the genes identified are involved in important cellular processes, for example, in the maintenance of cellular homeostasis or in the modulation of an antiviral response. The genes thus make desirable targets for drug discovery (i.e., druggable targets) or desirable antiviral drug targets, respectively.

Accordingly, the invention provides, in this first aspect, a method for identifying a druggable target, involving: (a) obtaining an assay composition comprising an RNAi pathway molecule and a svRNA; (b) assaying for expression of a candidate RNA; wherein a change in expression of the candidate RNA indicates that a gene or protein corresponding to the RNA is a druggable target. In a preferred embodiment, the assay composition is a cell extract, e.g., a mammalian cell extract.

In a related aspect, the invention provides a method for identifying a druggable target, comprising: (a) obtaining a cell or organism comprising an RNAi pathway and a svRNA; (b) assaying for expression of a candidate RNA; wherein a change in expression of the candidate RNA indicates that a gene or protein corresponding to the RNA is a druggable target. In preferred embodiments, the cell is a eukaryotic cell, e.g., a mammalian cell, a murine cell, an avian cell, a human cell and the like.

In one embodiment of these aspects, the RNA is an mRNA, e.g., an mRNA that encodes a viral protein or a cellular protein. In another embodiment, the RNA is a ncRNA, e.g., a ncRNA that regulates gene expression. Preferably, the druggable target is an antiviral drug target.

In one embodiment of these aspects, the change in expression of the candidate RNA is a decrease in the expression of the candidate RNA. In one embodiment, the methods involve a further step of preselecting the candidate RNA. Preferably, the preselection step involves determining a sufficient degree of sequence identity between the svRNA and the candidate RNA, e.g., wherein the svRNA and the candidate RNA share, for example, at least 60%, 70%, 80%, or 90% sequence identity. In other embodiments, the preselection step involves determining a sufficient degree of sequence identity between the svRNA and the candidate RNA, e.g., wherein the svRNA and the candidate RNA share, for example, at least 30%, 40%, 45%, 50% or 55% sequence identity. In another embodiment, the preselection step comprises selecting the candidate RNA based on its encoding a gene or protein having a desired cellular function, e.g., maintenance of cellular homeostasis or maintenance of differentiation.

Preferably, the svRNA in these related aspects is expressed from a virus, a vector, or a cassette. In a preferred embodiment, the svRNA is derived from a virus capable of infecting mammalian cells. In various embodiments, the svRNA is derived from a virus belonging to a family selected from the group consisting of the Herpesviridae, Retroviridae, Reoviridae, Flaviviridae, Poxyiridae and Picornaviridae families. In various embodiments, the svRNA is derived from a virus selected from the group consisting of EBV, HPV, MHV-68, HCMV, HIV, HCV, Dengue Virus, Foot and Mouth Disease Virus, Poliovirus, Vacciniavirus, Small Pox virus and KSHV. In preferred embodiments, the svRNA is selected from the group consisting of EBER 1, EBER 2, MHV-68 short ncRNAs, CMER, RRE, TAR, POLADS, PAN RNA and IRES.

In exemplary embodiments of the invention, the svRNA is derived from a virus belonging to the adenoviridae family, e.g., adenovirus type 2 or adenovirus type 5 virus. In further exemplary embodiments, the svRNA is a VA RNA, e.g., VA-RNA$_I$ or VA-RNA$_{II}$.

The invention further features a druggable target, e.g., an antiviral drug target, identified according to the provided methods of the invention. Such antiviral drug targets are useful in methods for identifying an antiviral agent, e.g., methods that involve assaying a test agent for activity against the antiviral drug target. In preferred embodiments, a method for identifying an antiviral agent involves assaying a test agent for the ability to stimulate expression or activity of the antiviral drug target, or to inhibit an interaction between the antiviral drug target and a corresponding svRNA.

The invention provides, in another aspect, a method for identifying an antiviral agent, involving: (a) contacting a cell with a test agent, said cell comprising an RNAi pathway and a svRNA, wherein said RNAi pathway generates a siRNA or miRNA from said svRNA; (b) detecting an indicator of said siRNA or miRNA; wherein an agent is identified based on its ability to inhibit the generation of said siRNA or miRNA.

In a related aspect, a method is provided for identifying an antiviral agent, involving: (a) contacting an assay composition with a test agent, wherein said assay composition comprises an RNAi pathway molecule and a svRNA, wherein said RNAi pathway molecule generates a siRNA or miRNA from said ribonucleotide; (b) detecting an indicator of said siRNA or miRNA; wherein an agent is identified based on its ability to inhibit the generation of said siRNA or miRNA.

The invention also provides an agent that is identified according to the methods of these aspects, as well as a pharmaceutical composition comprising the agent and a pharmaceutically acceptable carrier. These agents and compositions can be administered in an effective dose to an organism or subject in methods for attenuating and/or treating a viral infection. Preferably, the organism or subject is a eukaryotic organism, e.g., a mammal, e.g., a human.

The invention further features svRNA as inhibitors of the RNAi pathway. As inhibitors of RNAi, svRNAs compete with other substrates of the RNAi machinery to modulate expression of those genes regulated by siRNA or miRNA molecules.

Accordingly, in another aspect, the invention provides a method of inhibiting RNAi in a cell, involving introducing into the cell a svRNA or inhibitory derivative thereof, such that RNAi in the cell is inhibited. In a related aspect, a method is provided for inhibiting the incorporation of a siRNA or miRNA into a cellular Dicer or RISC complex, comprising introducing into the cell an isolated svRNA or inhibitory derivative thereof, such that incorporation of the siRNA or miRNA into the complex is inhibited.

In various embodiments, the cell is a eukaryotic cell, e.g., a mammalian cell, preferably a human cell. In another embodiment, the cell is present in an organism, e.g., present in a human subject.

In one embodiment, the svRNA is a VA RNA. In one embodiment, the svRNA is derived from a virus capable of infecting eukaryotic cells, e.g., mammalian cells. In an exemplary embodiment, the svRNA is derived from a virus belonging to the adenoviridae family, e.g., adenovirus type 2 or adenovirus type 5 virus. Preferably, the svRNA is VA-RNA$_I$ or VA-RNA$_{II}$.

Preferably, the svRNA in these related aspects is expressed from a virus, a vector, or a cassette. In various embodiments, the svRNA is derived from a virus belonging to a family selected from the group consisting of the Herpesviridae, Retroviridae, Reoviridae, Flaviviridae, Poxyiridae and Picornaviridae families. In various embodiments, the svRNA is derived from a virus selected from the group consisting of EBV, HPV, MHV-68, HCMV, HIV, HCV, Dengue Virus, Foot and Mouth Disease Virus, Poliovirus, Vacciniavirus, Small Pox virus and KSHV. In preferred embodiments, the svRNA is selected from the group consisting of EBER 1, EBER 2, MHV-68 short ncRNAs, CMER, RRE, TAR, POLADS, PAN RNA and IRES.

In yet another aspect of the invention, a method is provided for identifying an antiviral agent, involving: (a) contacting a cell with a test agent, said cell comprising an RNAi pathway and a svRNA, wherein the ribonucleotide inhibits the RNAi pathway; (b) detecting an indicator of the RNAi pathway; wherein an agent is identified based on its ability to alleviate inhibition of the RNAi pathway.

In a related aspect, the invention provides a method for identifying an antiviral agent, involving: (a) contacting an assay composition with a test agent, wherein said assay composition comprises a RNAi pathway molecule and a svRNA which inhibits the activity of said RNAi pathway molecule; (b) detecting activity of said RNAi pathway molecule; wherein said agent is identified based on its ability to restore activity of said RNAi pathway molecule.

In a third related aspect, the invention provides a method for identifying an antiviral agent, involving: (a) contacting an assay composition with a test agent, wherein said assay composition comprises a svRNA and a RNAi pathway molecule capable of interacting with or altering the svRNA; (b) detecting the ability of the RNAi pathway molecule to interact with or alter the svRNA; wherein said agent is identified based on its ability to modulate the interaction of the svRNA with the RNAi pathway molecule or alteration of the svRNA by the RNAi pathway molecule.

In one embodiment of these aspects, the RNAi pathway molecule is a RISC component. In another embodiment, the RNAi pathway molecule is Dicer, or a homologue thereof.

Agents identified according to these aspects are provided in the present invention, as well as pharmaceutical compositions comprising the agent and a pharmaceutically acceptable carrier.

Loci of svRNA and modified derivatives thereof are useful as delivery vehicles for RNAi agents, e.g., siRNA or miRNA-like molecules. Accordingly, in another aspect, the invention provides a vector for delivering a siRNA or miRNA, comprising a svRNA locus that has been modified to comprise a ribonucleotide sequence that encodes a siRNA or miRNA precursor. In one embodiment of this aspect, the vector comprises two svRNA loci. Preferably, the first svRNA locus is derived from adenovirus VA RNA$_I$ and a second svRNA locus is derived from VARNA$_{II}$. In one embodiment, the vector is a plasmid. In another embodiment, the vector is derived from a virus.

In a related aspect, a cassette is provided for expressing a siRNA or miRNA, comprising a svRNA locus that has been modified to comprise a ribonucleotide sequence that encodes a siRNA or miRNA precursor. In one embodiment of this aspect, the svRNA locus is derived from a virus of the Adenoviridae family. In exemplary embodiments, the svRNA locus is derived from adenovirus VA RNA$_I$ or VARNA$_{II}$.

In various embodiments, the svRNA is derived from a virus belonging to a family selected from the group consisting of the herpesviridae, retroviridae, flaviviridae, poxviridae and picornaviridae families. In various embodiments, the svRNA is derived from a virus is selected from the group consisting of EBV, HPV, MHV-68, HCMV, HIV, HCV, Dengue Virus, Foot and Mouth Disease Virus, Poliovirus, Vacciniavirus, Small Pox Virus and KSHV. In preferred embodiments, the svRNA is selected from the group consisting of EBER 1, EBER 2, MHV-68 short ncRNAs, CMER, RRE, TAR, POLADs, PAN RNA and IRES.

In some embodiments, the vector or cassette further comprises a polymerase III promoter operably linked to the ribonucleotide sequence. In other embodiments, the vector or cassette further comprises a cryptic promoter endogenous to the svRNA locus operably linked to the ribonucleotide sequence. In yet other embodiments, the sequence of the miRNA or siRNA molecule is sufficiently complementary to a RNA sequence to mediate degradation or to inhibit translation of said RNA sequence.

In another aspect, the invention provides a method for delivering a siRNA or miRNA in a cell at a significantly high level, comprising contacting the cell with the vector or cassette of the present invention under conditions such that the ribonucleotide sequences are expressed.

In yet another aspect, the invention features an adenovirus-derived vector that expresses a siRNA or miRNA from a VA RNA locus. In a related aspect, the invention provides an adenovirus-derived vector that expresses multiple (e.g., two, three, four, five, six, seven, eight or more) siRNA or miRNA. In one embodiment, the invention provides an adenovirus-derived vector that expresses a first siRNA or miRNA from a VA RNA$_I$ locus and a second siRNA or miRNA from a VA RNA$_{II}$ locus. In other embodiments, the invention provides an adenovirus-derived vector that expresses two, three, four, or more siRNA or miRNAs from the VA RNA$_I$ locus, from the VA RNA$_{II}$ locus, or from both the VA RNA$_I$ locus and the VA RNA$_{II}$ locus.

In one embodiment, the vector further comprises nucleotide sequences which encode at least one endogenous cellular protein. The invention further features a vaccine comprising these vectors, wherein at least one siRNA or miRNA targets a viral RNA or a cellular gene required for viral replication.

In yet another aspect, a viral-derived vector is provided that expresses a siRNA or miRNA from a svRNA locus and an exogenous gene from second locus. In a preferred embodiment, the siRNA or miRNA targets a mutant form, e.g., a dominant negative form or a dominant active form of a gene. In another preferred embodiment, the exogenous gene rescues haploinsufficiency.

The invention further provides a composition comprising the vectors of the invention and a pharmaceutically acceptable carrier. Such compositions are useful in methods for targeting degradation of RNA in a subject. Accordingly, the invention provides, in still another aspect, a method for targeting degradation of a RNA in a subject, comprising administering to the subject a composition of the invention, wherein the siRNA or miRNA has a ribonucleotide sequence having sufficient complementarity to the target RNA, such that the targets are degraded. In a related aspect, a method is provided for targeting degradation of multiple RNAs, e.g., a first and second RNA in a subject, comprising administering to the subject a composition of the invention, wherein, for example, a first siRNA or miRNA has a ribonucleotide sequence having sufficient complementarity to the first target RNA and a second siRNA or miRNA has a ribonucleotide sequence having sufficient complementarity to the second target RNA, such that the multiple targets are degraded. In various embodiments, multiple RNAs, e.g., three, four, five, six, seven, eight, nine, ten or more RNAs, are targeted by a composition of the invention. Preferably, in these aspects, at least one siRNA or miRNA has a ribonucleotide sequence sufficiently complementary to a mutant allelic target RNA, such that the mutant allelic target is degraded.

In still another aspect, a method is provided for targeting a RNA for translational inhibition in a subject, involving administering to the subject the composition of the invention, wherein the siRNA or miRNA has a ribonucleotide sequence having sufficient complementarity to the target RNA, such that the targets are translationally inhibited. In a related aspect, the invention provides a method for targeting multiple, e.g., a first and second RNA, for translational inhibition in a subject, comprising administering to the subject the composition of the invention, wherein, for example, a first siRNA or miRNA has a ribonucleotide sequence having sufficient complementarity to the first target RNA and a second siRNA or miRNA has a ribonucleotide sequence having sufficient complementarity to the second target RNA, such that the multiple targets are translationally inhibited. Preferably, in these aspects, at least one siRNA or miRNA has a ribonucleotide sequence sufficiently complementary to a mutant allelic target RNA, such that the mutant allelic target is translationally inhibited.

In yet another aspect, the invention provides a method for creating an attenuated virus, comprising modifying a svRNA locus of a virus, wherein the modification inhibits the ability of the svRNA to function as a substrate or inhibitor of a RNAi pathway, such that an attenuated virus is created. A vaccine produced according to this method is also provided.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

In addition, the materials, methods, and examples are illustrative only and not intended to be limiting.

I. Definitions

So that the invention may be more readily understood, certain terms are first defined.

The term "target gene", as used herein, refers to a gene intended for downregulation via RNA interference ("RNAi"). The term "target protein" refers to a protein intended for downregulation via RNAi. The term "target RNA" refers to an RNA molecule intended for degradation by RNAi. The term "target RNA" includes both non-coding RNA molecules (transcribed from a DNA but not encoding polypeptide sequence) and coding RNA molecules (i.e., mRNA molecules). A "target RNA" is also referred to herein as a "transcript".

The term "RNA interference" or "RNAi", as used herein, refers generally to a sequence-specific or selective process by which a target molecule (e.g., a target gene, protein or RNA) is downregulated. In specific embodiments, the process of "RNA interference" or "RNAi" features degradation of RNA molecules, e.g., RNA molecules within a cell, said degradation being triggered by an RNA agent. Degradation is catalyzed by an enzymatic, RNA-induced silencing complex (RISC). RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

The term "RNA agent", as used herein, refers to an RNA (or analog thereof), having sufficient sequence complimentarity to a target RNA (i.e., the RNA being degraded) to direct RNAi. A RNA agent having a "sequence sufficiently complementary to a target RNA sequence to direct RNAi" means that the RNA agent has a sequence sufficient to trigger the destruction of the target RNA by the RNAi machinery (e.g., the RISC complex) or process.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double-stranded, i.e., dsRNA and dsDNA, respectively).

The term RNA includes noncoding ("ncRNAs") and coding RNAs (i.e., mRNAs, as defined herein). ncRNAs are single- or double-stranded RNAs that do not specify the amino acid sequence of polypeptides (i.e., do not encode polypeptides). By contrast, ncRNAs affect processes including, but not limited to, transcription, gene silencing, replication, RNA processing, RNA modification, RNA stability, miRNA translation, protein stability, and/or protein translation. ncRNAs include, but are not limited to, bacterial small RNAs ("sRNA"), microRNAs ("miRNAs"), and/or small temporal RNAs ("stRNAs").

The term "mRNA" or "messenger RNA" refers to a single-stranded RNA that specifies the amino acid sequence of one or more polypeptide chains. This information is translated during protein synthesis when ribosomes bind to the miRNA.

The term "transcript" refers to a RNA molecule transcribed from a DNA or RNA template by a RNA polymerase template. The term "transcript" includes RNAs that encode polypeptides (i.e., mRNAs) as well as noncoding RNAs ("ncRNAs").

As used herein, the term "small interfering RNA" ("siRNA") (also referred to in the art as "short interfering RNAs") refers to an RNA agent, preferably a double-stranded agent, of about 10-50 nucleotides in length (the term "nucleotides" including nucleotide analogs), preferably between about 15-25 nucleotides in length, more preferably about 17, 18, 19, 20, 21, 22, 23, 24, or 25 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery (e.g., Dicer or a homolog thereof).

As used herein, the term "miRNA" or "microRNA" refers to an RNA agent, preferably a single-stranded agent, of about 10-50 nucleotides in length (the term "nucleotides" including nucleotide analogs), preferably between about 15-25 nucleotides in length, more preferably about 17, 18, 19, 20, 21, 22, 23, 24, or 25 nucleotides in length, which is capable of directing or mediating RNA interference. Naturally-occurring miRNAs are generated from stem-loop precursor RNAs (i.e., pre-miRNAs) by Dicer. The term "Dicer" as used herein, includes Dicer as well as any Dicer orthologue or homologue capable of processing dsRNA structures into siRNAs, miRNAs, siRNA-like or miRNA-like molecules. The term microRNA (or "miRNA") is used interchangeably with the term "small temporal RNA" (or "stRNA") based on the fact that naturally-occurring microRNAs (or "miRNAs") have been found to be expressed in a temporal fashion (e.g., during development).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region.

The term "svRNA" or "structural viral RNA", as used herein, refers to a viral ribonucleotide having a structure sufficient to facilitate utilization of the svRNA in an RNAi process. A preferred svRNA has a structure comprising at least one (possibly, two, three, four, five, six, seven, eight, nine, ten or more) double-stranded regions (i.e., stem regions), as described above in the context of shRNAs, interspersed with loop regions (e.g., one, two, three, four, five, six, seven, eight, nine, ten or more) (also defined above). svRNAs also can contain one or more "bulges" (i.e., short, for example, one, two or three residue regions interspersed within complementary regions (i.e., stem regions) that "bulge" due to a lack of complementarity with a corresponding region on an opposing strand and an inequality between the number of residues on opposing strands.

The term "VA RNA" or "virus-associated RNA", as used herein, refers to small (~155 nucleotides in length) structured, noncoding (regulatory) RNA found (naturally occurring) in adenovirus-infected cells (e.g., in the cytoplasm and/or nucleus). For mammalian adenoviruses (and related simian adenoviruses), VA RNAs are encoded by one or two VA RNA genes (i.e., VA $RNA_I$ and/or VAR $RNA_{II}$). The structure of a VA RNA comprises a terminal stem region, a central stem, and an apical stem region (see Ma, Y. and Matthews, M. B. (1996) *J. Virol.* 70: 5083-5099, the entire content of which is incorporated herein by reference). At least VA $RNA_I$ has been demonstrated to antagonize the mammalian antiviral response, presumably via a PKR-based mechanism.

The term protein kinase (PKR) refers to a kinase that normally functions to activate the interferon response upon binding dsRNA.

The term "nucleoside" refers to a molecule having a purine or pyrimidine base covalently linked to a ribose or deoxyribose sugar. Exemplary nucleosides include adenosine, guanosine, cytidine, uridine and thymidine. The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "nucleotide analog" or "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, *Antisense Nucleic Acid Drug Dev.*, 2000 August 10(4): 297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, *Antisense Nucleic Acid Drug Dev.* 2000 April 10(2): 117-21, Rusckowski et al. *Antisense Nucleic Acid Drug Dev.* 2000 October 10(5): 333-45, Stein, *Antisense Nucleic Acid Drug Dev.* 2001 October 11 (5): 317-25, Vorobjev et al. *Antisense Nucleic Acid Drug Dev.* 2001 April 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

The term "oligonucleotide" refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phophoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "isolated RNA" (e.g., "isolated svRNA", "isolated VA RNA" or "isolated RNAi agent") refers to RNA molecules which are substantially free of other cellular material, or culture medium when produced by recombinant techniques, or substantially free of chemical precursors or other chemicals when chemically synthesized.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the term "druggable target" refers to a target (i.e, gene or gene product) having certain desired properties which indicate a potential for drug discovery, i.e., for use in the identification, research and/or development of therapeutically relevant compounds. A druggable target is distinguished based on certain physical and/or functional properties selected by a person skilled in the art of drug discovery. A druggable target (i.e., gene or gene product) of the instant invention, for example, is distinguished from other genes and/or gene products based on the fact that that it is regulated by RNAi, preferably by RNAi mediated via a svRNA, VA RNA, or derivative thereof.

Based on the fact that these targets are regulated by RNAi, it is believed that the targets are important in essential cellular processes, for example, maintenance of cellular homeostasis, host cell defense mechanisms, and the like. Control of such processes, including situations in which such processes are misregulated (i.e., in the biology of a disease), has obvious therapeutic appeal. Additional criteria for identifying and/or selecting druggable targets include, but are not limited to (1) cellular localization susceptible to systemically administered (e.g., orally administered) drugs; (2) homology or similarity to other genes and/or gene products (e.g., member of a gene family) previously successfully targeted; and (3) data (e.g., expression and/or activity data) indicating a role for the gene/gene product at a critical intervention points in a disease pathway.

The term "antiviral drug target", as used herein, refers to a target (i.e, gene or gene product) having certain desired properties which indicate a potential for antiviral drug discovery, i.e., for use in the identification, research and/or development of compounds useful in antiviral therapies. A druggable target (i.e., gene or gene product) of the instant invention, for example, is indicated as an antiviral drug target based on the fact that viral RNAs, in particular, svRNAs, VA RNAs, or derivatives thereof can act as mediators (e.g., substrates and/or inhibitors) of RNAi.

A gene "involved" in a disorder includes a gene, the normal or aberrant expression or function of which effects or causes a disease or disorder or at least one symptom of said disease or disorder.

The phrase "examining the function of a gene in a cell or organism" refers to examining or studying the expression, activity, function or phenotype arising therefrom.

Various methodologies of the instant invention include step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNAi agent of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

II. Viral Non-Coding Structural RNAs

Viruses possess small genomes made up of nucleic acid. Examples of viruses possessing genomes made up of DNA include, but are not limited to, poxvirus, herpes virus, adenovirus, papillomavirus, and parvovirus. Examples of viruses possessing genomes made up of RNA include, but are not limted to, influenza virus, rotavirus, mumps virus, rabies virus, HIV/AIDS virus, corona virus, LCM virus and polio virus. The viral genome can be either single- or double-stranded, and is packaged in a capsid, or protein coat, which in enveloped viruses is further enclosed by a lipid envelope. Nonenveloped viruses leave an infected cell by lysing and thereby killing the cell. Enveloped viruses can leave the cell by budding, without disrupting the plasma membrane and, therefore, without killing the cell. Enveloped viruses can thus cause chronic infections, in some cases helping transform an infected cell into a cancer cell. All viruses use the basic host cell machinery for most aspects of their reproduction, including transcription and translation. Many viruses encode proteins that modify the host transcription or translation apparatus to favor the synthesis of viral proteins over those of the host cell. The synthetic capability of the host cell is thus directed principally to the production of new virus particles. While most of the viral genome encodes mRNA that is translated into functional protein, small genomic regions of most viruses encode untranslated, or non-coding, RNAs, e.g., structured RNAs. The function of these non-coding RNAs are the subject of great interest.

A. Virus-Associated RNAs of the Adenoviridae Family

The adenovirus genome is transcribed by two RNA polymerases. RNA polymerase II (pol II) transcribes both strands of the viral DNA, generating more than 50 viral proteins. RNA polymerse III (pol III) transcribes less than 1% of the viral genome, giving rise to one or two species of short, noncoding RNAs named virus-associated (VA) RNA (21). VA RNA are produced at very high levels during infection, reaching as high as $10^8$ molecules per cell, levels which are comparable to the number of ribosomes per cell. VA RNAs are common to all adenoviruses studied to date, although much work has concentrated on the group C adenoviruses, adenovirus types 2 and 5 (Ad2 and Ad5). Group C adenoviruses encode a major species, VA $RNA_I$, and a minor species, VA $RNA_{II}$, each being about ~160 nucleotides in length and which are able to adopt stable secondary structures (see FIG. 1). Deletions of VA $RNA_I$ or both VA RNA genes can greatly decrease viral growth (R. A. Bhat and B. Thimmappaya (1985) *J Virol.* 56: 750-756). Studies indicate that VA RNAs allow continued protein synthesis to occur in infected cells, due in part to its direct antagonism of the antiviral cellular defense system known as the interferon (IFN) response. VA RNAs are able to bind and inhibit the key protein kinase, PKR (also known as DAI, PI kinase, p68 kinase, or P1/eIF-2α kinase), which normally activates the interferon response upon the sequence-independent binding of dsRNA (21, 22). Thus this known infection-promoting activity of VA $RNA_I$ is dependent upon its ability to bind a dsRNA-binding enzyme.

Table 1 sets forth the nucleotide sequences of several important human and simian adenovirus VA RNA sequences.

| EMBL accession | Start | End | Species | Description | Sequence | SEQ ID NO: |
|---|---|---|---|---|---|---|
| AF108105 | 1023 6 | 1039 6 | Human adenovirus type 17 | Human adenovirus type 17 complete genome. | GGCUCUUCCUCCGUAGCCUGGCGGAACGCAAACGGGUUAG GCCGCGCGUGUACCCCGGUUCGAGUCCCCUCGAAUCAGGC UGGAGCCGCGACUAACGUGGUAUUGGCACUCCCGUCUCGA CCCGAGCCCGAUAGCCGCCAGGAUACGCGGGAaGAGCCCU U | 1 |
| AF108105 | 1045 5 | 1060 4 | Human adenovirus type 17 | Human adenovirus type 17 complete genome. GUCGCG-GCAGAACCCGGUUCGCGGACGGC-CGCGGCGAGCG | GGCUCGCGCCCGUAGUCUGGAGAAGCAUCGCCAGGGUUGA GGACUUGGUCACCCCGCCGAUUUAAAGACCCACAGCCAGC CGACUUCUCCAGUUACGGGAGCGAGCCCCC | 2 |
| AF394196 | 1042 0 | 1057 9 | Simian adenovirus | Simian adenovirus 25, complete genome. | GGCUCGACUCCGUGGCCUGGAGGCuAAGCGAACGGGUUGG GCUGCGCGUGUACCCCGGUUCGAAUCUCGAAUCAGGCUGG | 3 |

| EMBL accession | Start | End | Species | Description | Sequence | SEQ ID NO: |
|---|---|---|---|---|---|---|
| | | | 25 | | AGCCGCAGCUAACGUGGUAUUGGCACUCCCGUCUMGACCC AAGCBUGCACCAACCCUCCAGGAUACGGAGGCGGGUCGUU | |
| AF394196 | 1064 1 | 1079 9 | Simian adenovirus 25 | Simian adenovirus 25, complete genome. | GGCUCGUCUGCCGUAGUCUGGAGAAGAAUCGCCAGGGUUG CGUUGCGGUGUGCCCCGGUUCGAGGCCGGCCGGAUUCCGC GGCUAACGAGGGCGUGGCUGCCCCGUCGUUUCCAAGACCC CAuAGCCAGCCGACUUCUCCAGUUACGGAGCGAGCCCCU | 4 |
| AY163756 | 1043 2 | 1059 0 | Human adenovirus type 11 | Human adenovirus type 11 strain Ad11p Slobitski, complete genome. | GACUCGACUCCGUAGCCUGGAGGAACGUGAACGGGUUGGG UCGCGGUGUACCCCGGUUCGAGACUUGUACUCGAGCCGGC CCGAGCCGCGGCUAACGUGGUAUUGGCACUCCCGUCUCGA CCCAGCCUACAAAAAUCCAGGAUACGGAAUCGAGUCGUU | 5 |
| L05511 | 76 | 247 | Human adenovirus type 41 | Mastadenovirus h41 virus-associated (VA) RNA gene, complete gene and flanking regions. | GACUCUUCUCCGUAGCCUGGAGGAuaGACCGCCAGGGUGCG GGUCCCGAACAACCCCCGGUUCGAGACCGGCUGGAUCCGC CACUCCCGACGCGCCCGCCCCguguCACGACGGAAACCC CCCCGAGACCUAGCCGCGGUCCccggaUCUCCAGAUACGG AGGGGAGUCUUU | 6 |
| L06496 | 76 | 247 | Human adenovirus type 40 | Mastadenovirus h40 virus-associated (VA) RNA gene and flanking regions. | GACUUUCCUCCGUAGCCUGGGGGACAGAccGCCAGGGUGC AGUGGCAAACAACCCCCGGUUCGAGACCGGCUGGAUCUGC CacUCCCGACGCGCCCGCCGUGcGUCCAcgacGGAAACCC CGCCGAGACCUAGCCGcggUCCAuGGAUCUCCAGAUACGG AGGGGAGUCUUU | 7 |
| L19443 | 1006 6 | 1023 7 | Human adenovirus type 40 | Human adenovirus type 40, complete genome. | GACUUUCCUCCGUAGCCUGGAGGACAGAccGCCAGGGUGC AGUGGCAAACAACCCCCGGUUCGAGACCGGCUGGAUCUGC CacUCCCGACGCGCCGGCCGUGcGUCCAcgacGGAAACCC CGCCGAGACCUAGCCGcggUCCCUGGAUCUCCAGAUACGG AGGGGAGUCUUU | 8 |
| M86665 | 672 | 843 | Human adenovirus type 40 | Enteric mastadenovirus h40 penton protein gene, complete cds. | GACUUUCCUCCGUAGCCUGGAGGACAGAccGCCAGGGUGC AGUGGCAAACAACCCCCGGUUCGAGACCGGCUGGAUCUGC CacUCCCGACGCGCCGCCGUGcGUCCAcgacGGAAACCC CGCCGAGACCUAGCCGcggUCCCUGGAUCUCCAGAUACGG AGGGGAGUCUUU | 9 |
| U10672 | 2 | 160 | Human adenovirus type 11 | Human adenovirus type 11 virus-associated RNA gene. | GACUCGACUCCGUAGCCUGGAGGAACGUGAACGGGUUGGG UCGCGGUGUACCCCGGUUCGAGACUUGUACUCGAGCCGGC CGGAGCCGCGGCUAACGUGGUAUUGGCACUCCCGUCUCGA CCCAGCCUACAAAAAUCCAGGAUACGGAAUCGAGUCGUU | 10 |
| U10673 | 2 | 160 | Human adenovirus type 14 | Human adenovirus type 14 virus-associated RNA gene. | GACUCGACUCUGUAGCCUGGAGGAACGUGAACGGGUUGGG UCGCGGUGUACCCCGGUUCGAGACUUGUACUCGAGCCGGC CGGAGCCGCGGCUAACGUGGUAUUGGCACUCCCGUCUCGA CCCAGCCUACAAAAAUCCAGGAUACGGAAUCGAGUCGUU | 11 |

-continued

| EMBL accession | Start | End | Species | Description | Sequence | SEQ ID NO: |
|---|---|---|---|---|---|---|
| U10674 | 21 | 180 | Human adenovirus type 16 | Human adenovirus type 16 virus-associated RNA I and RNA II genes. | GGCUCGUCUCCGUGGCCUGGAGGCuAAGCGAACGGGUUGG GCUGCGCGUGUACCCCGGUUCGAAUCUCGGAUCAGGCUGG AGCCGCAGCUAACGUGGUACUGGCACUCCCGUCUCGACCC AGGCCUGCACAAAACCUCCAGGAUACGGAGGCGGGUCGUU | 12 |
| U10674 | 256 | 426 | Human adenovirus type 16 | Human adenovirus type 16 virus-associated RNA I and RNA II genes. | GGCUCGCGCCCGUAGUCUGGAGAAuCAAUCGCCAGGGUUG CGUUGCGGUGUGCCCCGGUUCGAGUCuUAGCGCGCGGAUC GGCCGCUUUCCGCGACAAGCGAGGGUUUGGCAGCCUCGUC AUUUCUAAGACCCCGCCAGCCGACUUCUCCAGUUUACGGG AGCGAGCCCUC | 13 |
| U10675 | 22 | 180 | Human adenovirus type 19 | Human adenovirus type 19 virus-associated RNA I and RNA II genes. | GGCUCUUCCUCCGUAGCCUGGCGGAACGAAACGGGUUAGG UCGCGUGUGUACCCCGGUUCGAGUCCCCUCGAAUCAGGCU GGAGCCGCGACUAACGUGGUAUUGGCACUCCCGUCUCGAC CCGAGCCCGAUAGCCGCCAGGAUACGGCGGAGAGCCCUU | 14 |
| U10675 | 239 | 385 | Human adenovirus type 19 | Human adenovirus type 19 virus-associated RNA I and RNA II genes. | GGCUCGCGCCCGUAGUCUGGAGAAGCAUCGCCAGGGUUGA GUCGCGGCAGAACCCGGUUCGAGGACGGCCGCGGCGAGCG GGACUUGGUCACCCCGCCGAUUUAAAGACCCACAGCCAGC CGACUUCUCCAGUUACGGGAGCGAGCC | 15 |
| U10677 | 2 | 160 | Human adenovirus type 34 | Human adenovirus type 34 virus-associated RNA gene. | GACUCGACUCCGUAGCCUGGAGGAACGUGAACGGGUUGGG UCGCGGUGUACCCCGGUUCGAGACUUGUACUCGAGCCGGC CGGAGCCGCGGCUAACGUGGUAUUGGCACUCCCGUCUCGA CCCAGCCUACAAAAAUCCAGGAUACGGAAUCGAGUCGUU | 16 |
| U10678 | 2 | 160 | Human adenovirus type 35 | Human adenovirus type 35 virus-associated RNA gene. | GACUCGACUCCGUAGCCUGGAGGAACGUGAACGGGUUGGG UCGCGGUGUACCCCGGUUCGAGACUUGUACUCGAGCCGGC CGGAGCCGCGGCUAACGUGGUAUUGGCACUCCCGUCUCGA CCCAGCCUACAAAAAUCCAGGAUACGGAAUCGAGUCGUU | 17 |
| U10679 | 22 | 180 | Human adenovirus type 37 | Human adenovirus type 37 virus-associated RNA I and RNA II genes. | GGCUCUUCCUCCGUAGCCUGGCGGAACGAAACGGGUUAGG CCGCGUGUGUACCCCGGUUCGAGUCCCCUCGAAUCAGGCU GGAGCCGCGACUAACGUGGUAUUGGCACUCCCGUCUCGAC CCAAGCCCGAUAGCCGCCAGGAUACGGCGGAGAGCCCUU | 18 |
| U10679 | 239 | 388 | Human adenovirus type 37 | Human adenovirus type 37 virus-associated RNA I and RNA II genes. | GGCUCGCGCCCGUAGUCUGGAGAAGCAUCGCCAGGGUUGA GUCGCGGCAGAACCCGGUUCAAGGACGGCCGCGGCGAGCG GGACUUGGUCACCCCGCCGAUUUAAAGACCCACAGCCAGC CGACUUCUCCAGUUACGGGAGCGAGCCCCC | 19 |
| U10680 | 24 | 195 | Human adenovirus type 3 | Human adenovirus type 3 virus-associated RNA I and RNA II genes. | GGCUCGACUCCGUGGUCUGGGGGAACGUGAACGGGUUGGG UCGCGGUGUACCCCGGUUCGAGUCcaaagcuaagcgAUCA CGCUCGGAUCGGCCGGAGCCGCGGCUAACGUGGUAUUGGC UAUCCCGUCUCGACCCAGCCGACGAAUAUCCAGGGUACGG AGUAGAGUCGUU | 20 |

-continued

| EMBL accession | Start | End | Species | Description | Sequence | SEQ ID NO: |
|---|---|---|---|---|---|---|
| U10680 | 268 | 440 | Human adenovirus type 3 | Human adenovirus type 3 virus-associated RNA I and RNA II genes. | GGCUCGCGCCCGUAGUCUGGAGAAuCAGUCGCCAGGGUUG CGUUGCGGUAUGCCCCGGUUGGAGCCuaaGCGCGGCUCGU AUCGGCCGGUUUCCGCGACAAGCAGGGUUUGGCAGCCCCG UUAUUUCCAAGACCCCGCCAGCCGACUUCUCCAGUUUACG GGAGCGAGCCCUU | 21 |
| U10681 | 196 | 340 | Human adenovirus type 4a | Human adenovirus type 4a virus-associated RNA I and RNA II genes. | GGUCCAAAAAAAGCUAGUAAGCACGGAAAGCGGCCGACC GCAAUGGCUCGCUGCCAGAUUUCGCAGCUAACGAGGGCGU GGCUGUCCCGUCGUUUCCAAGACCCCAuaAGCCAGCCAAC UUCUCCAGUUACGGAGCGAGCCCUC | 22 |
| U10681 | 21 | 180 | Human adenovirus type 4a | Human adenovirus type 4a virus-associated RNA I and RNA II genes. | GGCUCGACUCCGUGGCCUGGAGGCuAAGCAAACGGGUUGG GCUGCGCGUGUACCCCGGUUCGAAUCUCGAAUCAGGCUGG AGCCGCAGCUAACGUGGUACUGGCACUCCCGUCUCGACCC AGGCCUGCACAAAACCUCCAGGAUACGGAGGCGGGUCGUU | 23 |
| U10682 | 21 | 180 | Human adenovirus type 4 | Human adenovirus type 4 virus-associated RNA I and RNA II genes. | GGCUCGACUCCGUGGCCUGGAGGCuAAGCGAACGGGUUGG GCUGCGCGUGUACCCCGGUUCGAAUCUCGAAUCAGGCUGG AGCCGCAGCUAACGUGGUACUGGCACUCCCGUCUCGACCC AGGCCUGCACAAAACCUCCAGGAUACGGAGGCGGGUCGUU | 24 |
| U10682 | 239 | 406 | Human adenovirus type 4 | Human adenovirus type 4 virus-associated RNA I and RNA II genes. | GGCUCACUGCCGUAGAUUGGAGAAGAAUCGCCAGGGUUGC GUUGCGGUGUGCCCCGGUUCGAGACCGCUCGGGUCGGCCG AAUUCCGCGGCUAACGAGGGCGUGCCUGCCCCGUCGUUUC CAAGACCCCAuaAGCCAGCCGACUUCUCCAGUUACGGAGC GAGCCCCU | 25 |
| J01917 | 10607 | 10716 | Human adenovirus type 2 | Human adenovirus type 2 virus-associated RNA I gene. | AGCGGGCACUCUUCCGUGGUCUGGUGGAUAAAUUCGCAAG GGUAUCAUGGCGGACGACCGGCGUUCGAACCCCGGAUCCG GCCGUCCGCCGUGAUCCAUGCGGUUACCGC | 26 |
| J01917 | 10866 | 11023 | Human adenovirus type 2 | Human adenovirus type 2 virus-associated RNA II gene. | GGCUCGCUCCCGUAGCCGGAGGGUUAUUUUCCAAGGGUU GAGUCGCAGGACCCCCGGUUCGAGUCUCGGGCCGGCCGGA CUGCGGCGAACGGGGGUUUGCCUCCCCGUCAUGCAAGACC CCGCUUGCAAAUUCCUCCGGAAACAGGGACGAGCCCCU | 27 |
| X02996 | 10617 | 10778 | Human adenovirus type 5 | Human adenovirus type 5 virus-associated RNA I gene. | AGCGGGCACUCUUCCGUGGUCUGGUGGAUAAAUUCGCAAG GGUAUCAUGGCGGACGACCGGGGUUCGAGC CCCGUAUCCGGCCGUCCGCCGUGAUCCAUGCGGUUACCGC CCGCGUGUCGAACCCAGGUGUGCGACGUCA GACAACGGGGGAGUGCUCCUUU | 28 |
| X02996 | 10875 | 11035 | Human adenovirus type 5 | Human adenovirus type 5 virus-associated RNA II gene. | UGGCUCGCUCCCUGUAGCCGGAGGCUUAUUUUCCAAGGGU UGAGUCGCGGGACCCCCGGUUCGAGUCUCG GACCGGCCGGACUGCGGCGAACGCGGGUUUGCCUCCCCGU | 29 |

-continued

| EMBL accession | Start | End | Species | Description | Sequence | SEQ ID NO: |
|---|---|---|---|---|---|---|
| | | | | | CAUGCAAGACCCCGCUUGCAAAUUCCUCCG GAAACAGGGACGAGCCCCUUU | |
| U10683 | 23 | 181 | Human adenovirus type 8 | Human adenovirus type 8 virus-associated RNA I and RNA II genes. | GGCUCUUCCUCCGUAGCCUGGCGCAACGAAACGGGUUAGG CCGCGCGUGUACCCCGGUUCGAGUCCCCUCGAAUCAGGCU AAAGCCGCGACUAACGUGGUAUUGGCACUCCCGUCUCGAC CCAAGCCCGAUAGCCGCCAGGAUACGGUGAAGAGCCUUU | 30 |
| U10683 | 239 | 388 | Human adenovirus type 8 | Human adenovirus type 8 virus-associated RNA I and RNA II genes. | GGCUCGCGCCCGUAGUCUGGACAAGCAUCACUAGGGUUAA GUUACAGCAGAACCCGGUUCGCGGACGGCCGCGGCAAGCG GGACUUAGUUACCCCGCCAAUUUAAAGACCCGCAGCCAGC CGACUUUUCCAGUUACGGGAGCGAGCCCCC | 31 |
| U10684 | 21 | 181 | Simian adenovirus 23 | Simian adenovirus type 23 virus-associated RNA I and RNA II genes. | GCCUCGACUCCGUGGCCUGGAGCUAAGCGAACGGGUUGGG CUGCGCGUGUACCCCGGUUCGAAUCUCGAAUCAGGCUGGA GCCACAGCUAACGUGGUACUGGCACUCCCGUCUCGACCCA AGCCUGCUAACGAAACCUCCAGGAUACGGAGGCGGGUCGU U | 32 |
| U10684 | 240 | 411 | Simian adenovirus 23 | Simian adenovirus type 23 virus-associated RNA I and RNA II genes. | CCCUCGCUGCCGUAGUCUGGAGAAaGAAUCGCCAGGGUUG CGUUGCGGUGUGCCCCGGUUCGAGCCuCAGCGCUCGGCGC CGGCCGGAUUCCGCGGCUAACGUGGCGUGGCUGCCCCGUC GUUUCCAAGACCCCUuAGCCAGCCGACUUCUCCAGUUACG GAGCGAGCCCCU | 33 |
| U52534 | 118 | 289 | Human adenovirus type 3 | Human adenovirus type 3 virus-associated RNA pre-terminal protein (pTP) and 52,55 K protein genes, partial cds. | GGCUCGACUCCGUGGUCUCGGGGAACGUGAACGGGUUGGG UCGCGGUGUACCCCGGUUCGAGUCcaaagcuaagcgAUCA CGCUCGGAUCGGCCGGAGCCGCGGCUAACGUGGUAUUGGC UAUCCCGUCUCGACCCAGCCGACGAAUAUCCAGGCUACGG AGUAGAGUCGUU | 34 |
| U52534 | 362 | 535 | Human adenovirus type 3 | Human adenovirus type 3 virus-associated RNA pre-terminal protein (pTP) and 52,55 K protein genes, partial cds. | GGCUCGCGCCCGUAGUCUGGAGAAuCAGUCGCCAGGGUUG CGUUGCGGUAUGCCCCGGUUGGAGCCuaaGCGCGGCUCGU AUCGGCCGGUUUCCGCGACAAGCGAGGGUUUGGCAGCCCC CUUAUUUCCAAGACCCCGCCAGCCGACUUCUCCAGUUUAC GGGAGCCAGCCCUU | 35 |
| U52535 | 119 | 278 | Human adenovirus type 4 | Human adenovirus type 4 virus-associated RNA pre-terminal protein (pTP) and 52,55 K protein genes, partial cds. | GGCUCGACUCCGUGGCCUGGAGGCuAAGCGAACGGGUUGG GCUGCGCGUGUACCCCGGUUCGAAUCUCGAAUCAGGCUGG AGCCGCAGCUAACGUGGUACUGGCACUCCCGUCUCGACCC AGGCCUGCACAAAACCUCCAGGAUACGGAGGCGGGUCGUU | 36 |
| U52535 | 337 | 504 | Human adenovirus type 4 | Human adenovirus virus-associated RNA pre- | GCCUCACUGCCGUAGAUUGGAGAAGAAUCGCCAGGGUUGC GUUGCCGUCUGCCCCGGUUCCACACCCCUCCGGUCCGCCG | 37 |

-continued

| EMBL accession | Start | End | Species | Description | Sequence | SEQ ID NO: |
|---|---|---|---|---|---|---|
| | | | type 4 | terminal protein (pTP) and 52,55 K protein genes, partial cds. | AAUUCCGCCCCUAACCACCGCCUCCCUGCCCCGUCCUUUC CAAGACCCCAuaAGCCAGCCGACUUCUCCAGUUACGCACC CAGCCCCU | |
| U52536 | 115 | 274 | Human adenovirus type 9 | Human adenovirus type 9 virus-associated RNA pre-terminal protein (pTP) and 52,55 K protein genes, partial cds. | GGCUCUUCCUCCCUAGCCUGGCGGAACGCAAACGGGUUAG GCCGCGUGUGUACCCCGGUUCGACUCCCCUUGAAUCAGGC UGGAGCCGCCACUAACGUGCUAUUGGCACUCCCGUCUCGA CCCGAGCCCGAUAGCCGCCAGGAUACGGCGGAGAGUCCUU | 38 |
| U52536 | 333 | 482 | Human adenovirus type 9 | Human adenovirus type 9 virus-associated RNA pre-terminal protein (pTP) and 52,55 K protein genes, partial cds. | GGCUCGCGCCCGUAGUCUGGAGAAGCAUCGCCAGGGUUGA GUCGCGGCAGAACCCGGUUCGCGGACGGCCGCGGCGAGCG GGACUUGGUCACCCCGCCGAUUUAAAGACCCACAGCCAGC CGACUUCUCCAGUUACGGGAGCGAGCCCCC | 39 |
| U52537 | 115 | 274 | Human adenovirus type 13 | Human adenovirus type 13 virus-associated RNA pre-terminal protein (pTP) and 52,55 K protein genes, partial cds. | GGCUCUUCCUCCGUAGCCUGGCGGAACGCAAACGGGUUAG GCCGCGCGUGUACCCCGGUUCGAGUCCCCUCGAAUCAGGC UGGAGCCGCGACUAACGUGGUAUUGGCACUCCCGUCUCGA CCCGAGCCCGAUAGCCGCCAGGAUACGGCGGAGAGCCCUU | 40 |
| U52537 | 333 | 482 | Human adenovirus type 13 | Human adenovirus type 13 virus-associated RNA pre-terminal protein (pTP) and 52,55 K protein genes, partial cds. | GGCUCGCGCCCGUAGUCUGGAGAAGCAUCGCCAGGGUUGA GUCGCGGCAGAACCCGGUUCGCGGACGGCCGCGGCGAGCG GGAAUUGGUCACCCCGCCUAUUUAAAGACCCACAGCCAGC CCACUUCUCCAGUUACGGGAGCGAGCCCCC | 41 |
| U52538 | 115 | 274 | Human adenovirus type 15 | Human adenovirus type 15 virus-associated RNA pre-terminal protein (pTP) and 52,55 K protein genes, partial cds. | GGCUCUUCCUCCGUAGCCUGGCGGAACGCAAACGGGUUAG CCGCGUGUGUACCCCGGUUCGAGUCCCCUCGAAUCAGGC UGGAGCCGCGACUAACGUGGUAUUGGCACUCCCGUCUCGA CCCAAGCCCGAUAGCCGCCAGGAUACGGCGGAGAGCCCUU | 42 |
| U52538 | 333 | 482 | Human adenovirus type 15 | Human adenovirus type 15 virus-associated RNA pre-terminal protein (pTP) and 52,55 K protein genes, partial cds. | GGCUCGCGCCCGUAGUCUGGAGAAGCAUCGCCAGGGUUGA GUCGCGGCAGAACCCGGUUCGCGGACGGCCGCGGCGAGCG GGACUUGGUCACCCCGCCGAUUUAAAGACCCACAGCCAGC CGACUUCUCCAGUUACGGGAGCGAGCCCCC | 43 |
| U52539 | 115 | 274 | Human adenovirus type 17 | Human adenovirus type 17 virus-associated RNA pre-terminal protein (pTP) and | GCCUCUUCCUCCGUAGCCUGGCGGAACGCAAACGGGUUAG GCCGCGCGUGUACCCCGGUUCGAGUCCCCUCGAAUCAGGC UGGAGCCGCGACUAACGUGGUAUUGGCACUCCCGUCUCGA | 44 |

-continued

| EMBL accession | Start | End | Species | Description | Sequence | SEQ ID NO: |
|---|---|---|---|---|---|---|
| | | | | 52,55 K protein genes, partial cds. | CCCGAGCCCGAUACCCGCCAGGAUACGGCGGAGAGCCCUU | |
| U52539 | 333 | 482 | Human adenovirus type 17 | Human adenovirus type 17 virus-associated RNA pre-terminal protein (pTP) and 52,55 K protein genes, partial cds. | GGCUCGCGCCCGUAGUCUGGAGAACCAUCGCCAGGGUUGA GUCGCGGCAGAACCCGGUUCGCGGACGGCCGCGGCGAGGG GGACUUGGUCACCCCGCCGAUUUAAAGACCCACAGCCAGC CGACUUCUCCAGUUACGGGAGCGAGCCCCC | 45 |
| U52540 | 115 | 274 | Human adenovirus type 19 | Human adenovirus type 19 virus-associated RNA pre-terminal protein (pTP) and 52,55 K protein genes, partial cds. | GGCUCUUCCUCCGUAGCCUGGCGGAACGCAAACGGGUUAG GUCGCGUGUGUACCCCGGUUCGAGUCCCCUCGAAUCAGGC UGGAGCCGCGACUAACGUGGUAUUGGCACUCCCGUCUCGA CCCGAGCCCGAUAGCCGCCAGCAUACGGCGGAGAGCCCUU | 46 |
| U52540 | 333 | 482 | Human adenovirus type 19 | Human adenovirus type 19 virus-associated RNA pre-terminal protein (pTP) and 52,55 K protein genes, partial cds. | GGCUCGCGCCCGUAGUCUGGAGAAGCAUCGCCAGGGUUGA GUCGCCGCAGAACCCGGUUCGAGGACGGCCGCGGCGAGCG GACUUGGUCACCCCGCCGAUUUAAAGACCCACAGCCAGC CGACUUCUCCAGUUACGGGAGCGAGCCCCC | 47 |
| U52541 | 115 | 274 | Human adenovirus type 20 | Human adenovirus type 20 virus-associated RNA pre-terminal protein (pTP) and 52,55 K protein genes, partial cds. | GGCUCUUCCUCCGUAGCCUGGCGGAACGCAAACGGGUUAG GCCGCGUGUGUACCCCGGUUCGAGUCCCCUCGAAUCAGGC UGGAGCCGCGACUAACGUCGUAUUGGCACUCCCGUCUCGA CCCAAGCCCGAUAGCCGCCAGGAUACGGCGGAGAGCCCUU | 48 |
| U52541 | 333 | 482 | Human adenovirus type 20 | Human adenovirus type 20 virus-associated RNA pre-terminal protein (pTP) and 52,55 K protein genes, partial cds. | GGCUCGCGCCCGUAGUCUGGAGAAGCAUCGCCAGGGUUGA GUCGCGGCAGAACCCGGUUCGCGGACGGCCGCGGCGAGCG GGACUUGGUCACCCCGCCGAUUUAAAGACCCACAGCCAGC CGACUUCUCCAGUUACGGGAGCGAGCCCCC | 49 |
| U52542 | 115 | 274 | Human adenovirus type 22 | Human adenovirus type 22 virus-associated RNA pre-terminal protein (pTP) and 52,55 K protein genes, partial cds. | GGCUCUUCCUCCGUAGCCUGGCGGAACGCAAACGGGUUAG GCCGCGUGUGUACCCCGGUUCGAGUCCCCUCGAAUCAGGC UGCAGCCGCGACUAACGUGGUAUUGGCACUCCCGUCUCGA CCCAAGCCCGAUAGCCGCCAGGAUACGGCGGAGAGCCCUU | 50 |
| U52542 | 333 | 482 | Human adenovirus type 22 | Human adenovirus type 22 virus-associated RNA pre-terminal protein (pTP) and 52,55 K protein genes, partial cds. | GGCUCGCGCCCGUAGUCUGGAGAAGCAUCGCCAGGGUUGA GUCCCCGCAGAACCCGGUUCAAGGACGGCCGCGGCAAGCG GACUUGGUCACCCCGCCGAUUUAAAGACCCACAGCCAGC CGACUUCUCCAGUUACGGGAGCGAGCCCCC | 51 |

-continued

| EMBL accession | Start | End | Species | Description | Sequence | SEQ ID NO: |
|---|---|---|---|---|---|---|
| U52543 | 115 | 274 | Human adenovirus type 23 | Human adenovirus type 23 virus-associated RNA pre-terminal protein (pTP) and 52,55 K protein genes, partial cds. | GGCUCUUCCUCCGUAGCCUGCCGGAACGCAAACGGGUUAG GCCGCGUGUGUACCCCGGUUCGAAUCCCCUCGAAUCAGGC UGGAGCCGCGACUAACGUGGUAUUGGCACUCCCGUCUCGA CCCGAGCCCGAUAGCCGCCAGGAUACGGCGGAGAGCCCUU | 52 |
| U52543 | 333 | 482 | Human adenovirus type 23 | Human adenovirus type 23 virus-associated RNA pre-terminal protein (pTP) and 52,55 K protein genes, partial cds. | GGCUCGCCCCGUAGUCUGGAGAACCAUCGCCAGGGUUGA GUCGCGGCAGAACCCGGUUCGCGGACGGCCGCGGCGAGCG GACUUGGUCACCCCGCCGAUUUAAAGACCCACAGCCAGC CGACUUCUCCAGUUACGGGAGCGAGCCCCC | 53 |
| U52544 | 115 | 274 | Human adenovirus type 24 | Human adenovirus type 24 virus-associated RNA pre-terminal protein (pTP) and 52,55 K protein genes, partial cds. | GGCUCUUCCUCCGUAGCCUGGCGGAACGCAAACGGGUUAG GCCGCGUGUGUACCCCGGUUCGAGUCCCCUCGAAUCAGGC UGGAGCCGCGACUAACGUGGUAUUGGCACUCCCGUCUCGA CCCGAGCCCGAUAGCCGCCAGGAUACGGCGGAGAGCCCUU | 54 |
| U52544 | 333 | 482 | Human adenovirus type 24 | Human adenovirus type 24 virus-associated RNA pre-terminal protein (pTP) and 52,55 K protein genes, partial cds. | GGCUCGCGCCCGUAGUCUGGAGAAGCUUUGCCAGGGUUGA GUCGCGGCAGAACCCGGUUCGCGGACGGCCGCGGCGAGCG GACUUGGUCACCCCGCCGAUUUAAAGACCCACAGCCAGC CGACUUCUCCAGUUACGGGAGCGAGCCCCC | 55 |
| U52545 | 115 | 274 | Human adenovirus type 25 | Human adenovirus type 25 virus-associated RNA pre-terminal protein (pTP) and 52,55 K protein genes, partial cds. | GGCUCUUCCUCCGUAGCCUGGCGGAACGCAAACGGGUUAG CCCGCGUGUGUACCCCGGUUCGAGUCCCCUCGAAUCAGGC GGAGCCGCGACUAACGUGGUAUUCCCACUCCCGUCUCGA CCCGAGCCCGAUAGCCGCCAGGAUACGGCGCACAGCCCUU | 56 |
| U52545 | 333 | 482 | Human adenovirus type 25 | Human adenovirus type 25 virus-associated RNA pre-terminal protein (pTP) and 52,55 K protein genes, partial cds. | GGCUCCCGCCCCUAGUCUGGAGAAGCAUCGCCACGGUUGA GUCCCCCCAGAACCCGGUUCGAGCACGGCCGCGGCGAGCG GACUUGGUCACCCCGCCGAUAUAAAGACCCACAGCCAGC CGACUUCUCCAGUUACGGGACCGACCCCCC | 57 |
| U52546 | 115 | 274 | Human adenovirus type 26 | Human adenovirus type 26 virus-associated RNA pre-terminal protein (pTP) and 52,55 K protein genes, partial cds. | GGCUCUUCCUCCCUAGCCUCGCGCAACGCAAACGGGUUAG GCCGCGUGUGUACCCCGGUUCCAGUCCCCUCGAAUCAGGC UGGAGCCGCGACUAACGUGGUAUUGGCACUCCCGUCUCGA CCCGAGCCCCAUAGCCGCCAGGAUACGGCGGAGAGCCCUU | 58 |
| U52546 | 333 | 482 | Human adenovirus type 26 | Human adenovirus type 26 virus-associated RNA pre-terminal protein (pTP) and 52,55 K protein genes, partial cds. | CGCUCGCGCCCGUAGUCUGCAGAACCAUCGCCAGGGUUGA GUCGCGGCAGAACCCGGUUCGAGGACGGCCGCGGCGAGCG GGACUUGGUCACCCCGCCGAUAUAAAGACCCACAGCCAGC | 59 |

| EMBL accession | Start | End | Species | Description | Sequence | SEQ ID NO: |
|---|---|---|---|---|---|---|
| | | | | 52,55 K protein genes, partial cds. | CGACUUCUCCAGUUACGGGAGCGAGCCCCC | |
| U52547 | 115 | 274 | Human adenovirus type 27 | Human adenovirus type 27 virus-associated RNA pre-terminal protein (pTP) and 52,55 K protein genes, partial cds. | GGCUCUUCCUCCGUACCCUGGCCCAACGCAAACGGGUUAG GCCGCGUGUGUACCCCGGUUCGAGUCCCCUCGAAUCAGGC UGGAGCCGCCACUAACGUGGUAUUGGCACUCCCGUCUCGA CCCGAGCCCGAUAGCCGCCAGGAUACGGCGGAGAGCCCUU | 60 |
| U52547 | 333 | 482 | Human adenovirus type 27 | Human adenovirus type 27 virus-associated RNA pre-terminal protein (pTP) and 52,55 K protein genes, partial cds. | GGCUCCCGCCCGUAGUCUGGAGAAGCAUCGCCAGGGUUGA GUCGCGGCAGAACCCGGUUCGAGGACCCCCGCGGCGAGCG GGACUUGGUCACCCCGCCGAUUUAAAGACCCACAGCCAGC CGACUUCUCCAGUUACGGGAGCGAGCCCCC | 61 |
| U52548 | 115 | 274 | Human adenovirus type 28 | Human adenovirus type 28 virus-associated RNA pre-terminal protein (pTP) and 52,55 K protein genes, partial cds. | GGCUCUUCCUCCGUAGCCUGGCGGAACGCAAACGGGUUAG GCCGCGUGUGUACCCCGGUUCGAGUCCCCUCGAAUCAGGC UGGAGCCGCGACUAACGUGGUAUUCGCACUCCCGUCUCGA CCCGAGCCCGAUAGCCGCCAGGAUACGGCGGAGAGCCCUU | 62 |
| U52548 | 333 | 482 | Human adenovirus type 28 | Human adenovirus type 28 virus-associated RNA pre-terminal protein (pTP) and 52,55 K protein genes, partial cds. | CGCUCGCGCCCGUAGUCUGGAGAAGCAUCGCCAGGGUUGA GUCCCGGCAGAACCCCGUUCGCGGACGGCCGCGGCGAGCG GGACUUCGUCACCCCGCCGAUUUAAAGACCCACAGCCAGC CGACUUCUCCACUUACGGGAGCGAGCCCCC | 63 |
| U52549 | 115 | 274 | Human adenovirus type 29 | Human adenovirus type 29 virus-associated RNA pre-terminal protein (pTP) and 52,55 K protein genes, partial cds. | GGCUCUUCCUCCGUAGCCUGGCGGAACGCAAACGGGUUAG GCCGCCUCUGUACCCCGUUCGAGUCCCCUCGAAUCAGGC UGGAGCCGCGACUAACGUGGUAUUCCCACUCCCGUCUCGA CCCGAGCCCGAUAGCCGCCAGGAUACGGCGGAGAGCCCUU | 64 |
| U52549 | 333 | 482 | Human adenovirus type 29 | Human adenovirus type 29 virus-associated RNA pre-terminal protein (pTP) and 52,55 K protein genes, partial cds. | GGCUCGCGCCCGUAGUCUGGAGAACCAUCGCCAGGGUUCA CUCCCCGCAGAACCCGGUUCGAGCACGGCCGCGGCGACCG GGACUUGGUCACCCCGCCGAUUUAAAGACCCACAGCCAGC CCACUUCUCCAGUUACGGGAGCCACCCCCC | 65 |
| U52550 | 115 | 274 | Human adenovirus type 30 | Human adenovirus type 30 virus-associated RNA pre-terminal protein (pTP) and 52,55 K protein genes, partial cds. | GGCUCUUCCUCCGUAGCCUCCCGCAACGCAAACGGUUAG GCCGCGUGUGUACCCCGGUUCGACUCCCCUCGAAUCAGGC GGAGCCGCGACUAACGUGGUAUUGGCACUCCCGUCUCGA CCCGACCCCGAUAGCCGCCAGGAUACGGCGGAGAGCCCUU | 66 |

-continued

| EMBL accession | Start | End | Species | Description | Sequence | SEQ ID NO: |
|---|---|---|---|---|---|---|
| U52550 | 333 | 482 | Human adenovirus type 30 | Human adenovirus type 30 virus-associated RNA pre-terminal protein (pTP) and 52,55 K protein genes, partial cds. | GGCUCGCGCCCCUAGUCUGGAGAACCAUCGCCAGGGUUGA GUCGCGGCAGAACCCGGUUCCCGCACGGCCGCGGCGAGCG CACUUCGUCACCCCCCCGAUUUAAAGACCCACAGCCAGC CCACUUCUCCAGUUACGGGAGCGAGCCCCC | 67 |
| U52551 | 115 | 274 | Human adenovirus type 32 | Human adenovirus type 32 virus-associated RNA pre-terminal protein (pTP) and 52,55 K protein genes, partial cds. | GGCUCUUCCUCCGUAGCCUGGCCCAACGCAAACGCGUUAG GCCGCGUCUGUACCCCCCUUCGAGUCCCCUCGAAUCAGGC UCCAGCCGCGACUAACGUGGUAUUCCCACUCCCGUCUCGA CCCGACCCCGAUAGCCGCCAGGAUACGGCGGAGAGCCCUU | 68 |
| U52551 | 333 | 482 | Human adenovirus type 32 | Human adenovirus type 32 virus-associated RNA pre-terminal protein (pTP) and 52,55 K protein genes, partial cds. | CGCUCGCGCCCCUAGUCUCCACAACCAUCGCCACGGUUGA GUCGCGGCAGAACCCGGUUCGAGCACGGCCGCGGCGAGCG GCACUUCGUCACCCCGCCGAUUUAAAGACCCACAGCCAGC CGACUUCUCCAGUUACGGGAGCGAGCCCCC | 69 |
| U52552 | 115 | 274 | Human adenovirus type 33 | Human adenovirus type 33 virus-associated RNA pre-terminal protein (pTP) and 52,55 K protein genes, partial cds. | GGCUCUUCCUCCGUAGCCUGGCGGAACGCAAACGGGUUAG GCCGCGUGUGUACCCCGGUUCGAGUCCCCUCGAAUCAGGC UGGAGCCGCGACUAACGUGGUAUUCGCACUCCCGUCUCGA CCCGAGCCCGAUAGCCGCCAGGAUACGGCGGAGAGCCCUU | 70 |
| U52552 | 333 | 482 | Human adenovirus type 33 | Human adenovirus type 33 virus-associated RNA pre-terminal protein (pTP) and 52,55 K protein genes, partial cds. | GGCUCGCGCCCGUAGUCUGGAGAAGCAUCGCCAGGGUUGA GUCGCGGCAGAACCCGGUUCGCGCACGGCCGCGGCGAGCG GGACUUGGUCACCCCGCCGAUUUAAAGACCCACAGCCAGC CGACUUCUCCAGUUACGGGAGCGAGCCCCC | 71 |
| U52553 | 115 | 274 | Human adenovirus type 37 | Human adenovirus type 37 virus-associated RNA pre-terminal protein (pTP) and 52,55 K protein genes, partial cds. | GGCUCUUCCUCCGUAGCCUGGCGGAACGCAAACGGGUUAG GCCGCGUGUGUACCCCGGUUCGAGUCCCCUCGAAUCAGGC UGGAGCCGCGACUAACGUGGUAUUCGCACUCCCGUCUCGA CCCAAGCCCGAUAGCCGCCAGGAUACGGCGGAGAGCCCUU | 72 |
| U52553 | 333 | 482 | Human adenovirus type 37 | Human adenovirus type 37 virus-associated RNA pre-terminal protein (pTP) and 52,55 K protein genes, partial cds. | GGCUCGCGCCCGUAGUCUCGAGAAGCAUCGCCAGGGUUGA CUCGCGGCAGAACCCGCUUCAAGGACGGCCGCGGCGAGCG CGACUUGCUCACCCCGCCGAUUUAAAGACCCACAGCCAGC CGACUUCUCCAGUUACGGCAGCGAGCCCCC | 73 |
| U52554 | 115 | 274 | Human adenovirus type 39 | Human adenovirus type 39 virus-associated RNA pre-terminal protein (pTP) and | CGCUCUUCCUCCGUAGCCUGGCGGAACGCAAACGGGUUAG GCCGCGCGUGUACCCCGGUUCGAGUCCCCUCGAAUCAGGC UGGAGCCGCGACUAACGUGGUAUUGGCACUCCCGUCUCGA | 74 |

| EMBL accession | Start | End | Species | Description | Sequence | SEQ ID NO: |
|---|---|---|---|---|---|---|
| | | | | 52,55 K protein genes, partial cds. | CCCGAGCCCGAUAGCCGCCAGGAUACGGCGGAGAGCCCUU | |
| U52554 | 333 | 482 | Human adenovirus type 39 | Human adenovirus type 39 virus-associated RNA pre-terminal protein (pTP) and 52,55 K protein genes, partial cds. | GGCUCGCGCCCGUAGUCUGGAGAAGCAUCGCCAGGGUUGA GUCGCGGCAGAACCCGGUUCGAGCACGGCCGCGGCGAGCG GACUUGGUCACCCCGCCGAUUUAAAGACCCACAGCCAGC CGACUUCUCCAGUUACGGGAGCGAGCCCCC | 75 |
| U52555 | 115 | 274 | Human adenovirus type 36 | Human adenovirus type 36 virus-associated RNA pre-terminal protein (pTP) and 52,55 K protein genes, partial cds. | GGCUCUUCCUCCGUAGCCUGGCGGAACGCAAACGGGUUAG GCCGCGUGUGUACCCCGGUUCGAGUCCCCUCGAAUCAGGC UGGAGCCCCGACUAACGUGGUAUUGGCACUCCCGUCUCGA CCCGAGCCCGAUAGCCGCCAGGAUACGGCGGAGAGCCCUU | 76 |
| U52555 | 333 | 482 | Human adenovirus type 36 | Human adenovirus type 36 virus-associated RNA pre-terminal protein (pTP) and 52,55 K protein genes, partial cds. | GGCUCGCGCCCGUAGUCUGGAGAAGCAUCGCCAGGGUUGA GUCGCGGCAGAACCCGGUUCGCGGACGGCCGCGGCGAGCG GGACUUGGUCACCCCGCCGAUUUAAAGACCCACAGCCAGC CGACUUCUCCAGUUACGGGAGCGAGCCCCC | 77 |
| U52556 | 115 | 274 | Human adenovirus type 42 | Human adenovirus type 42 virus-associated RNA pre-terminal protein (pTP) and 52,55 K protein genes, partial cds. | GGCUCUUCCUCCGUAGCCUGGCGGAACGCAAACGGGUUAG GCCGCGUGUCUACCCCGGUUCGAGUCCCCUCGAAUCAGGC UGGAGCCGCGACUAACGUGGUAUUGGCACUCCCGUCUCGA CCCGAGCCCGAUAGCCGCCAGGAUACGGCGGAGAGCCCUU | 78 |
| U52556 | 333 | 482 | Human adenovirus type 42 | Human adenovirus type 42 virus-associated RNA pre-terminal protein (pTP) and 52,55 K protein genes, partial cds. | GGCUCGCGCCCGUAGUCUGGAGAAGCAUCGCCAGGGUUGA GUCGCGGCAGAACCCGGUUCGCGGACGGCCGCGGCGAGCG GGACUUGGUCACCCCGCCGAUUUAAAGACCCACAGCCAGC CGACUUCUCCAGUUACGGGAGCGAGCCCCC | 79 |
| U52557 | 115 | 274 | Human adenovirus type 43 | Human adenovirus type 43 virus-associated RNA pre-terminal protein (pTP) and 52,55 K protein genes, partial cds. | GGCUCUUCCUCCGUAGCCUGGCGGAACGCAAACGGGUUAG GCCGCGUGUGUACCCCGGUUCGAGUCCCCUCGAAUCAGGC GGAGCCGCGACUAACGUGGUAUUGGCACUCCCGUCUCGA CCCGAGCCCGAUAGCCGCCAGGAUACGGCGGAGAGCCCUU | 80 |
| U52557 | 333 | 482 | Human adenovirus type 43 | Human adenovirus type 43 virus-associated RNA pre-terminal protein (pTP) and 52,55 K protein genes, partial cds. | GCCUCGCGCCCGUAGUCUGGAGAAGCAUCGCCAGGGUUGA GUCGCGGCAGAACCCGGUUCGCGGACGGCCGCGGCGAGCG GGACUUGGUCACCCCGCCGAUUUAAAGACCCACAGCCAGC CGACUUCUCCAGUUACGGGAGCGAGCCCCC | 81 |

| EMBL accession | Start | End | Species | Description | Sequence | SEQ ID NO: |
|---|---|---|---|---|---|---|
| U52558 | 115 | 274 | Human adenovirus type 44 | Human adenovirus type 44 virus-associated RNA pre-terminal protein (pTP) and 52,55 K protein genes, partial cds. | GGCUCUUCCUCCGUAGCCUGGCGGAACGCAAACGGGUUAG CCGCGUGUGUACCCCGGUUCGACUCCCCUCGAAUCAGGC UGGAGCCGCGACUAACGUGGUAUUGGCACUCCCGUCUCGA CCCGAGCCCGAUAGCCGCCAGGAUACGGCGGAGAGCCCUU | 82 |
| U52558 | 333 | 482 | Human adenovirus type 44 | Human adenovirus type 44 virus-associated RNA pre-terminal protein (pTP) and 52,55 K protein genes, partial cds. | GGCUCGCGCCCGUAGUCUGGAGAAGCAUCGCCAGGGUUGA GUCGCGGCAGAACCCGGUUCGAGGACGGCCGCGGCGAGCG GACUUGGUCACCCCGCCGAUUUAAAGACCCACAGCCAGC CGACUUCUCCAGUUACGGGAGCGAGCCCCC | 83 |
| U52559 | 115 | 274 | Human adenovirus type 45 | Human adenovirus type 45 virus-associated RNA pre-terminal protein (pTP) and 52,55 K protein genes, partial cds. | GGCUCUUCCUCCGUAGCCUGGCGGAACGCAAACGGGUUAG GCCGCGUGUACCCCGGUUCGAGUCCCCUCGAAUCAGGC UGGAGCCGCGACUAACGUGGUAUUGGCACUCCCGUCUCGA CCCGAGCCCGAUAGCCGCCAGGAUACGGCGGAGAGCCCUU | 84 |
| U52559 | 333 | 482 | Human adenovirus type 45 | Human adenovirus type 45 virus-associated RNA pre-terminal protein (pTP) and 52,55 K protein genes, partial cds. | GGCUCGCGCCCGUAGUCUGGAGAAGCAUCGCCAGGGUUGA GUCGCGGCAGAACCCGGUUCGAGGACGGCCGCGGCGAGCG GACUUGGUCACCCCGCCGAUUUAAAGACCCACAGCCAGC CGACUUCUCCAGUUACGGGAGCGAGCCCCC | 85 |
| U52560 | 115 | 274 | Human adenovirus type 46 | Human adenovirus type 46 virus-associated RNA pre-terminal protein (pTP) and 52,55 K protein genes, partial cds. | GGCUCUUCCUCCGUAGCCUGGCGGAACGCAAACGGGUUAG GCCGCGUGUGUACCCCGGUUCGAGUCCCCUCGAAUCAGGC UGGAGCCGCGACUAACGUGGUAUUGGCACUCCCGUCUCGA CCCAAGCCCGAUAGCCGCCAGGAUACGGCGGAGAGCCCUU | 86 |
| U52560 | 333 | 482 | Human adenovirus type 46 | Human adenovirus type 46 virus-associated RNA pre-terminal protein (pTP) and 52,55 K protein genes, partial cds. | GGCUCGCGCCCGUAGUCUGGAGAAGCAUCGCCAGGGUUGA GUCGCGGCAGAACCCGGUUCGAGGACGGCCGCGGCGAGCG GACUUGGUCACCCCGCCGAUUUAAAGACCCACAGCCAGC CGACUUCUCCAGUUACGGGAGCGAGCCCCC | 87 |
| U52561 | 115 | 274 | Human adenovirus type 47 | Human adenovirus type 47 virus-associated RNA pre-terminal protein (pTP) and 52,55 K protein genes, partial cds. | GGCUCUUCCUCCGUAGCCUGGCGGAACGCAAACGGGUUAG GCCGCGUGUACCCCGGUUCGAGUCCCCUCGAAUCAGGC UGGAGCCGCGACUAACGUGGUAUUGGCACUCCCGUCUCGA CCCGAGCCCGAUAGCCGCCAGGAUACGGCGGAGAGCCCUU | 88 |
| U52561 | 333 | 482 | Human adenovirus type 47 | Human adenovirus type 47 virus-associated RNA pre-terminal protein (pTP) and 52,55 K protein genes, partial cds. | GGCUCGCGCCCGUAGUCUGGAGAACCAUCGCCAGGGUUGA GUCGCGACAGAACCCGGUUCGCGGACGGCCGCGGCGAGCG GACUUGGUCACCCCGCCGAUUUAAAGACCCACAGCCAGC | 89 |

-continued

| EMBL accession | Start | End | Species | Description | Sequence | SEQ ID NO: |
|---|---|---|---|---|---|---|
| | | | | 52,55 K protein genes, partial cds. | CGACUUCUCCAGUUACGGGAGCGACCCCCC | |
| U52562 | 115 | 274 | Human adenovirus type 38 | Human adenovirus type 38 virus-associated RNA pre-terminal protein (pTP) and 52,55 K protein genes, partial cds. | GCCUCUUCCUCCGUAGCCUGGCGGAACGCAAACGGGUUAG GCCGCGUGUGUACCCCGGUUCGAGUCCCCUCGAAUCAGGC UGGAGCCGCGACUAACGUGGUAUUGGCACUCCCGUCUCGA CCCGAGCCCGAUAGCCGCCAGGAUACGGCGGAGAGCCCUU | 90 |
| U52562 | 332 | 481 | Human adenovirus type 38 | Human adenovirus type 38 virus-associated RNA pre-terminal protein (pTP) and 52,55 K protein genes, partial cds. | GGCUCGCGCCCGUAGUCUGGAGAAGCAUCGCCAGGGUUGA GUCGCGGCAGAACCCGGUUCGCGGACGGCCGCGGCGAGCG GGACUUGGUCACCCCGCCGAUUUAAAGACCCACAGCCAGC CCACUUCUCCAGUUACGGGAGCGAGCCCCC | 91 |
| U52563 | 115 | 274 | Human adenovirus type 8 | Human adenovirus type 8 virus-associated RNA pre-terminal protein (pTP) and 52,55 K protein genes, partial cds. | GGCUCUUCCUCCGUAGCCUGGCGGAACGCAAACGGGUUAG GCCGCGCGUGUACCCCGGUUCCAGUCCCCUCGAAUCAGGC UAAAGCCGCGACUAACGUGGUAUUGGCACUCCCGUCUCGA CCCAAGCCCGAUAGCCGCCAGGAUACGGUGAAGAGCCUUU | 92 |
| U52563 | 332 | 481 | Human adenovirus type 8 | Human adenovirus type 8 virus-associated RNA pre-terminal protein (pTP) and 52,55 K protein genes, partial cds. | GGCUCGCGCCCGUAGUCUGGACAAGCAUCACUAGGGUUAA GUUACAGCAGAACCCGGUUCGCGGACGGCCGCGGCAAGCG GGACUUAGUUACCCCGCCAAUUUAAAGACCCGCAGCCAGC CGACUUUUCCAGUUACGGGAGCGAGCCCCC | 93 |
| U52564 | 119 | 278 | Human adenovirus type 16 | Human adenovirus type 16 virus-associated RNA pre-terminal protein (pTP) and 52,55 K protein genes, partial cds. | GGCUCGUCUCCGUGGCCUGGAGGCuAAGCGAACGGGUUGG GCUGCGCGUGUACCCCGGUUCGAAUCUCGGAUCAGGCUGG GCCCCAGCUAACGUGGUACUGGCACUCCCGUCUCGACCC AGGCCUGCACAAAACCUCCAGGAUACGGAGGCGGGUCGUU | 94 |
| U52564 | 354 | 525 | Human adenovirus type 16 | Human adenovirus type 16 virus-associated RNA pre-terminal protein (pTP) and 52,55 K protein genes, partial cds. | GGCUCGCGCCCGUAGUCUGGAGAAuCAAUCGCCAGGGUUG CGUUGCGGUGUGCCCCGGUUCGAGUCuUAGCGCGCCGGAU CGGCCGGUUUCCGCGACAAGCGAGCGUUUGGCAGCCUCGU CAUUUCUAAGACCCCGCCAGCCGACUUCUCCAGUUUACGG GAGCGAGCCCUC | 95 |
| U52565 | 119 | 278 | Human adenovirus type 21 | Human adenovirus type 21 virus-associated RNA pre-terminal protein (pTP) and 52,55 K protein genes, partial cds. | GGCUCGUCUCCGUGGCCUGGAGGCuAAGCGAACGGGUUGG GCUGCGCGUGUACCCCGGUUCGAAUCUCGGAUCAGGCUGG AGCCGCAGCUAACGUGGUACUGGCACUCCCGUCUCGACCC AGGCCUGCACAAAACCUCCAGGAUACGGAGGCGGGUCGUU | 96 |

-continued

| EMBL accession | Start | End | Species | Description | Sequence | SEQ ID NO: |
|---|---|---|---|---|---|---|
| U52565 | 354 | 525 | Human adenovirus type 21 | Human adenovirus type 21 virus-associated RNA pre-terminal protein (pTP) and 52,55 K protein genes, partial cds. | GGCUCGCGCCCGUAGUCUGCAGAAuCAAUCGCCAGGGUUG CGUUGCGGUGUGCCCCGGUUCGAGUCuUAGCGCGCCGGAU CGGCCGGUUUCCGCGACAAGCGAGGGUUUGGCAGCCCCGU CAUUUCUAAGACCCCGCCAGCCGACUUCUCCAGUUUACGG GAGCGAGCCCUC | 97 |
| U52566 | 115 | 274 | Human adenovirus type 10 | Human adenovirus type 10 virus-associated RNA pre-terminal protein (pTP) and 52,55 K protein genes, partial cds. | GGCUCUUCCUCCGUAGCCUGGCGGAACGCAAACGGGUUAG GCCGCGUGUGUACCCCGGUUCGAGUCCCCUCGAAUCAGGC UGGAGCCGCGACUAACGUGGUAUUGGCACUCCCGUCUCGA CCCGAGCCCGAUAGCCGCCAGGAUACGGCGGAGAGCCCUU | 98 |
| U52566 | 332 | 454 | Human adenovirus type 10 | Human adenovirus type 10 virus-associated RNA pre-terminal protein (pTP) and 52,55 K protein genes, partial cds. | GGCUCGCGCCCGUAGUCUGGAGAAGCAUCGCCAGGGUUGA GUCGCGGCGAGCGGGACUUGGUCACCCCGCCGAUUUAAAG ACCCACAGCCAGCCGACUUCUCCAGUUACGGGAGCGAGCC CCC | 99 |
| U52569 | 118 | 276 | Human adenovirus type 11 | Human adenovirus type 11 virus-associated RNA pre-terminal protein (pTP) and 52,55 K protein genes, partial cds. | GACUCGACUCCGUAGCCUGGAGGAACGUGAACGGGUUGGG UCGCGGUCUACCCCGGUUCGAGACUUGUACUCGAGCCGGC CGGAGCCGCGGCUAACGUGGUAUUGGCACUCCCGUCUCGA CCCAGCCUACAAAAAUCCAGGAUACGGAAUCGAGUCGUU | 100 |
| U52570 | 118 | 276 | Human adenovirus type 14 | Human adenovirus type 14 virus-associated RNA pre-terminal protein (pTP) and 52,55 K protein genes, partial cds. | GACUCGACUCUGUAGCCUGGAGGAACGUGAACGGGUUGGG UCGCGGUGUACCCCGGUUCAAGACUUGUACUCGAGCCGGC CGGAGCCGCGGCUAACGUGGUAUUCGCACUCCCGUCUCGA CCCAGCCUACAAAAAUCCAGGAUACGGAAUCGAGUCGUU | 101 |
| U52571 | 118 | 276 | Human adenovirus type 34 | Human adenovirus type 34 virus-associated RNA pre-terminal protein (pTP) and 52,55 K protein genes, partial cds. | GACUCGACUCCGUAGCCUGGAGGAACGUGAACGGGUUGGG UCGCGGUGUACCCCGGUUCGAGACUUGUACUCGAGCCGGC CCGAGCCGCGGCUAACGUGGUAUUGGCACUCCCGUCUCGA CCCAGCCUACAAAAAUCCAGGAUACGGAAUCGAGUCGUU | 102 |
| U52572 | 118 | 276 | Human adenovirus type 35 | Human adenovirus type 35 virus-associated RNA pre-terminal protein (pTP) and 52,55 K protein genes, partial cds. | GACUCGACUCCGUAGCCUGGAGGAACGUGAACGGGUUGGG UCGCGGUGUACCCCGCUUCGAGACUUGUACUCGAGCCGGC CGGAGCCGCGGCUAACGUGGUAUUGGCACUCCCGUCUCGA CCCAGCCUACAAAAAUCCACGAUACGCAAUCGAGUCGUU | 103 |
| U52573 | 114 | 285 | Human adenovirus type 41 | Human adenovirus type 41 virus-associated RNA pre-terminal protein (pTP) and | GACUCUUCUCCGUAGCCUGGACCAuaGACCGCCAGGGUGC GGUGGCGAACAACCCCGCUUCGACACCGGCUGGAUCCGC CACUCCCGACGCGCCGGCCCCguqucCACGACGGAAACCC | 104 |

-continued

| EMBL accession | Start | End | Species | Description | Sequence | SEQ ID NO: |
|---|---|---|---|---|---|---|
| | | | | 52,55 K protein genes, partial cds. | CGCCCACACCUAGCCGCGGUCCccggaUCUCCAGAUACGG AGGCGAGAUCUU | |
| U52574 | 118 | 289 | Human adenovirus type 7 | Human adenovirus type 7 virus-associated RNA pre-terminal protein (pTP) and 52,55 K protein genes, partial cds. | CGCUCGACUCCGUGGCCUGGGGGAACGUGAACGGGUUGGG CGCCGUGUACCCCGGUUCGAGUCcaaagcuaagcaAUCA CACUCGGAUCGGCCGGAGCCGCGGCUAACGUGGUAUUGGC UAUCCCUCUCCACCCACCCCACCAAUAUCCAGGGUACGG AGUAGAGUCGUU | 105 |
| U52574 | 363 | 537 | Human adenovirus type 7 | Human adenovirus type 7 virus-associated RNA pre-terminal protein (pTP) and 52,55 K protein genes, partial cds. | CCCUCGCCCCCUAGUCUCCAGAAuCAGUCCCCAGGGUUG CCUUGCGGUAUGCCCCcGGUUCGAGCCuaaGCGCGGCUCG UAUCGCCCGGUUUCCCCGACAAGCGAGGCUUUGCCAGCCC ACUCAUUUCCAAGACCCCCCCAGCCGACUUCUCCAGUUUA CGGGAGCGAGCCCUU | 106 |
| X03000 | 10423 | 10594 | Human adenovirus type 7 | Adenovirus type 7 genome left end (0.0 to 31%). | GCCUCGACUCCGUGGCCUGGGGGAACGUGGACGGGUUGGG UCGCGGUGUACCCCGGUUCGACUCcaaagcuaagcaAUCA CACUCGGAUCGGCCGGAGCCGCGGCUAACGUGGUAUUGGC UAUCCCGUCUCGACCCAGCCGACGAAUAUCCAGGGUACGG AGUAGAGUCGUU | 107 |
| X03000 | 10668 | 10842 | Human adenovirus type 7 | Adenovirus type 7 genome left end (0.0 to 31%). UAUCGGCCGGUUUCCGCGACAAGC-GAGGGUUUGGCAGCCC | GGCUCGCGCCCGUAGUCUGGAGAAuCAGUCGCCAGGGUUG CGUUGCGGUAUGCCCCcGGUUCGAGCCuaaGCGCGGCUCG

AGUCAUUUCCAAGACCCCGCCAGCCGACUUCUCCAGUUUA CGGGAGCGAGCCCUU | 108 |

The VA RNA sequences set forth in Table 1 (and derivatives thereof) have utility as substrates and/or inhibitors as described herein. Corresponding VA RNA gene sequences (e.g., having utility, either in their entirety or in part, as vector sequences) can be found in the EMBL Nucleotide Sequence Database using the Accession Nos. set forth in the Table.

B. Structural Non-Coding RNAs of Other Virus Families

Numerous viral families in addition to the adenoviridae family encode structural non-coding RNAs that bear resemblance to miRNA precursors (see FIG. 1; examples are set forth in Table 2). Of particular interest are viruses encoding structural RNAs produced by RNA polymerase III transcription, and viruses encoding larger RNAs with a high degree of secondary structure, such as internal ribosome entry sites (IRES).

Several members of the herpesviridae family are known to encode structural non-coding RNAs. For example, the gamma herpesvirus Epstein-Barr virus (EBV) produces short structured RNAs, termed Epstein-Barr virus encoded RNAs (EBERs). EBV EBERs have a high degree of sequence similarity to the VA RNAs, can interact with PKR and are able to partially complement ΔVA RNA$_I$/VA RNA$_{II}$ adenovirus replication (1). Similarly, another gammma herpesvirus, herpesvirus papio (HVP), encodes two EBER-like RNAs, HVP-1 and HVP-2. These RNAs are transcribed in a similar fashion to the EBV EBERs and have been shown to hybridize to EBERs (23). The murine gammaherpes virus 68 encodes a family of eight short RNA polymerase III transcripts that are expressed during latency. These transcripts produce short tRNA-like strictures (24). Yet another herpesvirus, the Human Cytomegalovirus (HCMV), encodes an RNA polymerase III transcript termed HCMV-encoded ribonucleic acid (CMER) (25). In another example, Karoposi's Sarcoma-associated herpesvirus (KSHV) encodes an abundant 1.2-kb non-coding RNA that has been termed polyadenylated nuclear RNA (PAN RNA, also called nut-1 or T1.1). PAN RNA is strongly induced during early lytic cycle activation of KSHV (31). The ability of VA RNAs and, at least, the EBERs to interact with the dsRNA-binding enzyme PKR, coupled with the structural similarity between these viral non-coding RNAs and miRNA precursors, suggests that these pol-III-transcribed viral RNAs may act as substrates or inhibitors of the RNAi pathway, potentially by interacting with Dicer or RISC.

Other viral families also encode structural non-coding RNAs in untranslated regions of their genomes. These structural RNAs have had a variety of functions ascribed to them, such as sites of translation initiation and transcriptional regulation. For example, the human immunodeficiency virus (HIV) contains at least two such RNAs in its genome, the rev responsive element (RRE) and the TAR sequence. The RRE has a complex secondary structure containing five stem loops. Interaction of the viral protein rev with the RRE temporally regulates viral transcription. Similarly, the TAR sequence, which encodes a stem loop structure in the 5' long terminal repeat (LTR) region of the virus, interacts with a viral regulatory gene, tat, to increase viral RNA accumulation. Interestingly, like the Adenovirus VA RNAs and EBV EBERs, the TAR sequence has been shown to interact with PKR. Other members of the lentivirus and retrovirus families encode elements similar to the TAR and/or RRE sequences (1, 26).

A variety of viral families, e.g., Flaviviridae, Picornaviridae, and Herpesviridae, encode long, structured RNA sequences referred to as IRES sequences. To date, the main function ascribed to these sequences is the ability to direct translational machinery to the viral transcripts in the absence of a 5' cap structure. However, given their structural similarity to miRNAs, these multi-stem loop structures may be substrates for Dicer or the RNAi pathway. A variety of viruses utilize IRES sequences. These virus families include clinically relevant pathogens, e.g., Hepatitis C Virus (HCV), Dengue Virus, Foot and Mouth Disease Virus, Kaposis Sarcoma-Associated Herpesvirus (KSHV), and Poliovirus (1, 27-29).

In particular, the flaviviridae viruses demonstrates a high degree of secondary structure in their viral genomes. Of particular relevance, the flaviviridae family of viruses additionally encodes structured nontranslated RNA in the 3' untranslated region (UTR) (37). This virus family is subdivided into the three genera *Flavivirus, Pestivirus* and *Hepacivirus*, and the group of GB virus C/hepatitis G virus, with a currently uncertain taxonomic classification. Of these groups, there are two subgroups, namely the genus *Flavivirus*, with its type I cap structure at the 5' UTR and a highly structured 3' UTR, and the remaining three groups, which exhibit translation control by means of an IRES in the 5' UTR and a much shorter, less-structured 3' UTR. In particular, the Hepatitis C Virus encodes a 3' nontranslated RNA signal from the 3' UTR that is required for replication of the virus, and mutational analysis suggests that the secondary structure and/or sequence is important for virus survival (35). The highly structured 3' nontranslated RNAs generated by the flaviviridae family may bear resemblance to miRNA precursors. Accordingly, the 3' nontranslated RNAs generated by the viruses of the flaviviridae family may have utility as substrates and/or inhibitors of the RNAi pathway as described herein.

As yet another example, the vaccinia virus of the Poxyiridae family produces a group of small, nontranslated, polyadenylylated RNAs, termed POLADS, produced during the early part of virus infection. POLADS are associated with the selective inhibition of host protein synthesis, and the inhibitory function appears to be associated with the poly(A) tail of these small RNAs (30).

As set forth above, numerous viruses encode untranslated RNA sequences containing a high degree of secondary structure (examples are set forth in Table 2). In many instances, these stem-loop RNAs bear structural similarity to miRNA precursors processed by Dicer. Given the discoveries set forth herein regarding VA RNAs, and considering the structural similarity between these untranslated viral RNA structures and miRNA precursors, these viral RNAs may be substrates and/or inhibitors of the RNAi pathway.

The above virally encoded structured RNAs (e.g., svRNAs) are proposed to function as substrates for the RNAi pathway and become processed to produce siRNA or miRNA-like molecules that function to control viral and/or host cell gene expression. Accordingly, it is within the scope of the invention to provide svRNAs (or derivatives thereof) to cells and/or organisms to mediate (e.g., induce) RNAi. It is also envisioned by the instant inventors that such viral RNAs are incorporated into RISC or a Dicer-containing complex and thereby compete with alternate substrates for the RNAi pathway. Such a competition mechanism could be an important virulence factor for the viruses, and disabling this viral capacity would be an important factor in the creation of a vaccine. Accordingly, it is also within the scope of the present invention to provide methods for identifying new antiviral agents by identifying agents that affect the ability of viral structured RNAs to act as competitors of RNAi in a cell. Additionally, identification of modulators of svRNA-mediated RNAi would have important clinical and commercial research applications, in situations where the gene targeted by RNAi is important, for example, in maintaining or modulating cellular homeostasis, regulating cellular proliferation, and the like. Also within the scope of the instant invention are delivery vehicles, e.g., expression cassettes, plasmids, or viral-based vectors, encoding such virally encoded structured RNAs, or portions thereof, having alterations in these sequences in order to produce desired miRNA or siRNA-like molecules. Such delivery vehicles would provide highly efficient transduction systems to regulate genes of interest, e.g. cellular or viral genes.

III. miRNAs, siRNAs, miRNA-Like and siRNA-Like Molecules

MicroRNAs (miRNAs) are small (e.g., 19-25 nucleotides), single-stranded noncoding RNAs that are processed from ~70 nucleotide hairpin precursor RNAs by Dicer. siRNAs are of a similar size and are also non-coding, however, siRNAs are processed from long dsRNAs and are usually double stranded (e.g., endogenous siRNAs). miRNAs can pair with target miRNAs that contain sequences only partially complementary (e.g., 30%, 35%, 40%, 45%, 50%, 55%, 60%, 65%, 70%, 75%, 80% or more) to the miRNA. Such pairing results in repression of mRNA translation without altering mRNA stability. Recently, it has also been demonstrated that miRNAs are capable of mediating RNAi (Hutvágner and Zamore (2002) *Science* 297: 2056-2060). As expression of the precursor RNAs (i.e., pre-miRNAs) is often developmentally regulated, miRNAs are often referred to interchangeably in the art as "small temporal RNAs" or "stRNAs".

*C. elegans* contains approximately 100 endogenous miRNA genes, about 30% of which are conserved in vertebrates. The present inventors have demonstrated that certain structured viral RNAs (e.g., svRNAs) can be processed by Dicer (or a homologue or orthologue thereof) into small RNAs capable of mediating RNAi. Such svRNA-derived, small RNAs are, accordingly, referred to herein as miRNA like (in instances where the active RNA is single stranded) or siRNA-like (in instances where the active RNA is double stranded).

IV. Experimental Applications

As described herein, svRNAs have utility as substrates and/or inhibitors of RNAi. Moreover, the present invention provides methods for identifying the targets of svRNAs (e.g., VA-RNAs). svRNAs (and/or RNA agents derived therefrom) as well as VA-RNA targets can further be used experimentally, for example, in creating knockout and/or knockdown cells or organisms, in functional genomics and/or proteomics applications, in screening assays, and the like.

A. Screening Assays

In one aspect of the invention, svRNAs (and/or RNA agents derived therefrom) as well as svRNA targets, as identified herein, are suitable for use in methods to identify and/or characterize potential pharmacological agents, e.g. identifying new pharmacological agents from a collection of test substances and/or characterizing mechanisms of action and/or side effects of known pharmacological agents.

1. svRNAs as Substrates of RNAi

Viral structured non-coding RNAs (e.g., svRNAs) can function as substrates for the RNAi pathway and become processed to produce siRNA or miRNA-like molecules that may function to control viral and/or host cell gene expression. Accordingly, in one embodiment, the invention features a system for identifying and/or characterizing pharmacological agents acting on, for example, a svRNA:target RNA pair comprising: (a) a cell capable of expressing the target RNA, (b) at least one svRNA molecule (or RNA agent derived therefrom) capable of modulating (e.g., inhibiting) the expression of said target RNA, and (c) a test substance or a collection of test substances wherein pharmacological properties of said test substance or said collection are to be identified and/or characterized. In another embodiment, the invention features a system for identifying and/or characterizing pharmacological agents acting on, for example, a svRNA:target RNA pair comprising: (a) an organism (e.g., a non-human eukaryotic organism) capable of expressing the target RNA, (b) at least one svRNA molecule (or RNA agent derived therefrom) capable of modulating (e.g., inhibiting) the expression of said target RNA, and (c) a test substance or a collection of test substances wherein pharmacological properties of said test substance or said collection are to be identified and/or characterized.

Preferred cells for use in the screening assays of the invention are eukaryotic cells, although screening in prokaryotic cells is also contemplated. In one embodiment, the cell is a plant cell. In another embodiment, the cell is an insect cell. In yet another embodiment, the cell is a mammalian cell (e.g., a human or murine cell). In yet another embodiment, the cell is an avian cell. Preferred organisms for use in the screening assays of the invention include lower organisms, for example, C. elegans. Test substances are contacted with the cell or organism capable of expressing the target RNA (i.e., the test cell or organism, respectively) before, after or simultaneously with the svRNA agent.

Cells or organisms are assayed, for example, for an indicator of RNAi. As used herein, the phrase "indicator of RNAi" refers to any detectable marker, readout, etc. which is indicative of RNAi activity or an RNAi process occurring in said cell or organism. Levels of substrates or products of an RNAi process are preferred indicators. For example, in instances where a svRNA is a substrate for an RNAi process, levels (e.g., decreasing levels) of svRNA are indicative of RNAi. Alternatively, levels (e.g., increasing levels) of miRNA- or siRNA-like molecules are indicative of siRNA-like molecules. In another embodiment, levels of intermediate products (e.g., small duplex RNA) are indicative of RNAi. Other preferred indicators include levels of target RNA (e.g., target mRNA) and/or levels of protein encoded by a target mRNA. The latter, for example, can be indicative of target cleavage (i.e., a siRNA or miRNA-like function) and/or translational repression (i.e., a mi-RNA-like function). In certain embodiments, one or more substrate, product, intermediate, etc. is labeled (e.g., enzymatically, fluorescently or radioisotypically labeled) to facilitate detection. Enzymatically labeled reagents are often assayed in the presence of a variety of colorimetric substances. Indirect assays, for example, reporter gene assays sensitive to levels of proteins encoded by target mRNAs, are also suitable as indicators of RNAi. In preferred embodiments, a system as described above can further comprise suitable controls.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12: 145). The test compounds of the present invention can be obtained using nucleic acid libraries, e.g., complementary DNA libraries (see S. Y. Sing (2003) Methods Mol Biol 221: 1-12), DNA or RNA aptamer libraries (see C. K. O'Sullivan 2002 Anal Bioanal Chem 372(1): 44-48; J. J. Toulme 2000 Curr Opin Mol Ther 2(3): 318-24; J. J. Toulme et al., 2001 Prog Nucleic Acid Res Mol Biol 69: 1-46) and by using in vitro evolution approaches, e.g., in vitro evolution of nucleic acids (see, e.g., J. A. Bittker et al. 2002 Curr Opin Chem Biol 6(3): 367-374).

Examples of methods for the synthesis of molecular libraries can be found in the art, for example in: DeWitt et al. (1993) Proc. Natl. Acad. Sci. U.S.A. 90: 6909; Erb et al. (1994) Proc. Natl. Acad. Sci. USA 91: 11422; Zuckermann et al. (1994). J. Med. Chem. 37: 2678; Cho et al. (1993) Science 261: 1303; Carrell et al. (1994) Angew. Chem. Int. Ed. Engl. 33: 2059; Carell et al. (1994) Angew. Chem. Int. Ed. Engl. 33: 2061; and in Gallop et al. (1994) J. Med. Chem. 37: 1233.

Libraries of compounds may be presented in solution (e.g., Houghten (1992) Biotechniques 13: 412-421), or on beads (Lam (1991) Nature 354: 82-84), chips (Fodor (1993) Nature 364: 555-556), bacteria (Ladner U.S. Pat. No. 5,223,409), spores (Ladner U.S. Pat. No. '409), plasmids (Cull et al. (1992) Proc Natl Acad Sci USA 89: 1865-1869) or on phage (Scott and Smith (1990) Science 249: 386-390); (Devlin (1990) Science 249: 404-406); (Cwirla et al. (1990) Proc. Natl. Acad. Sci. 87: 6378-6382); (Felici (1991) J. Mol. Biol. 222: 301-310); (Ladner supra.)).

In a preferred embodiment, the library is a natural product library, e.g., a library produced by a bacterial, fungal, or yeast culture. In another preferred embodiment, the library is a synthetic compound library.

Compounds or agents identified according to such screening assays can be used therapeutically or prophylactically either alone or in combination, for example, with an svRNA (or derivative thereof) of the invention, as described supra.

In another embodiment of the invention, a system is featured for identifying and/or characterizing a druggable target, for example, a cellular or viral gene, comprising: (a) an assay composition comprising an RNAi pathway molecule and a svRNA (or RNA agent derived therefrom), (b) assaying for expression of a candidate RNA, wherein a change in expression of the candidate RNA indicates that a gene or protein corresponding to the RNA is a druggable target. In a related embodiment, the invention features a system for identifying and/or characterizing a druggable target, for example, a cellular or viral gene, comprising: (a) a cell or organism comprising an RNAi pathway molecule and a svRNA (or RNA agent derived therefrom), (b) assaying for expression of a candidate RNA, wherein a change in expression of the candidate RNA indicates that a gene or protein corresponding to the RNA is a druggable target.

Candidate target RNAs of svRNAs can be identified by using methodologies commonly known to the skilled artisan. For example, computer algorithms can be used to search a host genome for sequences of homology to a svRNA sequence. Preferably, a svRNA sequence having homology to a host genome is located within a duplex, e.g., stem region, of the svRNA. In preferred embodiments of this approach to identifying target RNAs of svRNAs, genome sequences are searched for sequences having at least about 50%, 60%, 70%, 80%, 90% or 100% homology to the svRNA sequence. In other embodiments of this approach to identifying target RNAs of svRNAS, genome sequences are searched for sequences having at least about 30%, 40%, 45% or more homology to the svRNA sequence. Another approach to identify candidate target RNAs of svRNAs is the use of solid-based nucleic acid arrays, e.g, DNA and/or RNA arrays or "chips", to identify genes whose expression is changed upon svRNA expression, e.g., upon viral infection, in a cell or organism. Solid-based nucleic acid array technologies are well known to those skilled in the relevant art. The svRNA can be expressed in the cell or organism from e.g., a virus, viral-derived vector, plasmid, transgene, and the like. In this approach, gene expression in the presence of svRNA expression can be measured and compared, for example, to gene expression in the absence of svRNA expression or to gene expression in the presence of a svRNA that has been modified so that the siRNA- or miRNA-like molecule generated from the svRNA is inactivated. In cases where the svRNA is known or suspected to play a role in a particular function, e.g., a cellular or viral function, a subset of candidate target RNAs, e.g., cellular or viral RNAs, previously identified as being involved in that function can be selected and analyzed for changes in gene expression. In cases where the candidate target RNA is suspected to be a viral RNA, gene expression in the presence of svRNA expression can be measured and compared, for example, in a cell or organism deficient or lacking in PKR activity.

In the screening assays of the invention, the systems as described above can further comprise suitable controls. Such suitable controls will be obvious to one skilled in the art and are common knowledge. Particularly useful controls in the screening assays of the invention are modified RNA oligonucleotides which are complementary to the svRNA-derived miRNA or siRNA sequence, e.g., 2'-O-methyl RNA oligonucleotides. Such modified RNA oligonucleotides, e.g., 2'-O-methyl RNAs, complementary to the svRNA-derived miRNA or siRNA sequence are included in the cell- or organism-based screening assays to inactivate the siRNA or miRNA. A 2'-O-methyl RNA oligonucleotide complementary to an svRNA-derived siRNA or miRNA is capable of base-pairing with the guide-strand of the siRNA or miRNA and acting as an irreversible, stoichiometric inhibitor of the siRNA or miRNA, thereby blocking the siRNA- or miRNA-directed RNAi activity. Accordingly, 2'-O-methyl RNAs are useful in the cell- and organism-based screening assays of the invention for inactivating the siRNA or miRNA in order to verify the function or effect of the svRNA-derived siRNA or miRNA. Such 2'-O-methyl RNAs are also useful in the cell- and organism-based screening assays of the invention for inactivating the siRNA or miRNA in order to verify the function or effect of agents acting on an svRNA:target RNA pair, or to verify that a cellular or viral gene is a druggable target.

2. svRNAs as Inhibitors of RNAi

Viral structured non-coding RNAs (e.g., svRNAs) can function as inhibitors of the RNAi pathway, thereby modulating viral and/or host cell gene expression normally regulated by an RNAi-mediated function. For example, svRNAs may be incorporated into RISC or a Dicer-containing complex and thereby compete with alternate substrates for the RNAi pathway. Such a competition mechanism could be an important virulence factor for the viruses, and disabling this viral capacity would be an important factor in the creation of a vaccine.

Accordingly, in one aspect, the instant invention features a method for modulating RNAi, e.g., inhibiting RNAi, in a cell, comprising introducing into the cell a svRNA or modulatory, e.g., inhibitory, derivative thereof, such that RNAi in the cell is inhibited. In a related embodiment, the invention provides a method of inhibiting the incorporation of a siRNA or miRNA into a cellular Dicer or RISC complex, comprising introducing into the cell an isolated svRNA or inhibitory derivative thereof, such that incorporation of the siRNA or miRNA into the complex is inhibited.

In another aspect, the invention provides a method for identifying an antiviral agent, comprising: (a) contacting a cell with a test agent, said cell comprising an RNAi pathway and a svRNA, wherein the ribonucleotide inhibits the RNAi pathway; and (b) detecting an indicator of the RNAi pathway, wherein an agent is identified based on its ability to alleviate inhibition of the RNAi pathway.

In still another aspect, the invention features a method for identifying an antiviral agent, comprising: (a) contacting an assay composition with a test agent, wherein said assay composition comprises a RNAi pathway molecule and a svRNA which inhibits the activity of said RNAi pathway molecule; and (b) detecting activity of said RNAi pathway molecule, wherein said agent is identified based on its ability to restore activity of said RNAi pathway molecule. In a related embodiment, the invention further features a method for identifying an antiviral agent, comprising: (a) contacting an assay composition with a test agent, wherein said assay composition comprises a svRNA and a RNAi pathway molecule capable of interacting with or altering the svRNA; and (b) detecting the ability of the RNAi pathway molecule to interact with or alter the svRNA, wherein said agent is identified based on its ability to modulate the interaction of the svRNA with RNAi pathway molecule or alteration of the svRNA by the RNAi pathway molecule. In these screening assays of the invention, the systems as described above can further comprise suitable controls. Such suitable controls are common knowledge and will be obvious to one skilled in the art.

B. Knockout and/or Knockdown Cells or Organisms

A svRNA (or derivative thereof) (either known or identified by the methodologies of the present invention) can be used in a functional analysis of the corresponding target RNA (either known or identified by the methodologies of the present invention). Such a functional analysis is typically carried out in eukaryotic cells, or eukaryotic non-human organisms, preferably mammalian cells or organisms and most preferably human cells, e.g. cell lines such as HeLa or 293 or rodents, e.g. rats and mice. By administering a suitable RNA agent, a specific knockout or knockdown phenotype can be obtained in a target cell, e.g. in cell culture or in a target organism.

Thus, further subject matter of the invention includes cells (e.g., eukaryotic cells) or organisms (e.g. eukaryotic non-human organisms) exhibiting a target gene-specific knockout or knockdown phenotype resulting from a fully or at least partially deficient expression of at least one target gene (e.g., an endogenous target gene, a viral target gene and the like) wherein said cell or organism is transfected with or administered, respectivey, at least one svRNA (or derivative thereof, e.g., inhibitory derivative) or vector comprising DNA encoding said svRNA capable of inhibiting the expression of the target gene. It should be noted that the present invention allows a target-specific knockout or knockdown of several different endogeneous genes based on the specificity of the svRNA (or derivative thereof, e.g., inhibitory derivative) transfected or administered.

Gene-specific knockout or knockdown phenotypes of cells or non-human organisms, particularly of human cells or non-human mammals may be used in analytic procedures, e.g. in the functional and/or phenotypical analysis of complex physiological processes such as analysis of gene expression profiles and/or proteomes. Preferably the analysis is carried out by high throughput methods using oligonucleotide based chips.

The knockout or knockdown cells or organisms as described above can be further administered suitable controls to verify the activity of the svRNA (or derivative thereof, e.g., inhibitory derivative). In particular, knockout or knockdown cells or organism of the invention can be administered modified RNA oligonucleotides which are complementary to the svRNA-derived miRNA or siRNA sequence, e.g., 2'-O-methyl RNA oligonucleotides. A 2'-O-methyl RNA oligonucleotide complementary to an svRNA-derived siRNA or miRNA is capable of base-pairing with the guide-strand of the siRNA or miRNA and acting as an irreversible, stoichiometric inhibitor of the siRNA or miRNA, thereby blocking the siRNA- or miRNA-directed RNAi activity (36). Accordingly, 2'-O-methyl RNAs are useful in the knockout and/or knockdown cells or organisms of the invention for inactivating the siRNA or miRNA in order to verify the function or effect of the svRNA-derived siRNA or miRNA.

C. Functional Genomics and/or Proteomics

Another utility of the present invention could be a method of identifying gene function in an organism comprising the use of a svRNA (or derivative thereof, e.g., inhibitory derivative) to inhibit the activity of a target gene of previously unknown function. Instead of the time consuming and laborious isolation of mutants by traditional genetic screening, functional genomics would envision determining the function of uncharacterized genes by employing the invention to reduce the amount and/or alter the timing of target gene activity.

The ease with which RNA agents can be introduced into an intact cell/organism containing the target gene allows the present invention to be used in high throughput screening (HTS). Solutions containing a svRNA (or derivative thereof, e.g., inhibitory derivative) that are capable of inhibiting the different expressed genes can be placed into individual wells positioned on a microtiter plate as an ordered array, and intact cells/organisms in each well can be assayed for any changes or modifications in behavior or development due to inhibition of target gene activity. The amplified RNA can be fed directly to, injected into, the cell/organism containing the target gene. Alternatively, the svRNA (or derivative thereof, e.g., inhibitory derivative) can be produced from a vector, as described herein. Vectors can be injected into, the cell/organism containing the target gene. The function of the target gene can be assayed from the effects it has on the cell/organism when gene activity is inhibited. This screening could be amenable to small subjects that can be processed in large number, for example: *arabidopsis*, bacteria, *drosophila*, fungi, nematodes, viruses, zebrafish, and tissue culture cells derived from mammals. A nematode or other organism that produces a colorimetric, fluorogenic, or luminescent signal in response to a regulated promoter (e.g., transfected with a reporter gene construct) can be assayed in an HTS format.

It will be understood that modified RNA oligonucleotides which are complementary to the svRNA-derived miRNA or siRNA sequence, e.g., 2'-O-methyl RNA oligonucleotides, are useful in the functional genomics and/or proteomics applications of the invention in order to inactivate the siRNA or miRNA and thereby verify the function or effect of the svRNA-derived siRNA or miRNA.

D. Delivery Vehicles for RNAi Agents

One challenge that must be met to realize therapeutic applications of RNAi technologies is the development of systems to deliver RNA agents efficiently into mammalian cells. Towards that end, cassettes or vectors can be designed for expressing RNAi agents. A preferred cassette or vector of the invention includes svRNA gene sequences and/or sequences located adjacent to said svRNA gene sequences, for example in the viral genome, that facilitate expression of said svRNA gene. A preferred cassette or vector of the invention encodes a RNA having a short hairpin or stem-loop structure that is processed by Dicer (or an orthologue or homologue thereof) derived from a virus (e.g., from an adenovirus). The hairpin or stem-loop structures are processed to generate siRNA- or mi-RNA-like molecules in cells or organisms and thereby induce gene silencing. In one embodiment, the sequences encoding the stem of the stem-loop structure are substituted with a designed sequence to produce a modified svRNA (e.g., modified to increase complementarity to a target RNA), which is then processed by cells to generate siRNA- or miRNA-like molecules which, in turn, induce gene silencing.

In one embodiment, expression of the short hairpin or stem-loop structure is driven by a RNA polymerase III (pol III) promoter (T. R. Brummelkamp et al. *Science* (2002) 296: 550-553; P. J. Paddison et al., *Genes Dev*. (2002) 16: 948-958). Pol III promoters are advantageous because their transcripts are not necessarily post-transcriptionally modified, and because they are highly active when introduced in mammalian cells. In another embodiment, expression of the short hairpin or stem-loop structure is driven by a RNA polymerase II (pol II) promoter. Polymerase II (pol II) promoters may offer advantages to pol III promoters, including being more easily incorporated into viral expression vectors, such as retroviral and adeno-associated viral vectors, and the existence of inducible and tissue specific pol II dependent promoters. In a preferred embodiment, expression of the short hairpin or stem-loop structure is driven by an endogenous cryptic promoter within the svRNA sequence. The presence of a cryptic promoter within a svRNA sequence allows for expression of the svRNA without the presence of additional exogenous promoter sequences.

Vectors of the instant invention may be plasmid-based. A preferred vector of the invention is viral-based. A limitation of plasmid-based delivery systems is their dependence on cell transfection methods, which are often inefficient and limited primarily to established cell lines. Viral based strategies offer the advantage of facilitating efficient delivery to cell lines and primary cells. Recently, a retrovirus was designed to generate siRNAs driven from a pol-III dependent H1 promoter (Barton & Medzhitov (2002) *PNAS* 99: 14943-45). Using this strategy, however, the integration of a high-copy number of the H1 cassette into the host cell genome was required for efficient RNAi to be induced. A more efficient delivery system is clearly needed in the art. Viral-derived vectors, e.g., adenovirus-derived vectors, containing modified svRNA loci, e.g., VA RNA loci, according to the invention may provide novel, efficient delivery systems for RNAi agents. In a preferred embodiment, expression of the short hairpin or stem-loop structure is driven by an endogenous cryptic promoter within the svRNA sequence, thereby providing highly efficient delivery of RNAi agents.

Accordingly, in one embodiment of the instant invention, svRNA loci in a virus, e.g., virus of the adenoviridae family, are used to express miRNA- and siRNA-like molecules in cells and organisms. A svRNA locus, e.g. VA $RNA_I$ or VA $RNA_{II}$, can be constructed to generate a short dsRNA sequence, e.g. ~21-22 nt, having an intervening stem loop, that, when processed by Dicer, bears complementarity to a target RNA sequence. Virus-based vectors, e.g., adenovirus-based vectors, modified in this way are potentially highly efficient transduction systems for miRNA- and siRNA-like molecules. In one embodiment, an adenovirus can be engineered such that both VA RNA loci are modified to express sequences producing siRNA- or miRNA-like molecules. In one embodiment, an adenovirus is engineered such that at least one VA RNA loci is modified to express multiple (e.g., 2, 3, 4 or more) siRNA- or miRNA-like molecules. In another embodiment, an adenovirus is engineered such that both VA RNA loci are modified to express multiple (e.g., 2, 3, 4 or more) siRNA- or miRNA-like molecules. In another embodiment, adenovirus vectors so modified could express multiple (e.g., 2, 3, 4 or more) siRNA- or miRNA-like molecules without compromising the ability to express exogenous genes in other regions of the vector genome. Exogenous genes expressed from other regions of the vector genome can be genes whose expression is desirable for therapeutic purposes, e.g., for gene therapy. In one embodiment of the invention, the viral-based vector expresses an siRNA- or miRNA-like molecule targeting a gene associated with a disease or condition, e.g., a mutant form of a gene, e.g., a dominant negative form or dominant active form of a gene associated with a disease or condition. In another embodiment of the invention, the viral-based vector expresses an siRNA- or miRNA-like molecule targeting a gene associated with a disease or condition, e.g., a mutant form of a gene, e.g., a dominant negative form or dominant active form of a gene associated with a disease or condition, and an exogenous gene is expressed from another region of the vector genome, e.g., a wild type copy of the gene. Also within the scope of the present invention are cassettes providing siRNA- or miRNA-like molecules derived from VA RNA or VA RNA-like sequences/structures for the production of molecules with RNAi inducing activity, wherein the cassettes are present within other vectors or expression systems, e.g., non-adenoviridae virus families or plasmids.

V. Methods of Treatment

The present invention provides methods for identifying svRNAs and their targets (as well as modulators of said targets), which can further be used clinically (e.g., in certain prophylactic and/or therapeutic applications). For example, svRNAs can be used as prophylactic and/or therapeutic agents in the treatment of diseases or disorders associated with unwanted or aberrant expression of the corresponding target gene.

In one embodiment, the invention provides for prophylactic methods of treating a subject at risk of (or susceptible to) a disease or disorder, for example, a disease or disorder associated with aberrant or unwanted target gene expression or activity. Subjects at risk for a disease which is caused or contributed to by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression.

In another embodiment, the invention provides for therapeutic methods of treating a subject having a disease or disorder, for example, a disease or disorder associated with aberrant or unwanted target gene expression or activity. In an exemplary embodiment, the modulatory method of the invention involves contacting a cell capable of expressing target ncRNA or target gene with a therapeutic agent that is specific for the target ncRNA, target gene or protein (e.g., is specific for the mRNA encoded by said gene or specifying the amino acid sequence of said protein) such that expression or one or more of the activities of target protein is modulated. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

"Treatment", or "treating" as used herein, is defined as the application or administration of a prophylactic or therapeutic agent to a patient, or application or administration of a prophylactic or therapeutic agent to an isolated tissue or cell line from a patient, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one embodiment, a target gene of the invention is an antiviral target. In another embodiment, a target gene of the invention is a gene involved in maintaining cellular homeostasis. Examples of genes involved in maintenance of homeostasis include, for example, genes associated with regulation of cell growth, including growth factors or receptors for growth factors, transcription factors, apoptotic or anti-apoptotic factors, genes associated with regulation of metabolic function, genes associated with regulation of cell specific functions and/or differentiation and/or development, and tumor suppressor genes. Modulation of such genes is particularly useful, for example, to treat any of a number of disorders (including cancer, inflammation, diabetes, neuronal disorders, etc.). In one embodiment, a target gene of the invention is a mutant form of a gene, e.g., a dominant negative or dominant active form of the gene, preferably associated with a disease or disorder.

Further, since miRNAs are believed to be involved in translational control, knowledge of miRNA-like molecules and their targets would allow specific modulation of a variety of systems controlled at the translational level. Manipulating translation of genes (e.g., the genes described above) is a novel, powerful, and specific method for treating these disorders.

In one embodiment, the invention features a method of creating an attenuated virus, involving modifying a svRNA sequence of a virus so that, for example, the ability of the svRNA to act as a substrate or inhibitor of the RNAi pathway is diminished, thereby providing an attenuated virus. In another embodiment, the invention provides a method of creating an attenuated virus, involving inserting a svRNA or svRNA-like sequence into a viral genome, wherein the svRNA or svRNA-like sequence produces an siRNA or miRNA that modulates expression of at least one viral gene, thereby creating an attenuated strain of virus. An attenuated virus produced according to the claimed invention is less virulent due to any number of deficiencies, e.g., the attenuated virus may have reduced replicative capacity, reduced capacity for transcription or translation of viral genes, reduced ability to utilize the host cell's machinery, reduced ability to antagonize host cell's antiviral response, and the like.

The invention also contemplates use of svRNAs (and derivatives thereof) as well as modulators, for example, of svRNA targets, in various agricultural treatments. In one embodiment, a compound or agent of the invention is used to modulate RNAi in an insect. In another embodiment, a compound or agent of the invention is used to modulate RNAi in a bacteria. In another embodiment, a compound or agent is used to modulate RNAi in a parasite. In certain embodiments, a compound or agent is administered to the organism (e.g., fed to the organism). In certain embodiments, the organism ingests the compound or agent. An exemplary compound or agent makes the organism sterile upon ingestion. In another embodiment, the organism becomes infected with, for example, a microbe or virus that delivers the compound or agent (e.g., an agricultural microbe or virus). In another embodiment, a compound or agent of the invention is used to modulate RNAi in a plant.

VI. Pharmacogenomics and Pharmaceutical Compositions

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

With regards to the above-described agents for prophylactic and/or therapeutic treatments (e.g., svRNAs or derivatives thereof), the agents are routinely incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

When administering svRNAs (or derivatives thereof), it may be advantageous to chemically modify the RNA in order to increase in vivo stability. Preferred modifications stabilize the RNA against degradation by cellular nucleases.

The pharmaceutical compositions can be included in a container, pack, or dispenser together with instructions for administration.

This invention is further illustrated by the following examples which should not be construed as limiting. The contents of all references, patents and published patent applications cited throughout this application are incorporated herein by reference.

EXAMPLES

Example I

Figure 2:
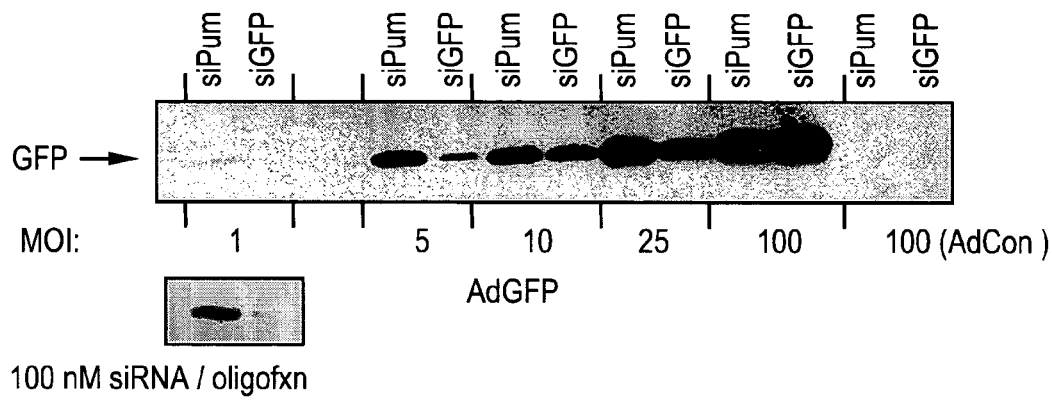
FIG. 2 is an analysis of siRNA-induced gene silencing of a virally encoded reporter gene where the virus is nonreplicating.

Analysis of siRNA-Induced Gene Silencing of a Virally Encoded Reporter Gene where the Virus is Nonreplicating HeLa cells were transfected using Oligofectamine with 100 nM siRNA. The siRNA was either siGFP, specific for the Green Fluorescent Protein (GFP) mRNA sequence, or siPum, an siRNA specific for the *Pumilio* transcript expressed in *Drosophila* (a transcript for which there is no known mammalian counterpart or equivalent) as a non-specific control. After 24 hr, the cells were infected over a range of MOIs with recombinant adenovirus expressing either GFP (AdGFP) or an empty cassette (AdCon) as a control. At 24 hr post-infection (48 hr after siRNA transfection), total cellular protein was harvested using standard RIPA buffer. Protein samples were analyzed by Western blot using a polyclonal antibody directed to GFP (Clontech). The results, as presented in FIG. 2, demonstrate that an siRNA can induce RNAi to inhibit expression of a gene expressed from a recombinant adenovirus in mammalian cells.

Example II

Figure 3:
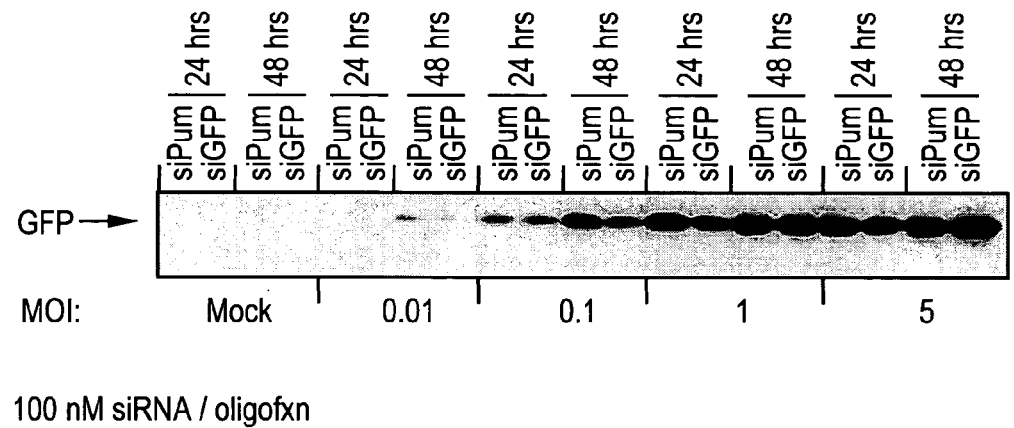
FIG. 3 is an analysis of siRNA-induced gene silencing of a virally encoded reporter gene where the virus is replicating.

Analysis of siRNA-Induced Gene Silencing of a Virally Encoded Reporter Gene where the Virus is Replicating 293 cells were transfected using Oligofectamine with 100 nM siRNA. The siRNA was either siGFP, specific for the Green Fluorescent Protein (GFP) mRNA sequence, or siPum as a non-specific control. After 24 hr, the cells were infected over a range of MOIs with recombinant adenovirus expressing either GFP (AdGFP) or an empty cassette (AdCon) as a control. The 293 cells contained an endogenous copy of the Adenovirus E1 gene, and therefore complemented the recombinant virus to produce a "replicating" viral environment. At 24 and 48 hr post-infection (48 and 72 hr after siRNA transfection), total cellular protein was harvested using standard RIPA buffer. Protein samples were analyzed by Western blot using a polyclonal antibody directed to GFP (Clontech). The results, as presented in FIG. 3, demonstrate that an siRNA can induce RNAi to inhibit expression of a gene expressed from a replicating recombinant adenovirus in mammalian cells, but only at low MOIs. These results raise the possibility that adenovirus encodes an anti-RNAi factor.

Example III

Figure 4:
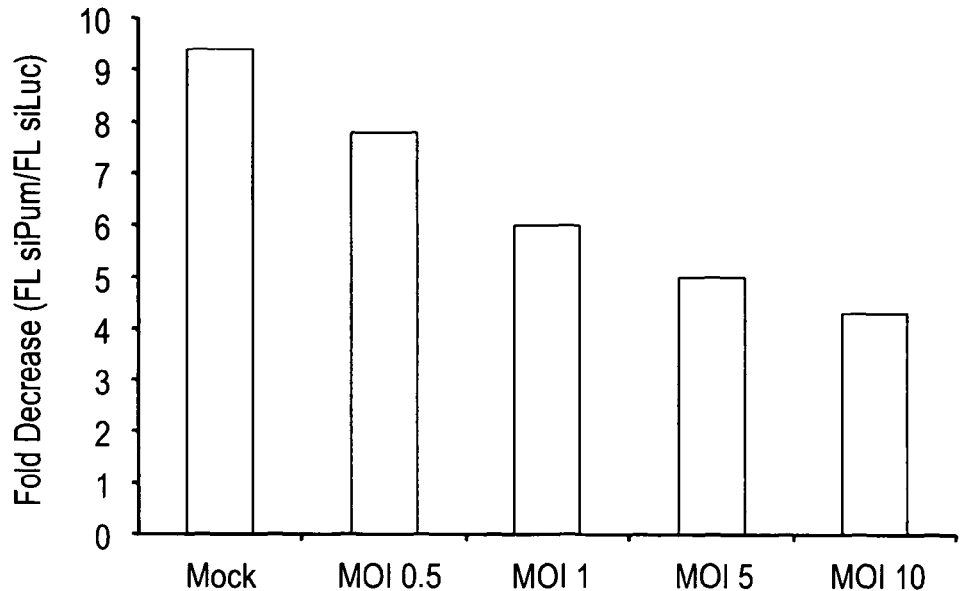
FIG. 4 is an analysis of the effects of non-replicating Adenovirus-5 on siRNA gene silencing activity in HeLa cells.

Analysis of the Effects of Replicating Adenovirus-5 on siRNA Gene Silencing Activity in HeLa Cells HeLa cells grown in a 6-well plate were infected with varying amounts of wild type Adenovirus (Ad-5), or were mock infected as a control. At 8-12 hr post-infection, cells were cotransfected using Lipofectamine Plus with plasmids expressing firefly luciferase (FL) and *renilla reniformis* luciferase (RL) together with 20 nM siRNA. The siRNA was either an siRNA specific for FL mRNA, or a non-specific siRNA (siPum) as a control. After 12 hr (24 hr following Ad-5 infection), cellular extracts were collected using 200 µL 1× Passive Lysis Buffer (Promega) and 20 µL extract was used to perform a luciferase assay using a luminometer. Luciferase activity from RL was used to normalize that of FL for experimental samples. The fold-decrease was then measured as the reduction in FL activity comparing siPum to siLuc samples (i.e., FL siPum/FL siLuc) for each data set. The results, as presented in FIG. 4, demonstrate that the presence of wt Ad-5 within a cell can effectively inhibit siRNA activity, thereby preventing siRNA-induced gene silencing.

Example IV

Figure 5:
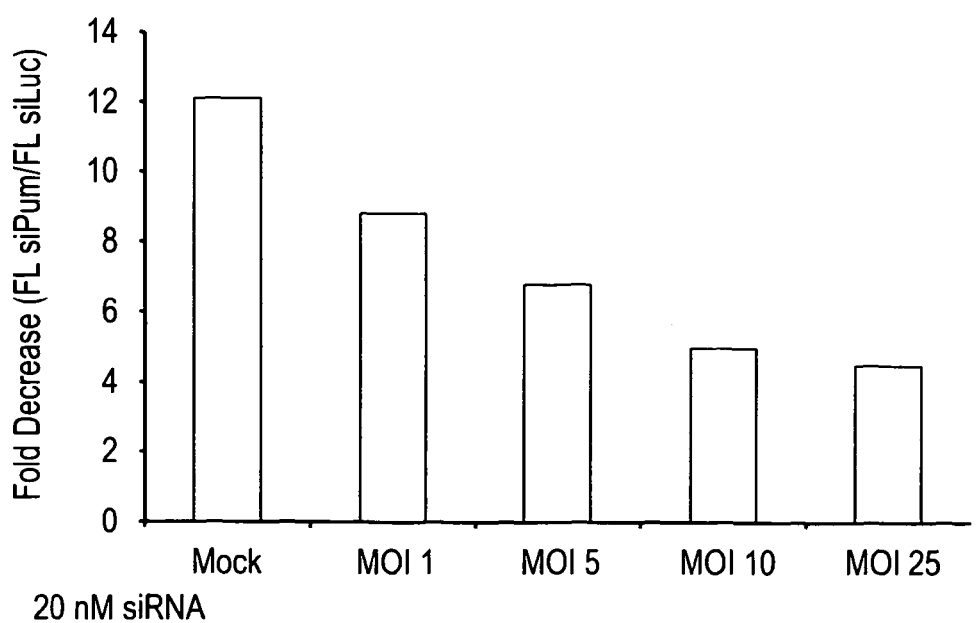
FIG. 5 is an analysis of the effects of replicating Adenovirus-5 on siRNA gene silencing activity in 293 cells.

Analysis of the Effects of Replicating Adenovirus-5 on siRNA Gene Silencing Activity in 293 Cells 293 cells grown in a 6-well plate were infected with varying amounts of wild type Adenovirus (Ad-5), or were mock infected as a control. At 8-12 hr post-infection, cells were cotransfected using Lipofectamine Plus with plasmids expressing firefly luciferase (FL) and *renilla reniformis* luciferase (RL) together with 20 nM siRNA. The siRNA was either an siRNA specific for FL mRNA, or a non-specific siRNA (siPum) as a control. After 12 hr (24 hr following Ad-5 infection), cellular extracts were collected using 200 µL 1× Passive Lysis Buffer (Promega) and 20 µL extract was used to perform a luciferase assay using a luminometer. Luciferase activity from RL was used to normalize that of FL for experimental samples. The fold-decrease was then measured as the reduction in FL activity comparing siPum to siLuc samples (i.e., FL siPum/FL siLuc) for each data set. The results, as presented in FIG. 5, demonstrate that the presence of replicating wt Ad-5 within a cell can effectively inhibit siRNA activity, thereby preventing siRNA-induced gene silencing.

Example V

Analysis of VA RNA Cleavage in *Drosophila* Embryo Extract and by Recombinant Human Dicer

*Drosophila* embryo extracts competent for Dicer cleavage were incubated for various times with $^{32}$P-labeled VA RNA or pre-Let-7 precursor substrates. VA RNA$_{lysis}$ refers to labeled VA RNA substrate that was resuspended in lysis buffer (100 mM potassium acetate, 30 mM HEPES-KOH pH 7.4, 2 mM magnesium acetate), heated to 95° C. for 2 min. and then allowed to refold at 37° C. for 30 min. VA RNA$_{H2O}$ refers to labeled VA RNA substrate that was resuspended in water. Pre-Let-7 substrate was also resuspended in water. Pre-Let-7 is known to be processed to ~22 nt product in this reaction, and thus served as a positive control. Reactions were performed as described (see Tuschl et al, *Genes Dev* (1999), 13:3191-97) and contained the following: 10 µL lysate, 6 µL 40× reaction mix, 4 µL labeled substrate (50 nM final concentration), and H$_2$O. Briefly, reactions were incubated at 25° C., and 6 uL aliquots were removed at various times and placed in 2×PK Buffer. Aliquots were then deproteinated, resuspended in 11.5 µL Formamide Loading Buffer (98% formamide, 10 mM EDTA pH 8, 0.025% xylene cyanol, 0.025% bromophenol blue), and 5 uL of each sample was electrotrophoresed on a 15% denaturing PAGE gel (Tuschl et al, 1999). Results are presented in FIG. 6 (left). The accumulation of VA RNA cleavage products at ~21 nt was visible at the 1.5 and 3 hr time points, but not at the onset of the reaction (O hr time point). Cleavage products were found to be of similar size to those generated by cleavage of the pre-Let-7 substrate. These results demonstrated that an activity in the *Drosophila* embryo extract was able to recognize and cleave the VA RNA in a manner similar to the processing of the known miRNA precursor, pre-Let-7.

Figure 6:
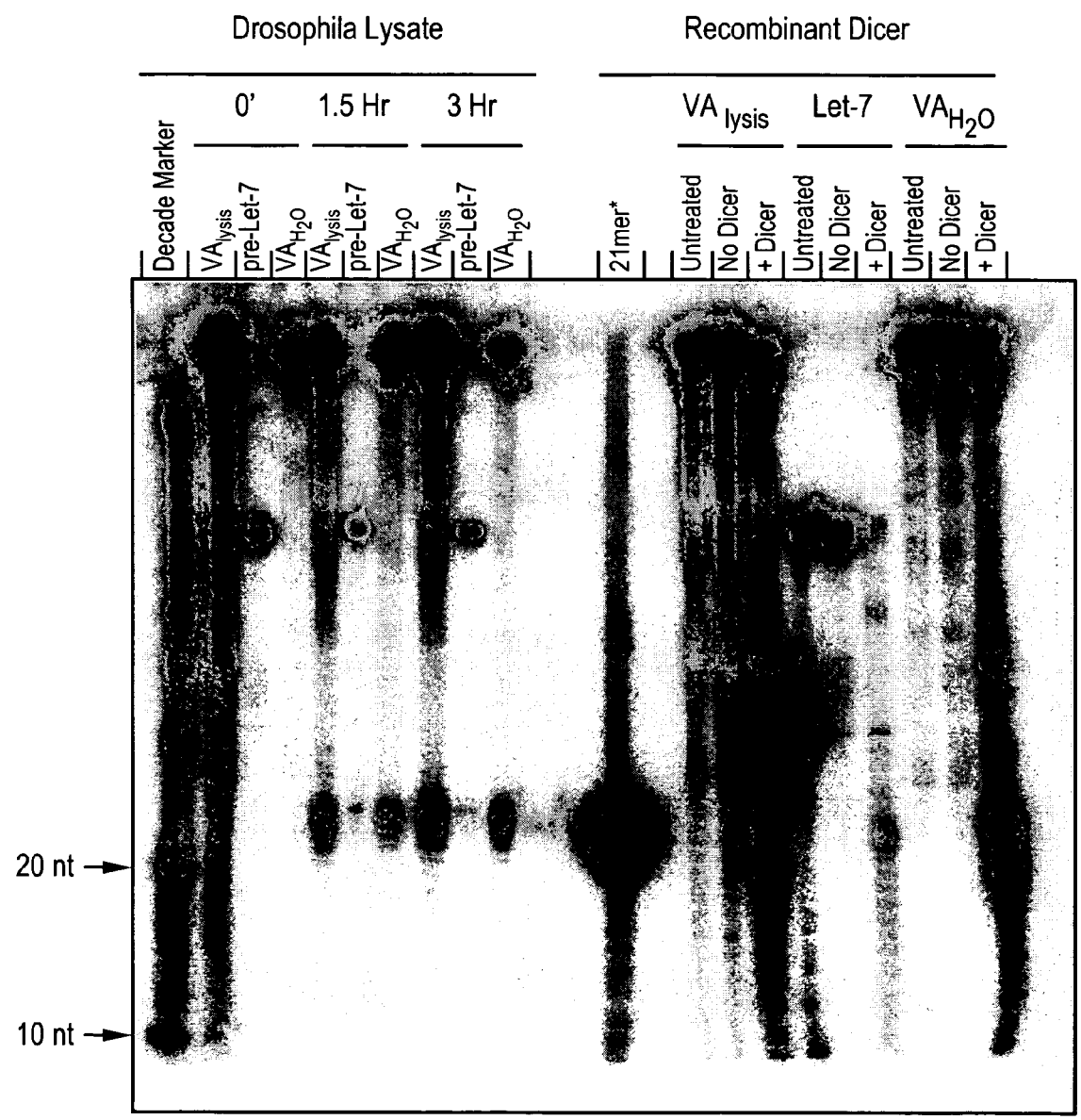
FIG. 6 is an analysis of VA RNA cleavage in *Drosophila* embryo extract and by recombinant Dicer enzyme.

Using the same templates as set forth above, reactions were also carried out with recombinant human Dicer enzyme (Gene Therapy Systems) to analyze potential recognition and cleavage of VA RNAs by the purified enzyme. Reactions were performed as described by the manufacturer, and contained 0.25 µg labeled RNA template in a total volume of 5 µL. Reactions were incubated at 37° C. overnight, and samples were then deproteinated, resuspended in 11.5 µL Formamide Loading Buffer (98% formamide, 10 mM EDTA pH 8, 0.025% xylene cyanol, 0.025% bromophenol blue), and 5 uL of each sample was electrotrophoresed on a 15% denaturing PAGE gel. Results are shown in FIG. 6 (right). "Untreated" refers to a negative control reaction in which template RNA was not subjected to the Dicer reaction, while "No Dicer" indicates that reactions contained all components except for the Dicer enzyme. The accumulation of ~21 nt VA RNA cleavage products was detected, but only in reactions containing the Dicer enzyme. These products were of similar size to those generated in the *Drosophila* lysate (FIG. 6, left), indicating that the activity in the lysate observed to cleave VA RNA was likely that of Dicer. The results thus demonstrate that human Dicer can process VA RNA to an RNA product of ~21-23 nt.

Example VI

Time Course of VA RNA Cleavage Using Recombinant Human Dicer Enzyme

Figure 7:
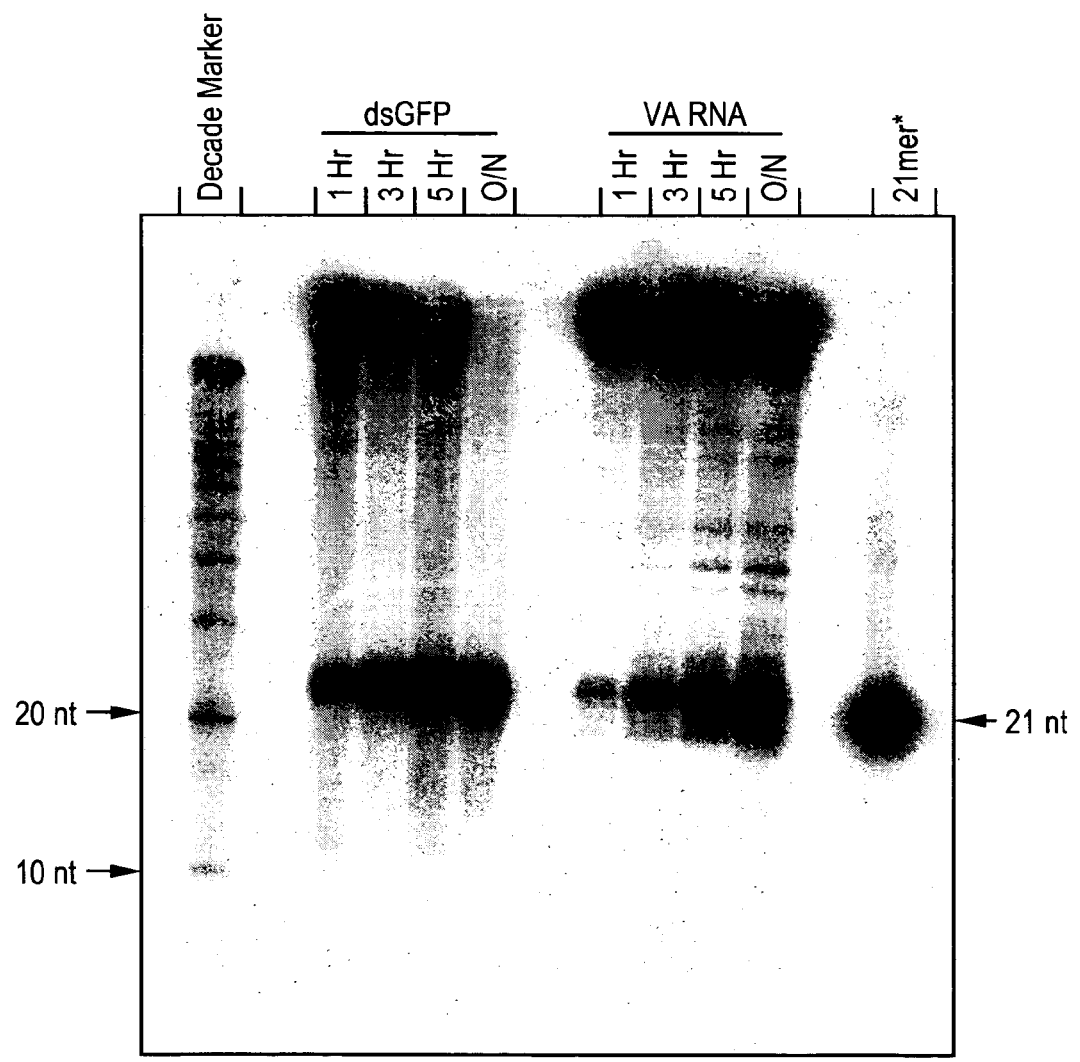
FIG. 7 is a time course of VA RNA cleavage using recombinant Dicer enzyme.

An RNA cleavage assay was carried out using recombinant human Dicer enzyme (Gene Therapy Systems) and $^{32}$P-radiolabeled VA RNA as substrate. Radiolabeled, double-stranded GFP RNA of ~500 bp was used as a positive control for cleavage. Reactions were carried out according to manufacturer's instructions, except that they were scaled up to contain 1 µg RNA substrate in a total volume of 25 µL. At indicated time points, 5.5 µL was removed from each reaction and placed in 2×PK Buffer (Tuschl et al, 1999). Samples were then deproteinated, resuspended in 16 µL Formamide Loading Buffer, and 7.5 µL of each sample was analyzed on a 15% denaturing PAGE gel. Results are presented in FIG. 7. The accumulation of VA RNA cleavage products of ~21 nt were visible, and a lack of non-specific bands of ~10 nt indicated that VA RNA was specifically processed.

Example VII

Specificity of Human Dicer Cleavage Activity for VA RNA Using Unlabeled Competitor RNA RNA cleavage competition assays were carried out using recombinant human Dicer enzyme (Gene Therapy Systems), $^{32}$P-radiolabeled VA RNA substrate and varying molar excesses of unlabeled, competitor RNA. Cleavage reactions contained components as described by the manufacturer in a total volume of 10 µL. Reactions were pre-incubated with 1.5 µL unlabeled, competitor RNA (or no competitor RNA, where indicated) for 20 min at 25° C. Then, 1 µL $^{32}$P-radiolabeled VA RNA template was added to a 100 nM final concentration, and reactions were further incubated at 25° C. for 4 hrs. Reactions were deproteinated, resuspended in 17 µL Formamide Loading Buffer as described (Tuschl et al, 1999), and 8 µL of each reaction was analyzed on a 15% denaturing PAGE gel.

Figure 8:
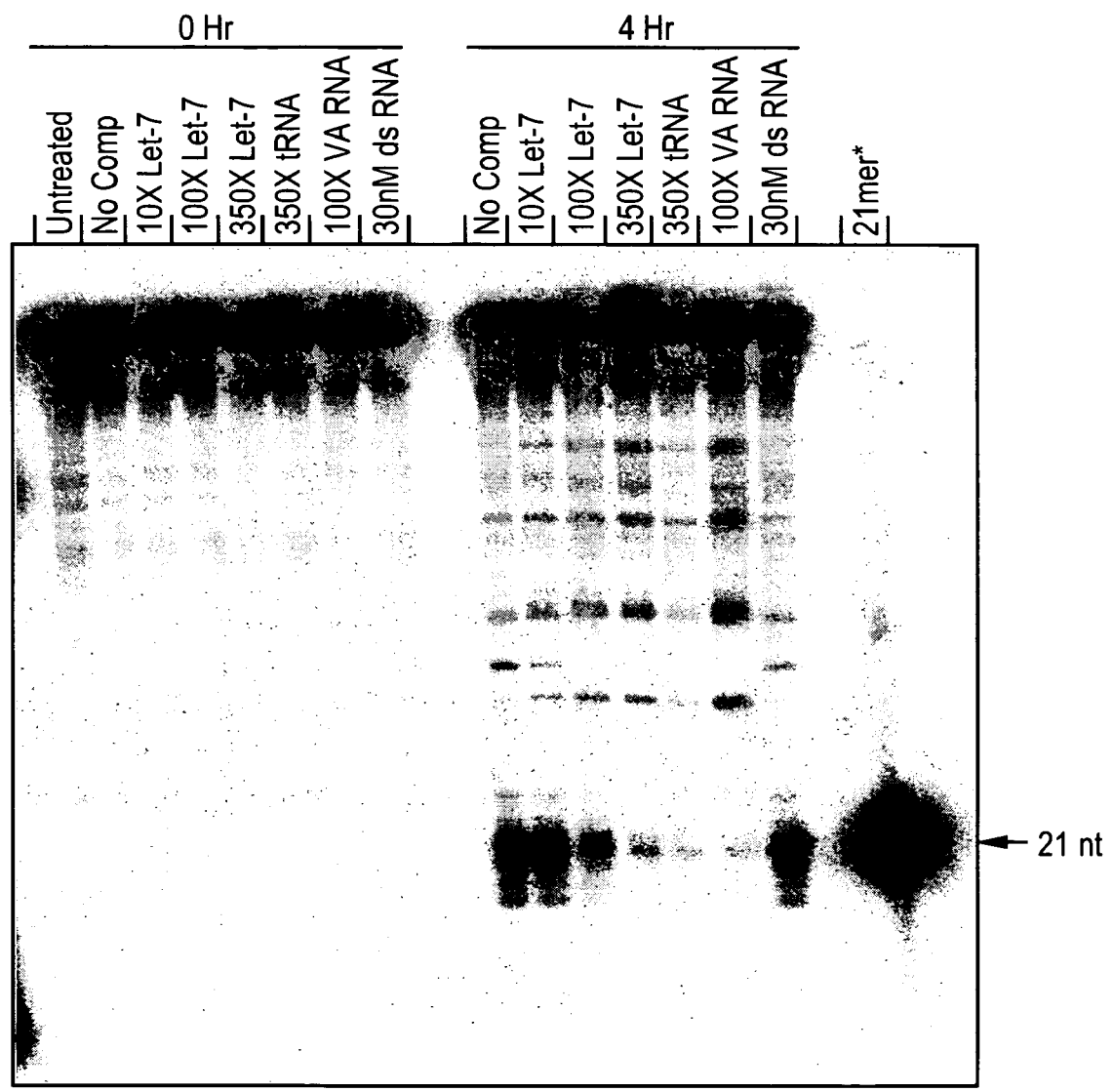
FIG. 8 is a demonstration of the competition of Dicer cleavage activity for VA RNA versus unlabeled competitor RNA.

Results are presented in FIG. 8. "Untreated" refers to RNA substrate that was not subjected to the above reaction, demonstrating that cleavage products were not present in the original RNA preparations, and "No Comp" indicates that the reaction did not contain unlabeled competitor. No product was observed at 0 hr, as expected. At the 4 hr time point, VA RNA ~21 nt cleavage product was visible in the control reaction, when no competitor was present, as well as in reactions where 10× pre-Let-7, 100× pre-Let-7, or dsRNA was included in the reaction. In contrast, product accumulation was diminished when 350× pre-Let-7, 350× tRNA, and 100× VA RNA were the competitors. These results indicated that at these higher concentrations, the unlabeled RNAs were effectively competing with the labeled VA RNA substrate for cleavage by Dicer. The 100× VA RNA appeared to be the most efficient competitor, suggesting that VA RNA may have a higher affinity for Dicer or be more efficiently processed by the enzyme than the pre-Let-7 or tRNA competitor RNAs.

Example VIII

Competition of Dicer Cleavage Activity for pre Let-7 Versus Unlabeled Competitor RNA RNA cleavage competition assays were carried out using recombinant Dicer enzyme as described in Example VII, except that $^{32}$P-radiolabeled Pre Let-7 was used as the cleavage substrate. Reactions were pre-incubated with 1.5 µL unlabeled, competitor RNA (or no competitor RNA, where indicated) for 20 min at 25° C. Then, 1 µL $^{32}$P-radiolabeled Pre-Let-7 template was added to a 100 nM final concentration, and reactions were further incubated at 25° C. for 4 hrs. Reactions were processed and analyzed as described in Example VII.

Figure 9:
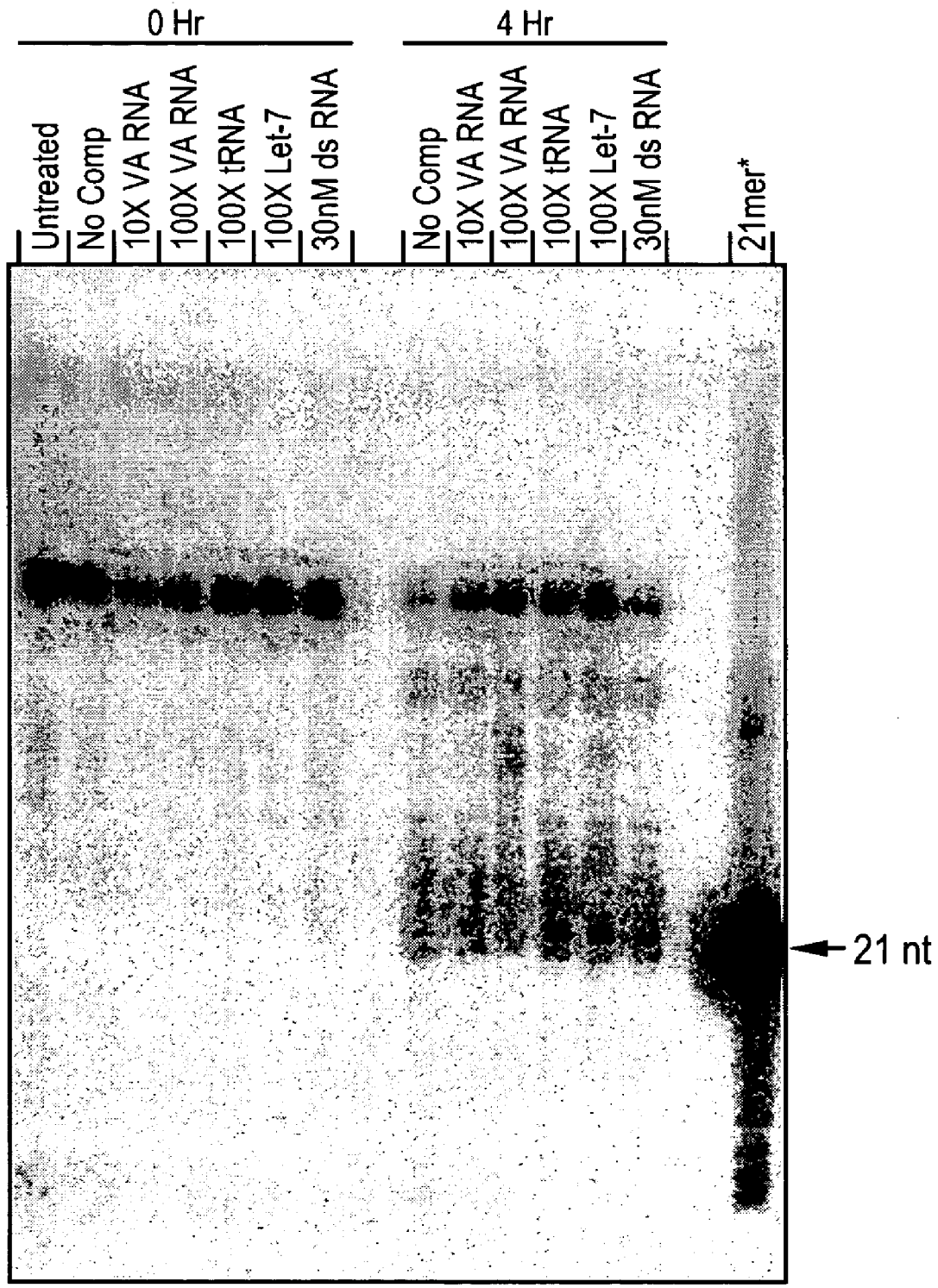
FIG. 9 is a demonstration of the competition of Dicer cleavage activity for pre Let-7 versus unlabeled competitor RNA.

Results are presented in FIG. 9. "Untreated" refers to RNA substrate that was not subjected to the above reaction, demonstrating that cleavage products were not present in the original RNA preparations, and "No Comp" indicates that the reaction did not contain unlabeled competitor. No cleavage product was observed at 0 hr, as expected. At 4 Hr, VA RNA ~~21 nt cleavage product was visible in the control reaction, when no competitor was present, as well as in the other lanes. However, the accumulation of cleavage product was diminished when the competitor was 10× or 100×VA RNA. These results indicated that at these concentrations, the unlabeled VA RNAs were effectively competing with the labeled pre-Let-7 substrate for cleavage by Dicer. As found in Example VII, the VA RNA appeared to be the most efficient competitor, further suggesting that VA RNA may have a higher affinity for Dicer or be preferentially processed by the enzyme than the pre-Let-7 or tRNA competitor RNAs.

Example IX

Figure 10:
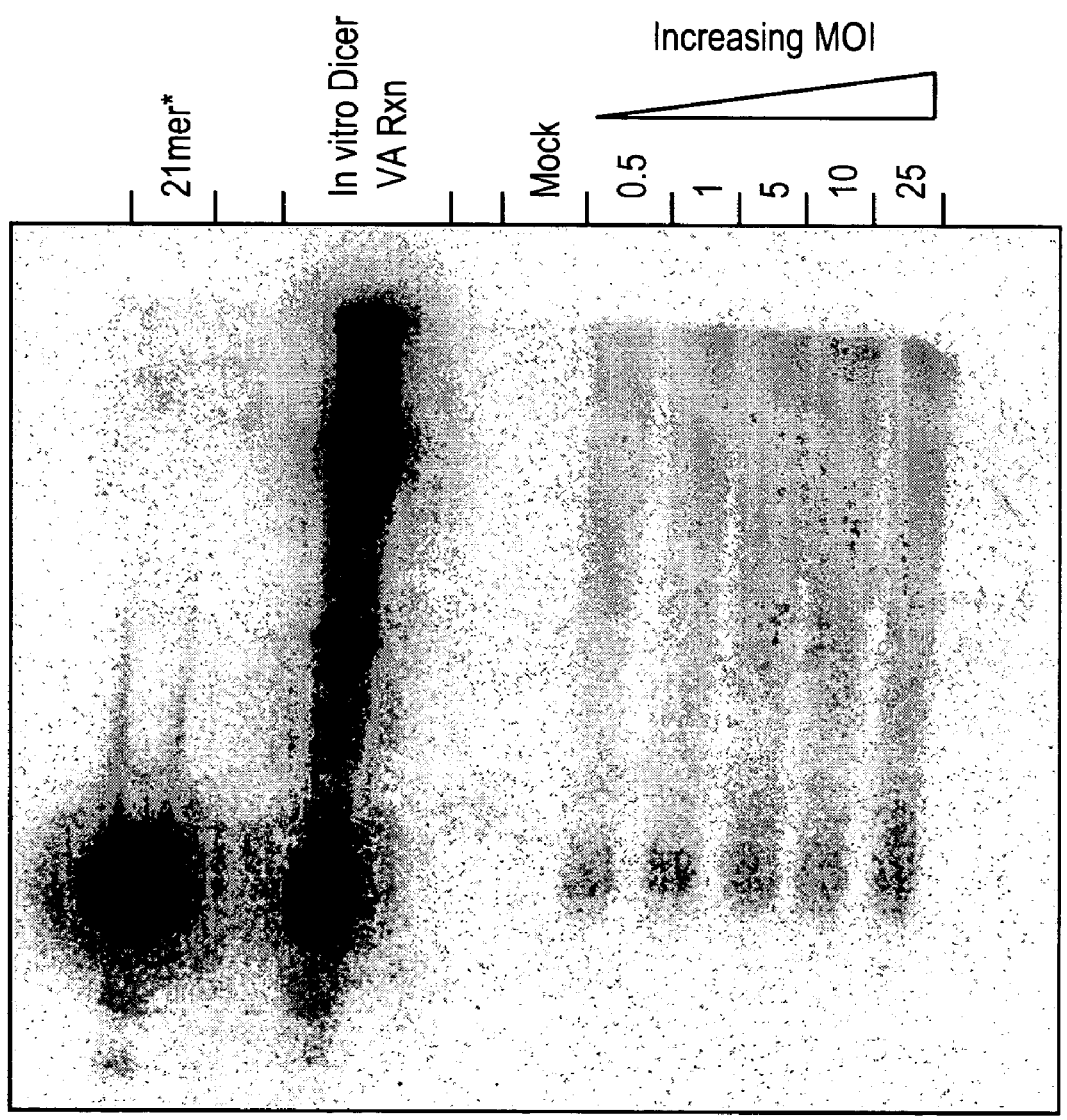
FIG. 10 is a northern analysis of VA RNA 21-25 nt cleavage products in Adenovirus-5 infected cells.

Northern Analysis of VA RNA 21-25 nt Cleavage Products in Adenovirus-5 Infected Cells To test whether VA RNAs are in fact processed into small RNAs in adenovirus infected cells, HeLa cells were infected with various MOIs of WT Ad-5 in 150 mm dishes. At 18 hr post infection, the cells were lysed and RNA was extracted using Trizol reagent (Invitrogen) according to the manufacturer's protocol. 100 µg of each sample was electrophoresed on a 15% PAGE gel under denaturing conditions, and the gel was transferred to a nylon membrane via semi-dry electroblotting at 400 mA for one hour. RNA was crosslinked to the nylon membrane by UV crosslinking (Stratagene, Stratalinker). The membrane was pre-hybridized for 1 hr at 37° C. in a formamide hybridization buffer and then hybridized overnight with full length probe for VA RNA ($^{32}$P-labeled reverse complement transcript of VA RNA). The following day, the membrane was washed and bands were detected using a Phosphorimager. The results of this experiment are presented in FIG. 10. One control lane on the gel contains a $^{32}$P-labeled 21 mer siRNA, and an additional control lane contains the contents of an in vitro recombinant Dicer reaction with unlabeled VA RNA (as described supra).

The results demonstrate that VA RNA1 is processed into small RNAs in adenovirus-infected cells.

Example X

Figure 11:
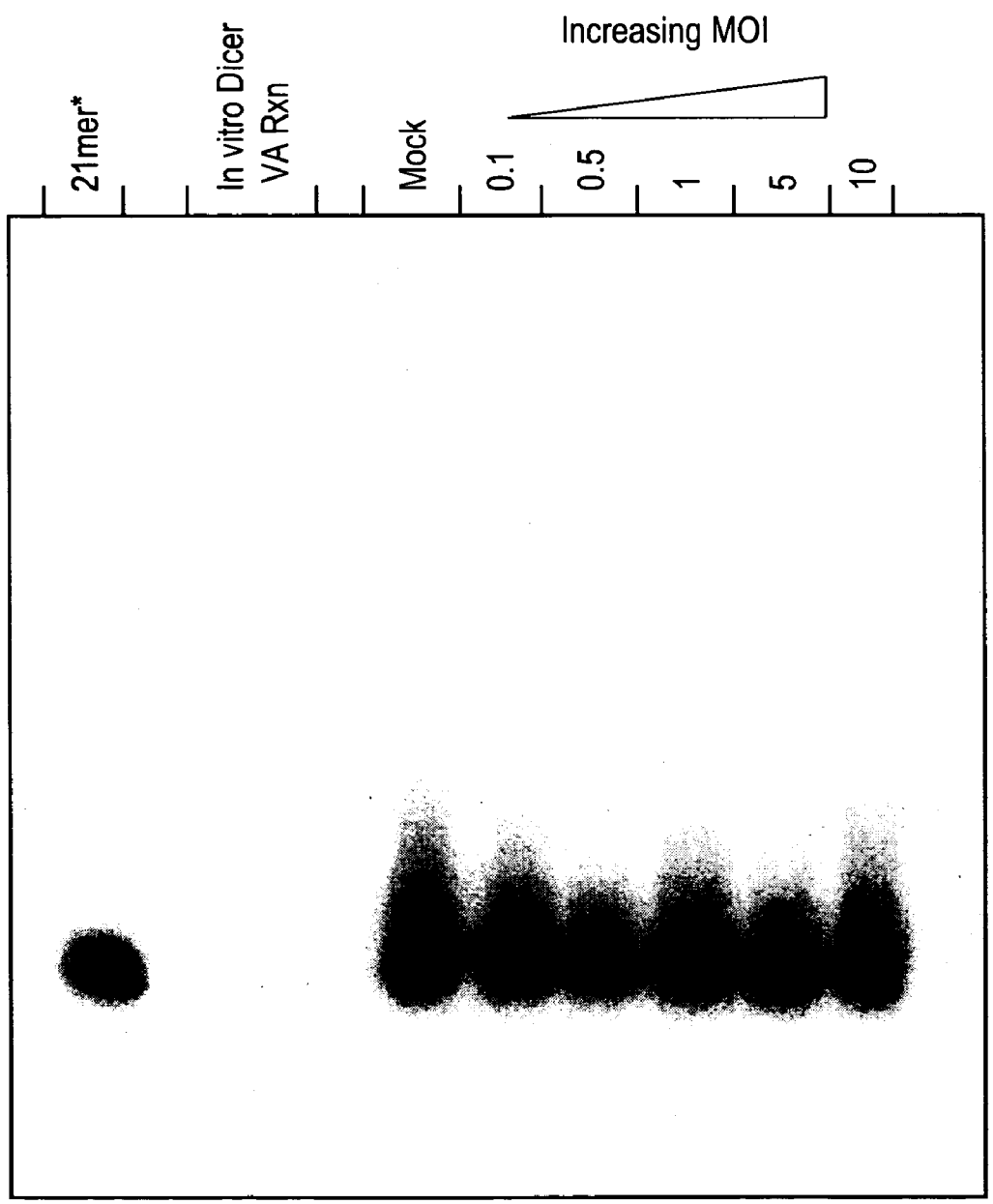
FIG. 11 is a northern analysis of Let-7 RNA cleavage products in Adenovirus-5 infected cells.

Northern Analysis of Let-7 RNA Cleavage Products in Adenovirus-5 Infected Cells Next, the effect of Adenovirus-5 infection on the levels of endogenous Let-7 miRNA was assessed. HeLa cells were infected with various MOIs of WT Ad-5 in 150 mm dishes. At 18 hr post infection, the cells were lysed and RNA was extracted using Trizol reagent (Invitrogen) according to the manufacturer's protocol. 100 µg of each sample was electrophoresed on a 15% PAGE gel under denaturing conditions, and the gel was transferred to a nylon membrane via semi-dry electroblotting at 400 mA for one hour. RNA was crosslinked to the nylon membrane by UV crosslinking (Stratagene, Stratalinker). The membrane was pre-hybridized for 1 hr at 37° C. in a formamide hybridization buffer and then hybridized overnight with 100 pmoles of a gamma-$^{32}$P ATP labeled human Let-7 RNA probe (UAUACAACCACCUACUAC-CUCAUU). The following day, the membrane was washed and bands were detected using phosphorimager. The results of this experiment are presented in FIG. 11. One control lane on the gel contains a $^{32}$P-labeled siRNA 21 mer, and an additional control lane contains the contents of an in vitro recombinant Dicer reaction with unlabeled VA RNA (as described supra). The results show that levels of an endogenous miRNA, Let-7, decrease in adenovirus-infected cells.

Example XI

Analysis of Specific Target Cleavage Product by VA-miRNA

Figure 12:
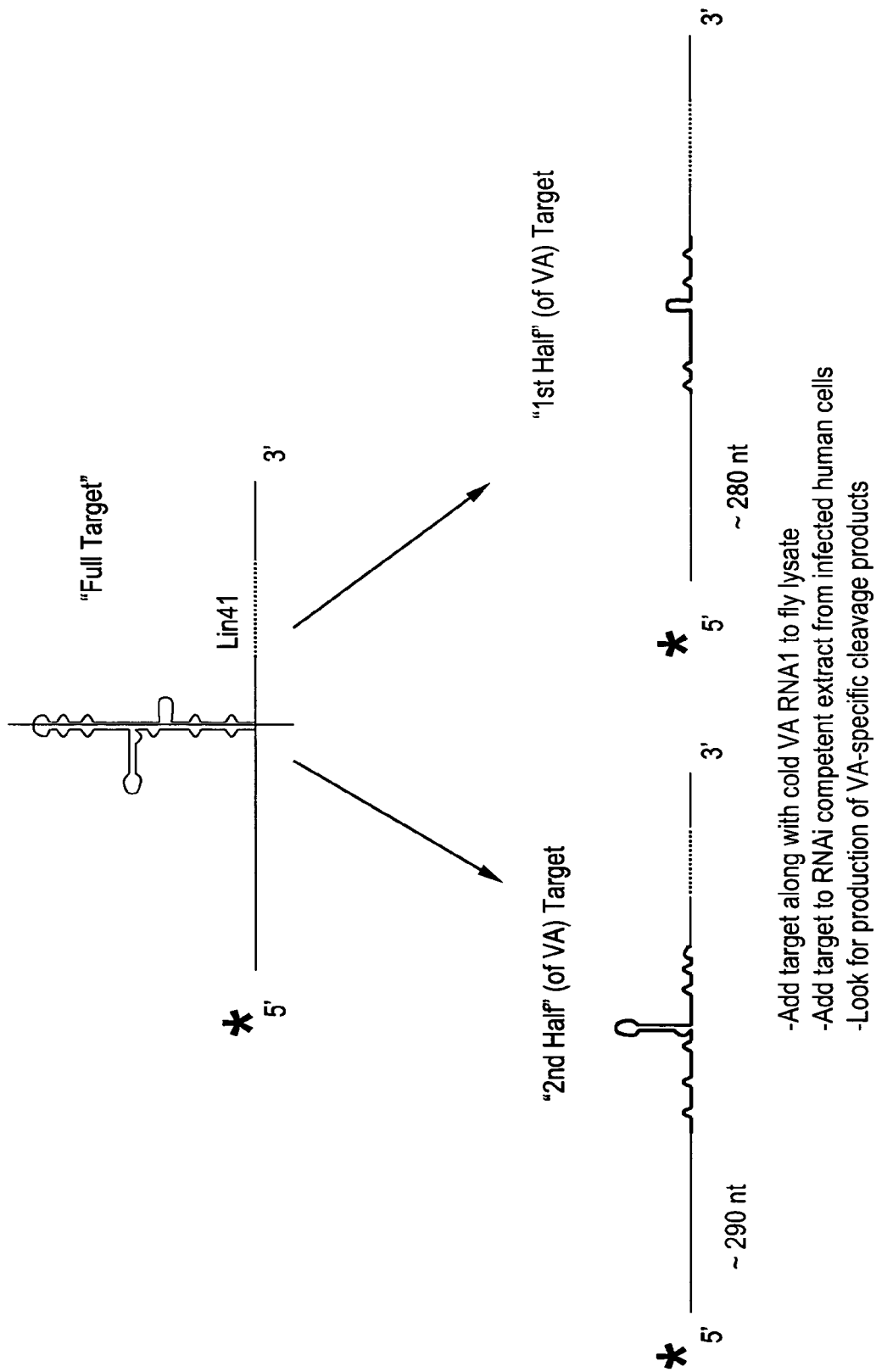
FIG. 12 is a schematic for target cleavage by VA-miRNA.

FIG. 12 provides a schematic of the design of targets used in RISC cleavage assays. mRNA targets containing the reverse complement of the VA RNA1 sequence were generated. The "Full" target contains the reverse complement of the entire VA RNA1 sequence (ANR AV), while the "1$^{st}$ Half" and "2$^{nd}$ Half" targets contain either half of the ANR AV sequence. These mRNA targets were 5' cap labeled with $^{32}$P GTP, so that cleavage products of specific sizes could be determined by electrophoretic separation. The targets can be incubated in extracts made from human cells (as described in Current Protocols in Molecular biology, Part 2, 1993) infected with Adenovirus to determine if Adenoviral RNAs loaded into the RISC during the course of infection will lead to specific cleavage on the targets. Additionally, the targets can be incubated in RNAi-competent fly lysates that have been pre-incubated with non-labeled VA RNA. This pre-incubation will allow the VA RNA to be processed by Dicer in vitro, and loaded into the RISC machinery with VA-specific small RNA sequences.

Figure 13:
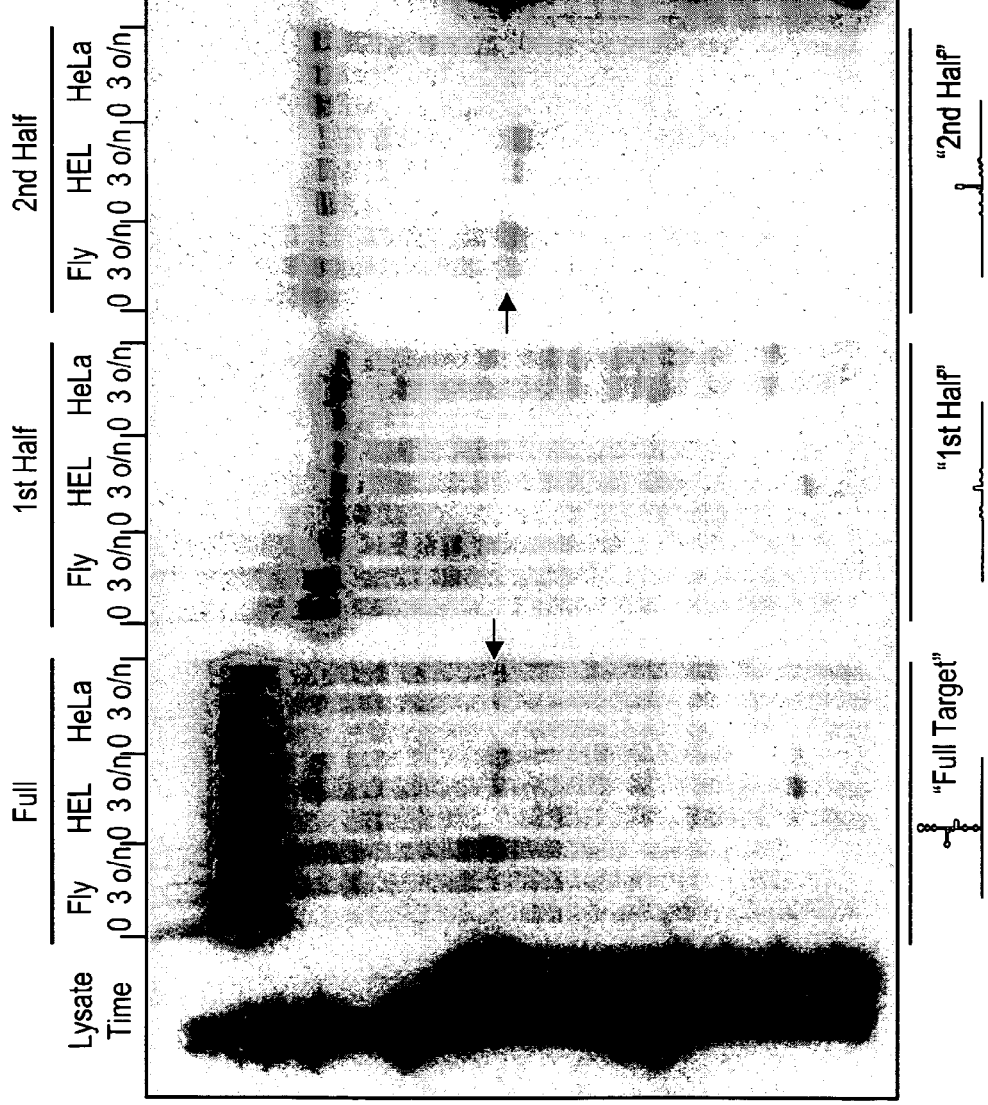
FIG. 13 is a demonstration of specific target cleavage by VA-miRNA.

FIG. 13 provides an analysis of specific target cleavage by VA-miRNA. The targets from FIG. 12 were incubated in either extracts from human cells (HEL or HeLa) infected with wild type Adenovirus type-5 or fly extracts pre-incubated with non-labeled VA RNA, as described above. The arrows point to specific cleavage products that accumulate over the course of the assay for the various targets and extracts. These targets all map to the region of the target containing the ANR AV sequence. The "1$^{st}$ Half" target only yields specific cleavage products in the fly lysate, while the "Full" and "2$^{nd}$ Half" targets yield specific cleavage products in the fly as well as infected human cell extracts. These results indicate that specific target cleavage is likely being directed by small RNAs derived from the VA RNA1 species. Additionally, the small RNAs directing this cleavage appear to follow the rules of miRNA asymmetry, as specific products are produced for only the 2$^{nd}$ Half target in the infected human cell extracts, and not the corresponding portion of the VA RNA molecule contained in the ANR AV sequence of the 1$^{st}$ Half target.

Figure 14:
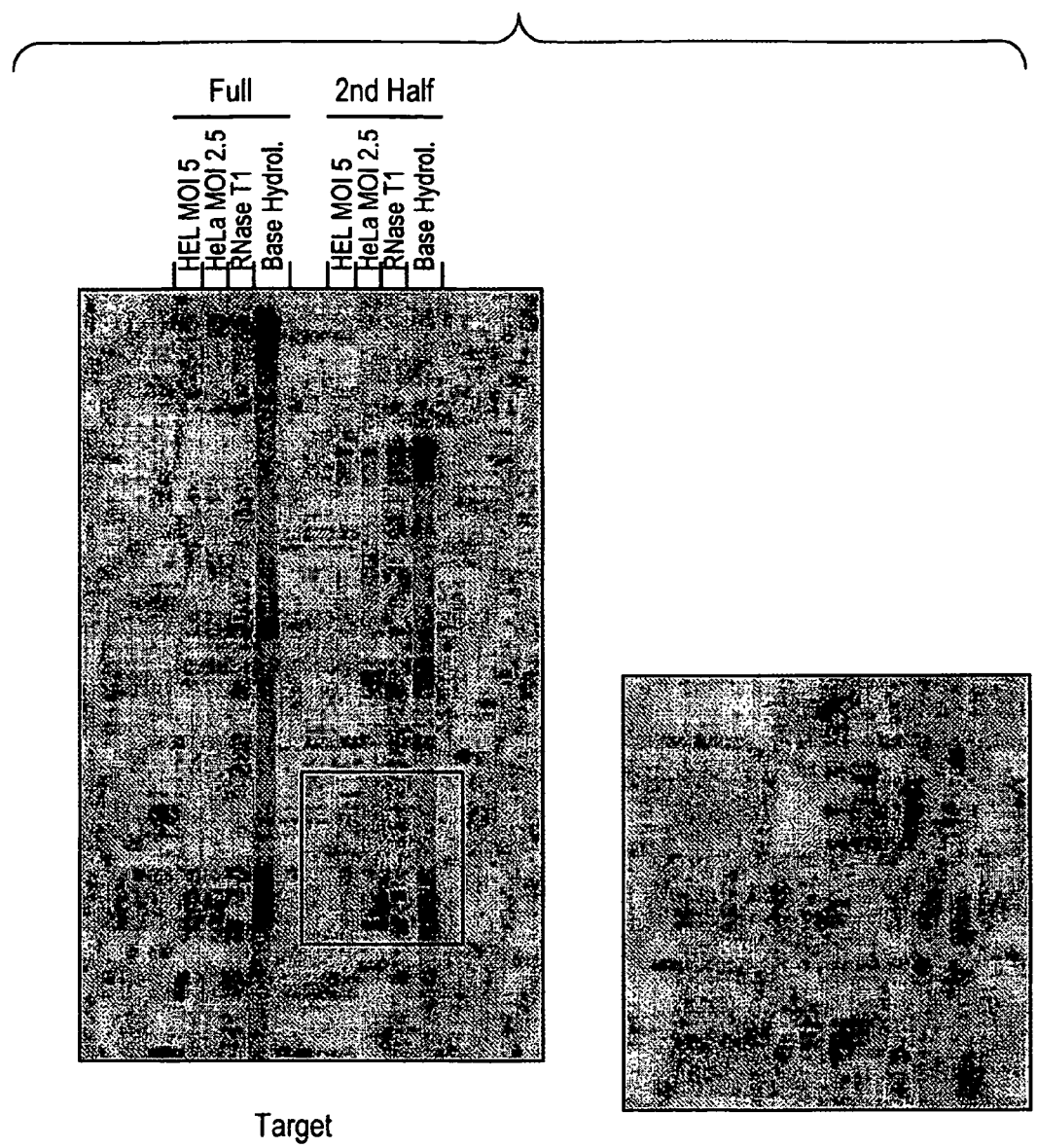
FIG. 14 is mapping analysis of VA-specific cleavage product.
Figure 15:
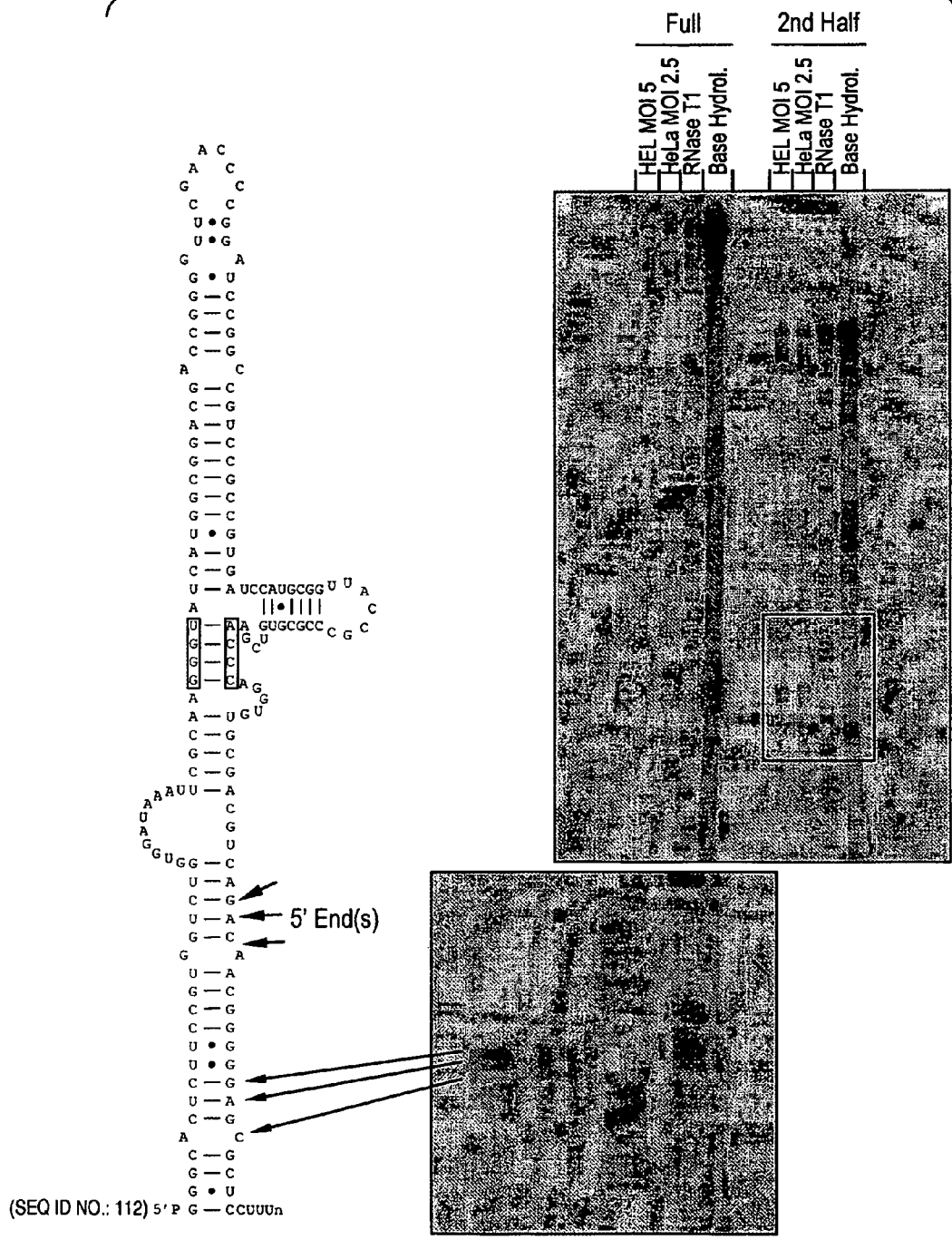
FIG. 15 is mapping analysis of the putative VA miRNA sites.

FIG. 14 presents a preliminary mapping study of VA-specific cleavage product. These studies provide preliminary data suggesting the approximate region of the VA RNA which produces a VA RNA-derived miRNA, or "miVA" and the approximate region in the target. RNA from target cleavage reactions similar to those shown in FIG. 13 were subjected to electrophoresis on a 6% sequencing gel alongside target RNAs that were subjected to RNase T1 digestion or base hydrolysis. On the right, the "2$^{nd}$ Half" lanes containing the cleavage products have been enlarged in order to analyze cleavage products at the level of single nucleotides. Utilization of this mapping along with sequence information of the target RNA allowed a preliminary mapping of the points of cleavage on the target (a putative target sequence in the region of cleavage. 5'-AGGGAAAGGAGCACTCCCCCGT-TGTCTGACGTCG-3', SEQ ID NO: 114; putative region containing potential miVA, 5'-CGUCAGACAACGGGG-GAGUGCUCCUUU-3', SEQ ID NO: 115) and a preliminary prediction of the putative VA-miRNA responsible for this cleavage (potential miVAs 5'-GACAACGGGG-GAGUGCUCCUU-3', SEQ ID NO: 116; 5'-ACAACGGGG-GAGUGCUCCUUU-3', SEQ ID NO: 117; and AACGGGG-GAGUGCUCCUUUUU-3', SEQ ID NO: 118). FIG. 15 presents the preliminary mapping of putative VA miRNA sites in Adenovirus type 5 VA RNA1 (SEQ ID NO: 112). The enlarged image of the "2$^{nd}$ Half" cleavage products and mapping from FIG. 14 are shown. The arrows depict the approximate bases where the site specific cleavage may be occurring, as well as the putative 5' ends of the VA-miRNAs.

Example XII

Target Cleavage is Directed by VA RNA1

Cytoplasmic extracts of infected cells were prepared from HeLa cells infected with wild type Adenovirus (type 5), dl331 virus (Adenovirus type 5 containing a deletion in the VA RNA1 locus, making the virus a VA RNA1-deletion mutant; courtesy of Dr. Thomas Shenk), or no virus ("mock" infected extracts), as described in Example XI. In this example, the "2$^{nd}$ Half" target was used, since this produced the only VA RNA1-specific cleavage products in the previous example. The extracts were incubated for the indicated times with 40× reaction mix, as described above in Example V, and a final concentration of 1 nM 2$^{nd}$ Half target. The results of this experiment are shown in FIG. 16. The results demonstrate that specific cleavage products only accumulate in extracts from human cells infected with wild type Ad-5, and not in "mock" infected extracts, or extracts made from cells infected with a VA RNA1-deletion mutant virus (dl3331). These results thus indicate that target cleavage is directed by the VA1 gene.

Example XIII

Accumulation of VA RNA1 and miVA1 in Infected Cells

Next, a Northern analysis of VA RNA-species in infected HeLa cells was performed essentially as described above in Example IX, with several modifications. The cells were infected with an MOI of 5 of wild type Adenovirus (type 5) and RNA was harvested at the indicated times using Trizol reagent. In this example, 25 µg RNA was loaded onto a 15% polyacrylamide gel. The gel was semi-dry electro-blotted as described, and was hybridized overnight with 25 pmol of a PNK-labeled oligonucleotide probe in Church Buffer (0.5M sodium phosphate, 1 mM EDTA, 7% SDS). The blot was initially cut in half and the bottom half was probed with an RNA oligonucleotide probe corresponding to the region of the ANR AV sequence from which the cleavage products were derived in Example XI. The top half of the blot was probed with a DNA oligonucleotide probe which was specific for the tRNA-Ile transfer RNA, and thus served as a loading control (probe described in Dev Cell. 2003 August; 5(2): 351-8; Houbaviy H B, Murray M F, Sharp P A). The top portion of the blot was then stripped by boiling the blot in 0.1% SDS, and was re-probed with the aforementioned VA RNA specific oligonucleotide RNA probe to detect full length VA RNA. Results of this experiment are shown in FIG. 17. The Northern blots are shown for each probe (upper panel), as well a graph depicting a quantification by phosphorimager analysis of the signals on the blots using the tRNA-Ile signal as a loading control (lower panel). The data indicate that both the full length VA RNA and miVA products accumulate over the course of infection with slightly different kinetics.

Example XIV

Processing of VA RNA2 in Fly Extracts and with Recombinant Human Dicer

Figure 18:
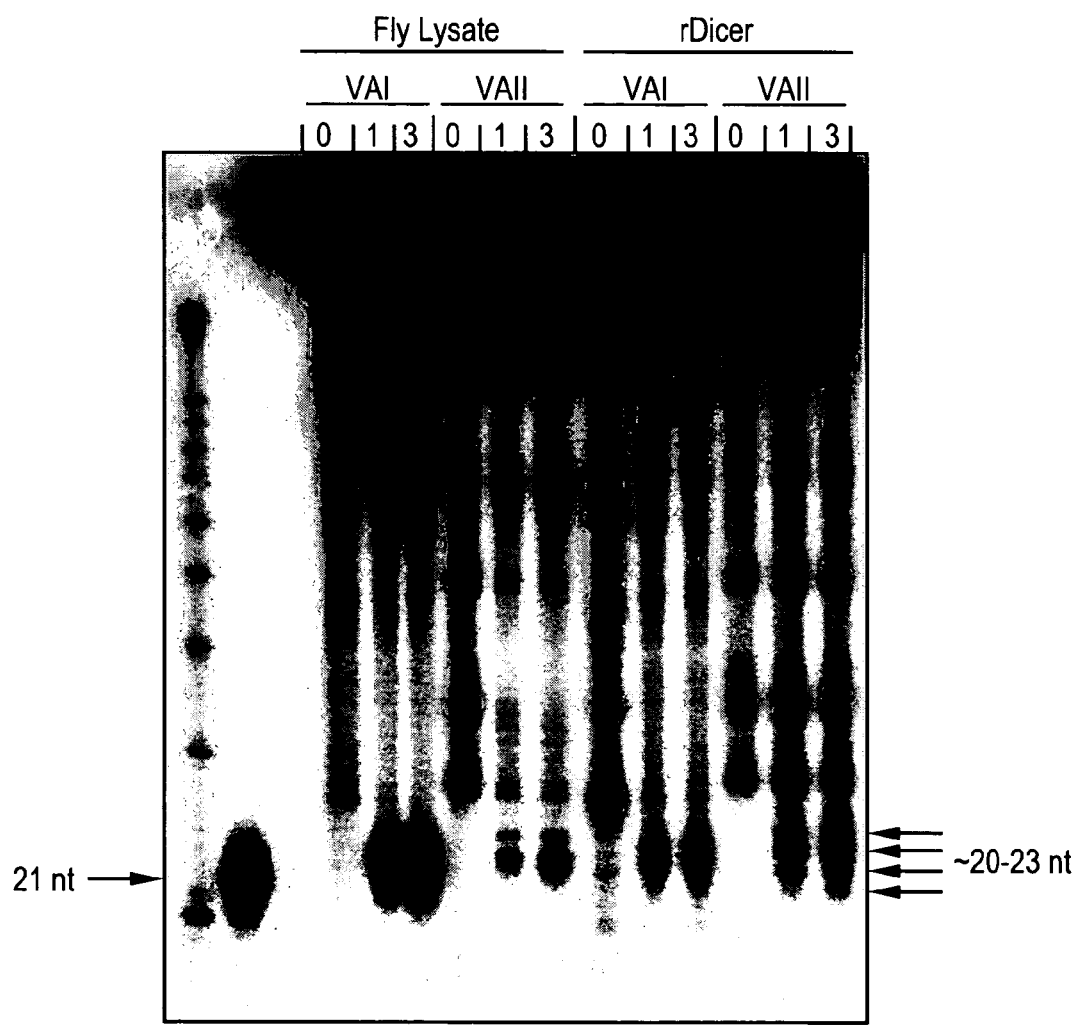
FIG. 18 is an analysis of VA RNA cleavage using *Drosophila* embryo extract and by recombinant Dicer enzyme.

Experiments were next performed to determine if VA RNA2 is also a substrate for cleavage by Dicer. Reactions were performed as described in example V, using either a labeled VA RNA1 or a VA RNA2 substrate present at 50 nM final concentration. Results are shown in FIG. 18. The data indicate that like VA RNA1, VA RNA2 also appears to be a substrate for cleavage by Dicer.

REFERENCES

1. B. N. Fields, D. M. Knipe, P. M. Howley, *Fundamental Virology* (Lippincott Williams & Wilkins, Philadelphia, Pa., ed. Third, 1996).
2. N. C. Lau, L. P. Lim, E. G. Weinstein, D. P. Bartel, *Science* 294, 858-62. (2001).
3. G. J. Hannon, *Nature* 418, 244-51. (2002).
4. G. Hutvagner, P. D. Zamore, *Curr Opin Genet Dev* 12, 225-32. (2002).
5. P. M. Waterhouse, M. B. Wang, T. Lough, *Nature* 411, 834-42. (2001).
6. O. Voinnet, *Trends Genet* 17, 449-59. (2001).
7. H. Li, W. X. Li, S. W. Ding, *Science* 296, 1319-21. (2002).
8. C. E. Samuel, *Clin Microbiol Rev* 14, 778-809, table of contents (October, 2001).
9. S. M. Elbashir et al, *Nature* 411, 494-8. (2001).
10. M. T. McManus, P. A. Sharp, *Nat Rev Genet* 3, 737-47. (2002).
11. A. Grishok et al., *Cell* 106, 23-34. (2001).
12. M. Lagos-Quintana, R. Rauhut, W. Lendeckel, T. Tuschl, *Science* 294, 853-8. (2001).
13. M. W. Rhoades et al, *Cell* 110, 513-20. (2002).
14. G. Hutvagner, P. D. Zamore, *Science* 297, 2056-60. (2002).
15. C. Llave, Z. Xie, K. D. Kasschau, J. C. Carrington, *Science* 297, 2053-6. (2002).
16. J. M. Jacque, K. Triques, M. Stevenson, *Nature* 418, 435-8. (2002)
17. A. P. McCaffrey et al., *Nature* 418, 38-39. (2002).
18. T. Tuschl, *Nat Biotechnol* 20, 446-8. (2002)
19. G. Sui et al., *Proc Natl Acad Sci USA* 99, 5515-20 (2002)
20. G. M. Barton, R. Medzhitov, *Proc Natl Acad Sci USA* 99, 14943-5. (2002)
21. M. B. Mathews, T. Shenk, *J. Virol* 65, 5657-62. (1991).
22. Y. Ma, M. B. Mathews, *J Virol* 70, 5083-99. (1996)
23. J. G. Howe, M. D. Shu, *J Virol* 62, 2790-8 (1988).
24. R. J. Bowden, J. P. Simas, A. J. Davis, S. Efstathiou, *J Gen Virol* 78 (Pt7), 1675-87 (1997).
25. R. Marschalek et al., *Nucleic Acids Res* 17, 631-43 (1989).
26. J. H. chen, S. Y. Le, J. V. Maizel, *Nucleic Acids Res* 28, 991-9 (2000).
27. L. Bieleski, S. J. Talbot, *J Virol* 75, 1864-9 (2001)
28. K. Ochs et al., *J Virol* 76, 2113-22 (2002).
29. C. M. Spahn et al., *Science* 291, 1959-62 (2001).
30. C. Lu and R. Bablanian, *Proc. Natl. Acad. Sci USA* 93, 2037-2042 (1996).
31. R. Sun, et al., *Proc. Natl. Acad. Sci. USA* 93, 11883-11888 (1996).
32. R. Jubin, *Curr. Opin. Investig. Drugs* 4(2): 162-167 (2003).
33. J. Neyts et al., *Verh K. Acad. Geneeskd. Belg.* 61(6): 661-697 (1999).
34. G. J. Belsham and N. Sonenberg, *Microbiol. Rev.* 60(3): 499-511 (1996).
35. M. Yi and S. M. Lemon, J Virol 77(6), 3557-3568 (2003).
36. G. Hutvagner et al., *PLoS Biology* 2(4), 0001-0011 (2004).
37. C. Thurner et al., *J General Virology* 85, 1113-1124 (2004)

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE 2

Examples of non-coding RNAs from various virus families

| Family/Subfamily | Genus | Virus | Non-coding RNA | Reference |
| --- | --- | --- | --- | --- |
| Gamma herpesvirinae | Lymphocryptovirus | Epstein-Barr virus (EBV) | EBER 1 | 1 |
| | | | EBER 2 | |
| Gamma herpesvirinae | | Herpesvirus papio (HPV) | HPV-1 | 23 |
| | | | HPV-2 | |

TABLE 2-continued

Examples of non-coding RNAs from various virus families

| Family/Subfamily | Genus | Virus | Non-coding RNA | Reference |
|---|---|---|---|---|
| Gamma herpesvirinae | | Murine gamma herpesvirus 68 (MHV-68) | Family of 8 tRNA-like sequences | 24 |
| Herpesviridae | Cytomegalovirus | Human Cytomegalovirus (HCMV) | CMER | 25 |
| Retroviridae | Lentivirus | Human immuno-deficiency virus (HIV) | Rev Responsive Element (RRE) TAR | 1, 26 |
| Poxviridae | Orthopoxvirus | Vaccinia virus | POLADs | 30 |
| Flaviviridae | unnamed | Hepatitis C Virus (HCV) | IRES | 32 |
| | | | 3' Nontranslated RNA Signal | 35 |
| Flaviviridae | Flavivirus | Dengue Virus | IRES | 33 |
| Picornaviridae | Apthovirus | Foot and Mouth Disease Virus | IRES | 34 |
| Picornaviridae | Enterovirus | Poliovirus | IRES | 34 |
| Herpesviridae | | Kaposis Sarcoma-associated Herpesvirus (KSHV) | IRES Polyadenylated nuclear RNA (PAN RNA; also called nut-1 or T1.1) | 31 |

What is claimed:

1. A method for identifying a druggable target, comprising:
   (a) contacting an isolated assay composition comprising an RNAi pathway molecule and at least one candidate RNA with a VA RNA, wherein the VA RNA is VA $RNA_I$ or VA $RNA_{II}$, and wherein the VA RNA has not been modified to include a heterologous sequence, under conditions such that the VA RNA is processed by Dicer to generate a double-stranded RNA agent; and
   (b) assaying for degradation of the candidate RNA, wherein the double-stranded RNA agent has sufficient sequence complementarity to the candidate RNA to direct RNAi;
   wherein degradation of the candidate RNA indicates that a gene or protein corresponding to the candidate RNA is a druggable target.

2. A method for identifying a druggable target, comprising:
   (a) contacting an isolated assay composition comprising an RNAi pathway molecule and at least one candidate RNA with a VA RNA, wherein the VA RNA is VA $RNA_I$ or VA $RNA_{II}$, and wherein the VA RNA has not been modified to include a heterologous sequence, under conditions such that the VA RNA is processed by Dicer to generate an RNA agent capable of incorporating into RISC, wherein the RNA agent is a siRNA or a miRNA; and
   (b) assaying for a decrease in the candidate RNA or a protein corresponding to the candidate RNA, wherein the RNA agent has sufficient sequence complementarity to the candidate RNA to direct RNAi;
   wherein a decrease in the candidate RNA or a protein corresponding to the candidate RNA indicates that a gene or protein corresponding to the candidate RNA is a druggable target.

3. A method for identifying a druggable target, comprising:
   (a) obtaining an assay composition isolated from a cell or organism infected with a virus comprising a nucleic acid molecule encoding a VA RNA under conditions such that the VA RNA is expressed from the nucleic acid molecule, wherein the VA RNA is VA $RNA_I$ or VA $RNA_{II}$, wherein the VA RNA has not been modified to include a heterologous sequence, and wherein the assay composition comprises an RNAi pathway molecule and at least one candidate RNA;
   (b) incubating the assay composition under conditions such that the VA RNA is processed by Dicer to generate an RNA agent capable of incorporating into RISC, wherein the RNA agent is a siRNA or a miRNA; and
   (c) assaying for a decrease in the candidate RNA or a protein corresponding to the candidate RNA, wherein the RNA agent has sufficient sequence complementarity to the candidate RNA to direct RNAi;
   wherein a decrease in the candidate RNA or a protein corresponding to the candidate RNA indicates that a gene or protein corresponding to the candidate RNA is a druggable target.

4. The method of claim 1 or 2, wherein the druggable target is an antiviral drug target.

5. The method of claim 1 or 2, wherein the candidate RNA is a ncRNA.

6. The method of claim 1 or 2, wherein the candidate RNA is a mRNA.

7. The method of claim 1 or 2, wherein the assay composition is a cell extract.

8. The method of claim 1 or 2, wherein the assay composition is a mammalian cell extract.

9. A method for identifying a druggable target, comprising:
   (a) obtaining an assay composition isolated from a cell or organism infected with a virus comprising a nucleic acid molecule encoding a VA RNA under conditions such that the VA RNA is expressed from the nucleic acid molecule, wherein the VA RNA is VA $RNA_I$ or VA $RNA_{II}$, wherein the VA RNA has not been modified to include a heterologous sequence, and wherein the assay composition comprises an RNAi pathway molecule and at least one candidate RNA;
   (b) incubating the assay composition under conditions such that the VA RNA is processed by Dicer to generate a double-stranded RNA agent; and
   (c) assaying for degradation of the candidate RNA, wherein the double-stranded RNA agent has sufficient sequence complementarity to the candidate RNA to direct RNAi;
   wherein degradation of the candidate RNA indicates that a gene or protein corresponding to the candidate RNA is a druggable target.

10. The method of claim 9 or 3, wherein the druggable target is an antiviral drug target.

11. The method of claim 9 or 3, wherein the candidate RNA is a ncRNA.

12. The method of claim 9 or 3, wherein the candidate RNA is a mRNA.

13. The method of claim 9 or 3, wherein the cell is a mammalian cell.

14. The method of claim 9 or 3, wherein the cell is a murine cell.

15. The method of claim 9 or 3, wherein the cell is a avian cell.

16. The method of claim 9 or 3, wherein the cell is a human cell.

17. The method of any one of claims 1, 9, 2 and 3, wherein a portion of the VA RNA and a portion of the candidate RNA share at least 90% sequence identity.

18. The method of any one of claims 1, 9, 2 and 3, further comprising the step of preselecting the candidate RNA based on its encoding a gene or protein having a desired cellular function.

19. The method of claim 18, wherein the desired cellular function is maintenance of cellular homeostasis.

20. The method of claim 18, wherein the desired cellular function is maintenance of differentiation.

21. The method of any one of claims 1, 9, 2 and 3, wherein the candidate RNA encodes a viral protein.

22. The method of any one of claims 1, 9, 2 and 3, wherein the candidate RNA encodes a cellular protein.

23. The method of any one of claims 1, 9, 2 and 3, wherein the candidate RNA is ncRNA regulating gene expression.

24. The method of claim 1 or 2, wherein the VA RNA is encoded by an adenovirus type 2 or adenovirus type 5 virus.

25. The method of any one of claims 1, 9, 2, and 3, wherein the VA RNA is VA $RNA_I$.

26. The method of any one of claims 1, 9, 2 and 3, wherein the VA RNA is expressed from a virus.

27. The method of claim 1 or 2, wherein the VA RNA is expressed from a vector.

28. The method of claim 1 or 2, wherein the VA RNA is expressed from a cassette.

29. The method of claim 1 or 2, wherein the assay composition is an insect cell extract.

30. The method of claim 9 or 3, wherein the virus is adenovirus type 2 or adenovirus type 5.

31. The method of any one of claims 1, 9, 2, and 3, wherein the VA RNA is VA-$RNA_{II}$.

* * * * *